(12) United States Patent
Moon et al.

(10) Patent No.: US 12,256,635 B2
(45) Date of Patent: Mar. 18, 2025

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Chungcheongnam-do (KR)

(72) Inventors: Doo-Hyeon Moon, Gyeonggi-Do (KR); Ji-Song Jun, Gyeonggi-Do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 790 days.

(21) Appl. No.: 17/241,735

(22) Filed: Apr. 27, 2021

(65) Prior Publication Data

US 2021/0257555 A1    Aug. 19, 2021

Related U.S. Application Data

(63) Continuation of application No. 15/779,606, filed as application No. PCT/KR2016/012459 on Nov. 1, 2016, now abandoned.

(30) Foreign Application Priority Data

Dec. 8, 2015  (KR) .................. 10-2015-0174137
Oct. 12, 2016  (KR) .................. 10-2016-0132040

(51) Int. Cl.

| H10K 85/60 | (2023.01) |
| C07D 491/06 | (2006.01) |
| C07D 495/06 | (2006.01) |
| C09K 11/06 | (2006.01) |
| H10K 30/80 | (2023.01) |
| H10K 50/11 | (2023.01) |
| H10K 50/16 | (2023.01) |
| H10K 101/00 | (2023.01) |
| H10K 101/10 | (2023.01) |

(52) U.S. Cl.
CPC ......... *H10K 85/654* (2023.02); *C07D 491/06* (2013.01); *C07D 495/06* (2013.01); *C09K 11/06* (2013.01); *H10K 85/615* (2023.02); *H10K 85/657* (2023.02); *H10K 85/6572* (2023.02); *C09K 2211/1007* (2013.01); *C09K 2211/1018* (2013.01); *C09K 2211/1029* (2013.01); *C09K 2211/185* (2013.01); *H10K 30/865* (2023.02); *H10K 50/11* (2023.02); *H10K 50/16* (2023.02); *H10K 2101/10* (2023.02); *H10K 2101/90* (2023.02)

(58) Field of Classification Search
CPC .. H10K 85/654; H10K 85/657; H10K 85/615; H10K 85/6572; H10K 2101/90; H10K 2101/10; H10K 50/16; H10K 50/11; H10K 30/865; C07D 491/06; C07D 495/06; C09K 11/06; C09K 2211/1007; C09K 2211/1018; C09K 2211/1029; C09K 2211/185; C09K 2211/1044; C09K 2211/187; C07F 9/587; C07F 15/06
See application file for complete search history.

(56) References Cited

U.S. PATENT DOCUMENTS

| 2013/0207082 A1 | 8/2013 | Cho et al. |
| 2016/0308146 A1 | 10/2016 | Parham et al. |
| 2016/0351825 A1* | 12/2016 | Kim ............... C07D 495/04 |
| 2019/0207125 A1 | 7/2019 | Ahn et al. |
| 2019/0214572 A1 | 7/2019 | Cho et al. |
| 2019/0221751 A1 | 7/2019 | Cho et al. |

FOREIGN PATENT DOCUMENTS

| KR | 20110066763 A | 6/2011 |
| KR | 20140119642 A | 10/2014 |
| KR | 20150077220 A | 7/2015 |
| KR | 20160075246 A | 6/2016 |
| WO | 2016105054 A2 | 6/2016 |

OTHER PUBLICATIONS

Search report for corresponding Taiwan Application No. 105137321 dated Jul. 17, 2020.

* cited by examiner

*Primary Examiner* — Shane Fang
(74) *Attorney, Agent, or Firm* — G. Creston Campbell

(57) ABSTRACT

An organic electroluminescent compound and an organic electroluminescent device comprising the same provide an organic electroluminescent device having low driving voltage and/or excellent power efficiency and/or improved driving lifespan.

10 Claims, No Drawings

ORGANIC ELECTROLUMINESCENT COMPOUND AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 15/779,606, filed May 29, 2018, which is the National Stage Entry of PCT/KR2016/012459, filed Nov. 1, 2016, both of which are incorporated by reference herein in their entirety.

TECHNICAL FIELD

The present disclosure relates to an organic electroluminescent compound and an organic electroluminescent device comprising the same.

BACKGROUND ART

Among display devices, an electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device is light-emitting materials. Until now, fluorescent materials have been widely used as light-emitting material. However, in view of electroluminescent mechanisms, since phosphorescent light-emitting materials theoretically enhance luminous efficiency by four (4) times compared to fluorescent light-emitting materials, phosphorescent light-emitting materials have been widely researched. Iridium(III) complexes have been widely known as phosphorescent light-emitting materials, including bis(2-(2'-benzothienyl)-pyridinato-N,C-3') iridium(acetylacetonate) [(acac) Ir(btp)$_2$], tris(2-phenylpyridine) iridium [Ir(ppy)$_3$] and bis(4,6-difluorophenylpyridinato-N,C2)picolinato iridium (Firpic) as red-, green- and blue-emitting materials, respectively.

In conventional technology, 4,4'-N,N'-dicarbazol-biphenyl (CBP) is the most widely known host material for phosphorescent materials. Recently, Pioneer (Japan) et al., developed a high performance organic electroluminescent device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the organic electroluminescent device is given by [(π/voltage)× current efficiency], and the power efficiency is inversely proportional to the voltage. Although the organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the organic electroluminescent device is short, and luminous efficiency is still necessary to improve. Accordingly, the materials constituting the organic layer in the device, in particular a host or a dopant constituting the light-emitting material, must be selected appropriately in order to realize the excellent characteristics of the organic EL device.

Also, the electron buffer layer is equipped to improve a problem of light-emitting luminance reduction which may occur due to the change of current properties in the device when the device is exposed to a high temperature during a process of producing panels. Thus, the properties of the compounds comprised in the electron buffer layer are important. In addition, the compound used in the electron buffer layer is desirable to perform a role of controlling an electron injection by the electron withdrawing characteristics and the electron affinity LUMO (lowest unoccupied molecular orbital) energy level, and thus may perform a role to improve the efficiency and the lifespan of the organic electroluminescent device.

Korean Patent Application Laid-Open No. 2014-0119642 discloses a compound comprising the following structure.

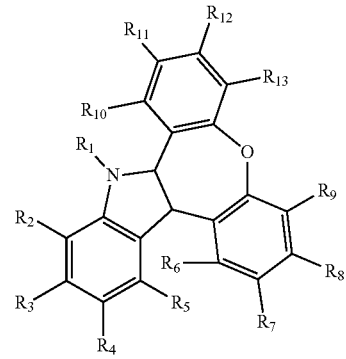

International Publication No. 2015-082046 discloses a compound comprising the following structure, but the compound having the structure in which a 7-membered ring comprising V is fused with a 5-membered ring is not specifically disclosed.

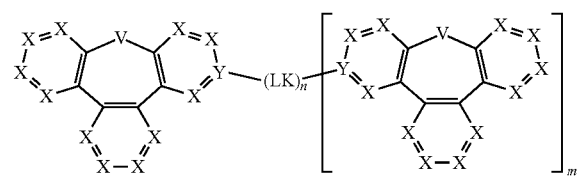

Korean Patent Application Laid-Open No. 2015-0077220 discloses a compound comprising the following structure, i.e. a fused azepine core structure.

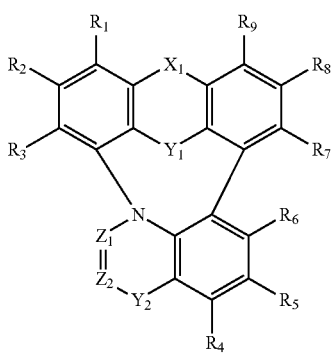

However, none of the literatures above specifically discloses a compound having a fused oxepin-carbazole core structure or a fused thiepin-carbazole core structure.

DISCLOSURE OF THE INVENTION

Problems to be Solved

The object of the present disclosure is to provide (1) an organic electroluminescent compound being effective to produce an organic electroluminescent device having low driving voltage and/or excellent power efficiency and/or significantly improved operative lifespan, and (2) an organic electroluminescent device comprising the organic electroluminescent compound.

Solution to Problems

As a result of intensive studies to solve the technical problem above, the present inventors found that the organic electroluminescent compound of the present disclosure may produce the organic electroluminescent device having high triplet energy and improved efficiency. Specifically, the present inventors found that the above objective can be achieved by an organic electroluminescent compound represented by the following formula 1:

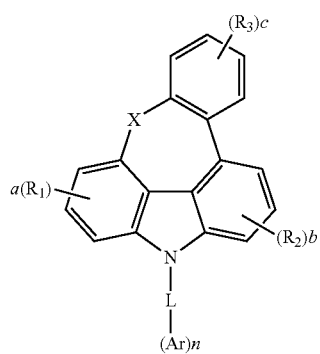

(1)

wherein

X represents O or S;

L represents a single bond, a substituted or unsubstituted (C6-C30)arylene, or a substituted or unsubstituted (3- to 30-membered)heteroarylene;

Ar represents a substituted or unsubstituted (C6-C30)aryl, a substituted or unsubstituted (3- to 30-membered) heteroaryl, or $-NR_{11}R_{12}$;

$R_1$ to $R_3$, each independently, represent hydrogen, deuterium, a substituted or unsubstituted (C1-C30)alkyl, a substituted or unsubstituted (C6-C30)aryl, a substituted or unsubstituted (3- to 30-membered)heteroaryl, or $-NR_{13}R_{14}$; or are linked to adjacent $R_1$, $R_2$ and $R_3$, respectively, to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;

$R_{11}$ to $R_{14}$, each independently, represent a substituted or unsubstituted (C1-C10)alkyl, a substituted or unsubstituted (C6-C30)aryl, or a substituted or unsubstituted (3- to 30-membered) heteroaryl;

n represents 1 or 2; where if n represents 2, each Ar may be the same or different;

a and b, each independently, represent an integer of 1 to 3; c represents an integer of 1 to 4; where if a to c, each independently, represent an integer of 2 or more, each of $R_1$ to $R_3$ may be the same or different; and the heteroaryl(ene) contains at least one heteroatom selected from B, N, O, S, Si, and P.

Effects of the Invention

The organic electroluminescent compound of the present disclosure can provide an organic electroluminescent device having low driving voltage and/or excellent power efficiency and/or improved driving lifespan.

EMBODIMENTS OF THE INVENTION

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The compound represented by formula 1 will be described in detail as follows.

In formula 1, X represents O or S.

In formula 1, L represents a single bond, a substituted or unsubstituted (C6-C30)arylene, or a substituted or unsubstituted (3- to 30-membered)heteroarylene; preferably, a single bond, a substituted or unsubstituted (C6-C25)arylene, or a substituted or unsubstituted (5- to 25-membered)heteroarylene; and more preferably, a single bond, a substituted or unsubstituted (C6-C18)arylene, or a substituted or unsubstituted (5- to 18-membered)heteroarylene. For example, L may represent a single bond, a substituted or unsubstituted phenylene, an unsubstituted biphenylene, an unsubstituted naphthylene, an unsubstituted carbazolylene, an unsubstituted quinazolinylene, an unsubstituted pyridinylene, a substituted or unsubstituted triazinylene, an unsubstituted pyrimidinylene, or an unsubstituted quinoxalinylene, wherein the substituents of the substituted phenylene may be at least one selected from the group consisting of a carbazolyl substituted with a phenyl, a triazinyl substituted with a diphenyl, and a diphenylamino, and the substituents of the substituted triazinylene may be a phenyl.

In formula 1, Ar represents a substituted or unsubstituted (C6-C30)aryl, a substituted or unsubstituted (3- to 30-membered)heteroaryl, or $-NR_{11}R_{12}$; preferably, a substituted or unsubstituted (C6-C25)aryl, a substituted or unsubstituted (5- to 25-membered)heteroaryl, or $-NR_{11}R_{12}$; more preferably, a substituted or unsubstituted (C6-C18)aryl, a substituted or unsubstituted (5- to 18-membered)heteroaryl, or $-NR_{11}R_{12}$. For example, Ar may represent a substituted or unsubstituted phenyl, an unsubstituted naphthyl, an unsubstituted biphenyl, an unsubstituted terphenyl, an unsubstituted naphthylphenyl, an unsubstituted fluoranthenyl, an unsubstituted triphenylenyl, a substituted triazinyl, an unsubstituted dibenzofuranyl, an unsubstituted dibenzothiophenyl, a substituted or unsubstituted carbazolyl, a fluorenyl substituted with a dimethyl, an unsubstituted isoquinolyl, a quinazolinyl unsubstituted or substituted with a phenyl, an unsubstituted pyridopyrimidinyl, a substituted pyridyl, a substituted pyrimidinyl, or $-NR_{11}R_{12}$, wherein the substituents of the substituted phenyl, the substituted pyridyl and the substituted pyrimidinyl may be a triazinyl substituted with a diphenyl; the substituents of the substituted carbazolyl may be at least one selected from the group consisting of a phenyl, and a carbazolyl substituted with a phenyl; and the substituents of a substituted triazinyl may be at least one selected from the group consisting of a phenyl, a biphenyl, a naphthyl and a naphthylphenyl.

In formula 1, $R_1$ to $R_3$, each independently, represent hydrogen, deuterium, a substituted or unsubstituted (C1-C10)alkyl, a substituted or unsubstituted (C6-C30)aryl, a substituted or unsubstituted (3- to 30-membered)heteroaryl, or $-NR_{13}R_{14}$; or are linked to adjacent $R_1$, $R_2$ and $R_3$, respectively, to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur. Preferably, $R_1$ to $R_3$, each independently, represent hydrogen, a substituted or unsubstituted (C6-C25)aryl, a substituted or unsubstituted (5- to 25-membered)heteroaryl, or $-NR_{13}R_{14}$; or are linked to adjacent $R_1$, $R_2$ and $R_3$, respectively, to form a substituted or unsubstituted, mono- or polycyclic, (C5-C25) alicyclic or aromatic ring, or the combination thereof, whose carbon atom(s) may be replaced with at least one heteroatom selected from nitrogen, oxygen, and sulfur. More preferably, $R_1$ to $R_3$, each independently, represent hydrogen, a substituted or unsubstituted (C6-C18)aryl, a substituted or unsubstituted (5- to 18-membered)heteroaryl, or $-NR_{13}R_{14}$; or are linked to adjacent $R_1$, $R_2$ and $R_3$, respectively, to form an unsubstituted, mono- or polycyclic, (C5-C18) aromatic ring. For example, $R_1$ to $R_3$, each independently, may represent hydrogen, a substituted or unsubstituted phenyl, an unsubstituted naphthylphenyl, an unsubstituted naphthyl, a triazinyl substituted with a diphenyl, a carbazolyl substituted with a phenyl, or $-NR_{13}R_{14}$; or may be linked to adjacent $R_1$, $R_2$ and $R_3$, respectively, to form an unsubstituted benzene ring, wherein the substituents of the substituted phenyl may be a mono- or di-(C6-C30)arylamino, preferably, at least one selected from the group consisting of a phenylbiphenylamino, diphenylamino and dimethylfluorenylphenylamino.

In formula 1, $R_{11}$ to $R_{14}$, each independently, represent a substituted or unsubstituted (C1-C10)alkyl, a substituted or unsubstituted (C6-C30)aryl, or a substituted or unsubstituted (3- to 30-membered)heteroaryl; preferably, a substituted or unsubstituted (C6-C25)aryl, or a substituted or unsubstituted (5- to 25-membered)heteroaryl; and more preferably, a substituted or unsubstituted (C6-C18)aryl. For example, $R_{11}$ and $R_{12}$, each independently, may represent an unsubstituted phenyl, an unsubstituted naphthyl, an unsubstituted biphenyl, an unsubstituted naphthylphenyl, or a fluorenyl substituted with a dimethyl, and $R_{13}$ and $R_{14}$, each independently, may represent an unsubstituted phenyl, or an unsubstituted biphenyl.

In formula 1, n represents 1 or 2; where if n represents 2, each Ar may be the same or different.

In formula 1, a and b, each independently, represent an integer of 1 to 3; c represents an integer of 1 to 4; where if a to c, each independently, represent an integer of 2 or more, each of $R_1$ to $R_3$ may be the same or different. Preferably, a to c, each independently, represent 1 or 2.

According to one embodiment of the present disclosure, in formula 1, L represents a single bond, a substituted or unsubstituted (C6-C25)arylene, or a substituted or unsubstituted (5- to 25-membered)heteroarylene; Ar represents a substituted or unsubstituted (C6-C25)aryl, a substituted or unsubstituted (5- to 25-membered)heteroaryl, or $-NR_{11}R_{12}$; $R_1$ to $R_3$, each independently, represent hydrogen, a substituted or unsubstituted (C6-C25)aryl, a substituted or unsubstituted (5- to 25-membered)heteroaryl, or $-NR_{13}R_{14}$; or are linked to adjacent $R_1$, $R_2$ and $R_3$, respectively, to form a substituted or unsubstituted, mono- or polycyclic, (C5-C25) alicyclic or aromatic ring, or the combination thereof, whose carbon atom(s) may be replaced with at least one heteroatom selected from nitrogen, oxygen, and sulfur; $R_{11}$ to $R_{14}$, each independently, represent a substituted or unsubstituted (C6-C25)aryl, or a substituted or unsubstituted (5- to 25-membered)heteroaryl; and a to c, each independently, represent 1 or 2.

According to another embodiment of the present disclosure, in formula 1, L represents a single bond, a substituted or unsubstituted (C6-C18)arylene, or a substituted or unsubstituted (5- to 18-membered)heteroarylene; Ar represents a substituted or unsubstituted (C6-C18)aryl, a substituted or unsubstituted (5- to 18-membered)heteroaryl, or $-NR_{11}R_{12}$; $R_1$ to $R_3$, each independently, represent hydrogen, a substituted or unsubstituted (C6-C18)aryl, a substituted or unsubstituted (5- to 18-membered)heteroaryl, or $-NR_{13}R_{14}$; or are linked to adjacent $R_1$, $R_2$ and $R_3$, respectively, to form an unsubstituted, mono- or polycyclic, (C5-C18) aromatic ring; $R_{11}$ to $R_{14}$, each independently, represent a substituted or unsubstituted (C6-C18)aryl; and a to c, each independently, represent 1 or 2.

Herein, the term "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. The term "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. The term "(C3-C30) cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. The term "(3- to 7-membered) heterocycloalkyl" is a cycloalkyl having 3 to 7, preferably 5 to 7, ring backbone atoms, including at least one heteroatom selected from B, N, O, S, Si, and P, preferably O, S, and N, and includes tetrahydrofuran, pyrrolidine, thiolan, tetrahydropyran, etc. The term "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may comprise a spiro structure. The above aryl(ene) may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered)heteroaryl (ene)" is an aryl having 3 to 30 ring backbone atoms, including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); may comprise a spiro structure; and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted aryl(ene), the substituted heteroaryl(ene), the substituted alkyl, and the substituted mono- or polycyclic, alicyclic or aromatic ring, or the combination thereof, in L, Ar, $R_1$ to $R_3$, and $R_{11}$ to $R_{14}$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C1-C30)alkyl or a (C6-C30)aryl; a (C6-C30)aryl unsubstituted or substituted with a (3- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; preferably, are at least one selected from the group consisting of a (C1-C20)alkyl, a (C6-C25)aryl, a (5- to 25-membered)heteroaryl unsubstituted or substituted with a (C6-C25) aryl, and a di(C6-C25) arylamino; more preferably, are at least one selected from the group consisting of a (C1-C10)alkyl, a (C6-C18)aryl, a (5- to 18-membered)heteroaryl unsubstituted or substituted with a (C6-C18)aryl, and a di(C6-C18)arylamino; and for example, may be at least one selected from the group consisting of a methyl, a phenyl, a biphenyl, a naphthyl, a naphthylphenyl, a triazinyl substituted with a diphenyl, a carbazolyl substituted with a phenyl, a diphenylamino, phenylbiphenylamino and dimethylfluorenylphenylamino.

The organic electroluminescent compound represented by formula 1 includes the following compounds, but is not limited thereto:

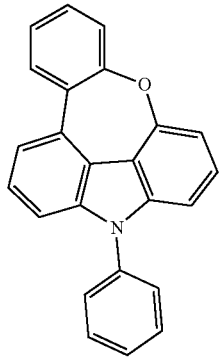

C-1

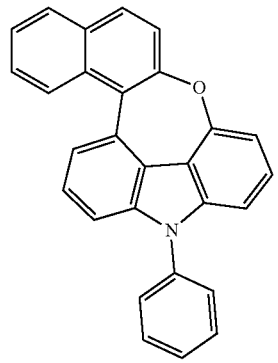

C-2

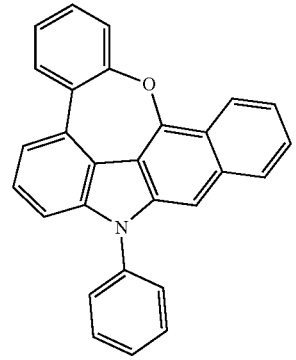

C-3

C-4
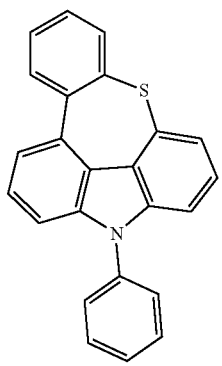
C-5
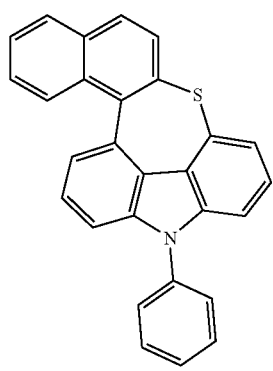
C-6
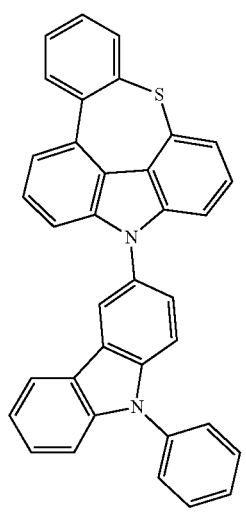
C-7
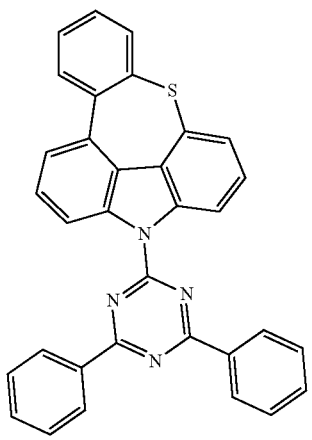
C-8
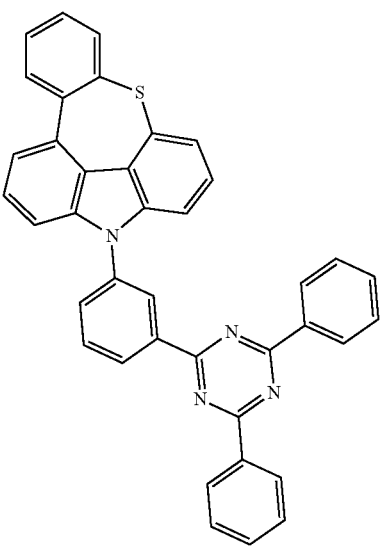
C-9
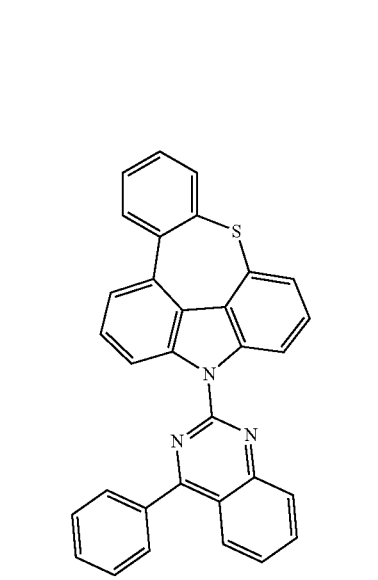

C-10 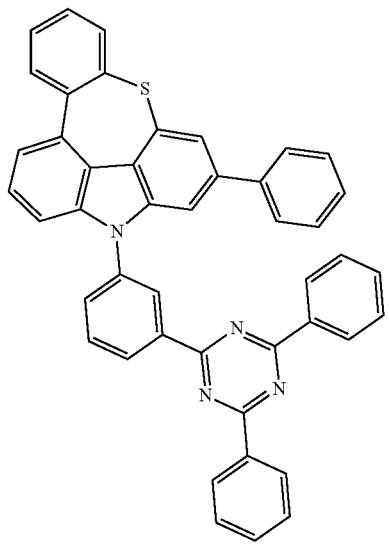
C-11 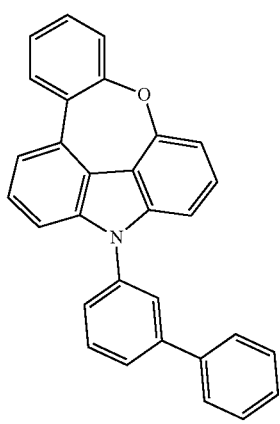
C-12 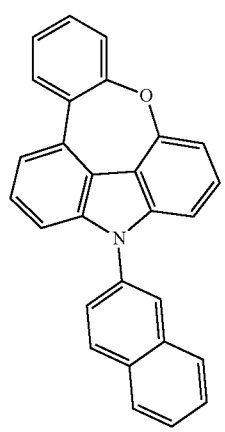
C-13 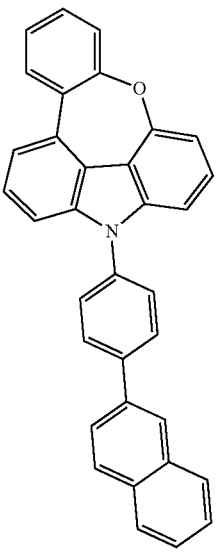
C-14 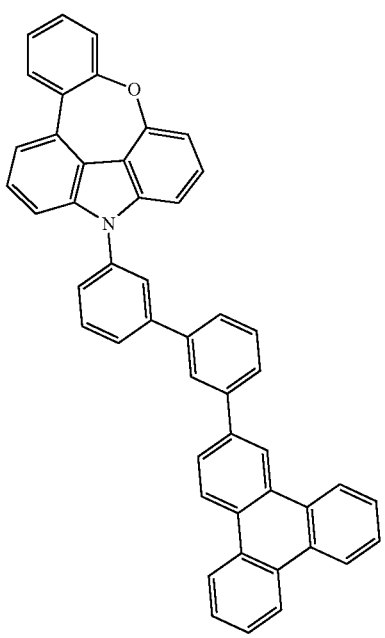
C-15 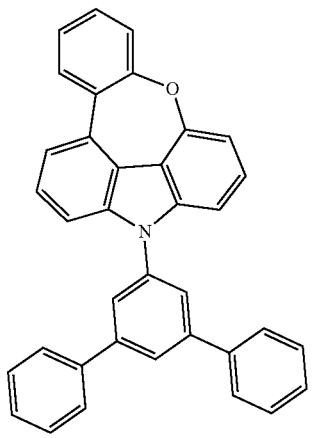

C-16
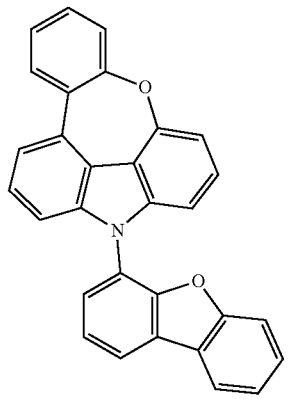
C-17
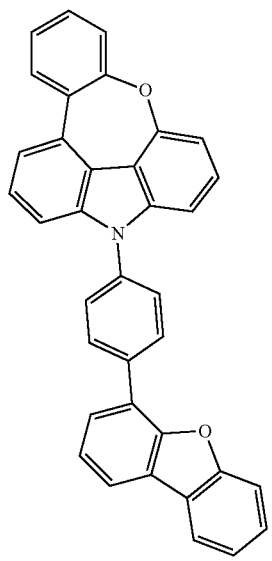
C-18
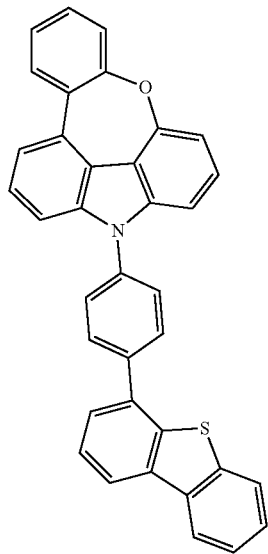
C-19
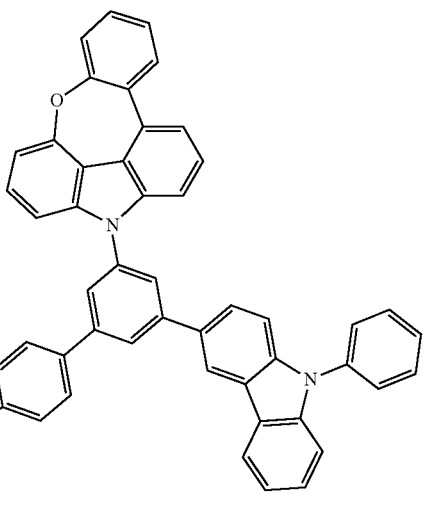
C-20
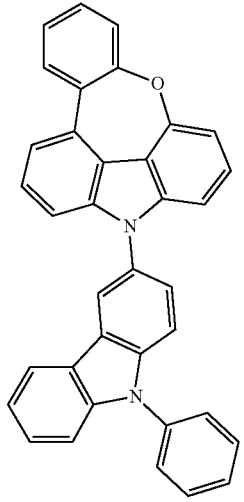

C-21
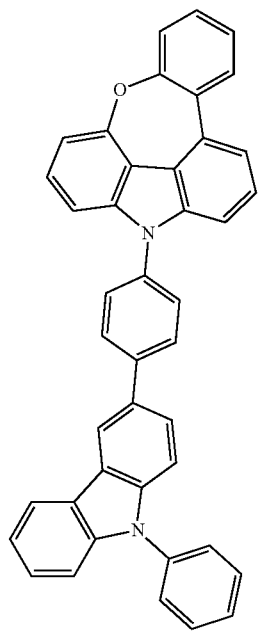
C-22
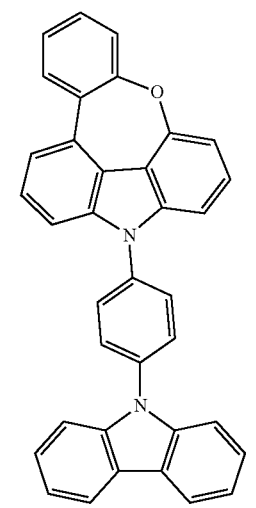
C-23
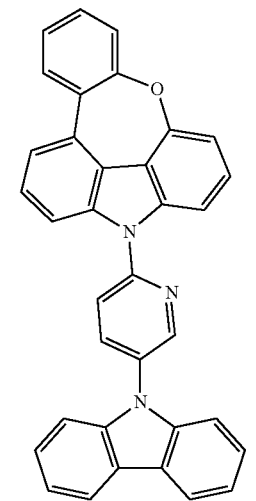
C-24
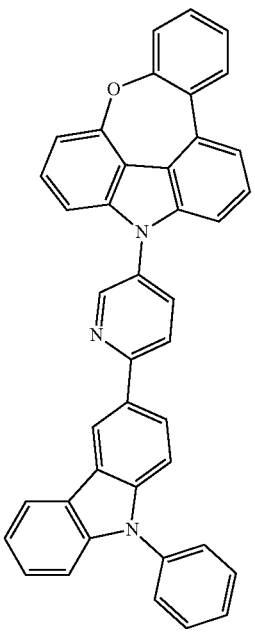
C-25
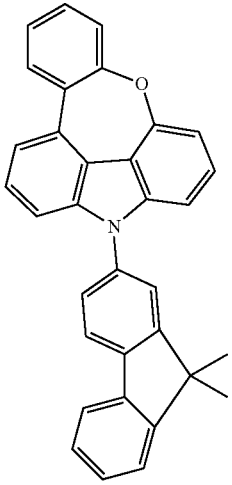

C-26
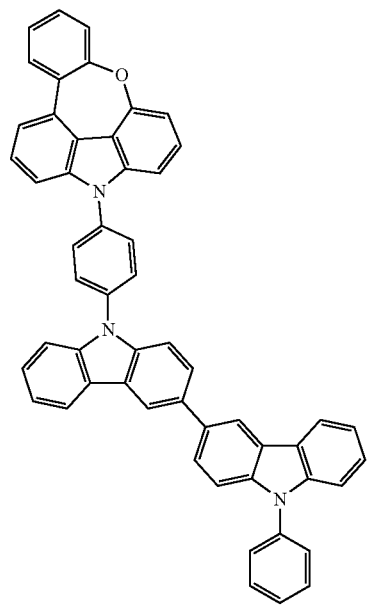
C-27
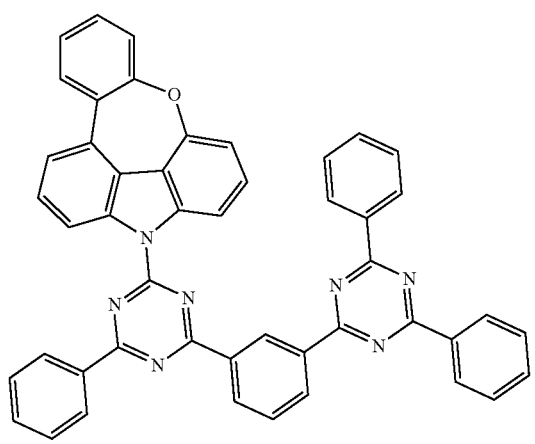
C-28
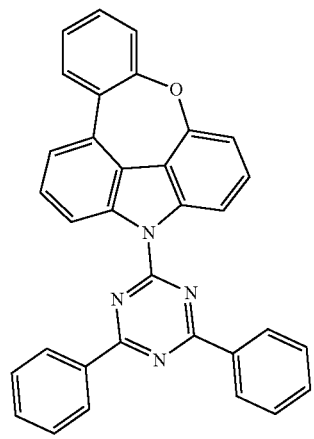
C-29
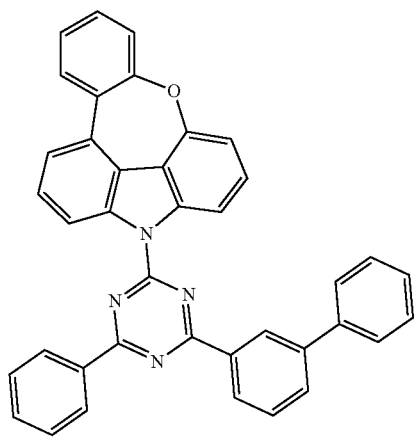
C-30
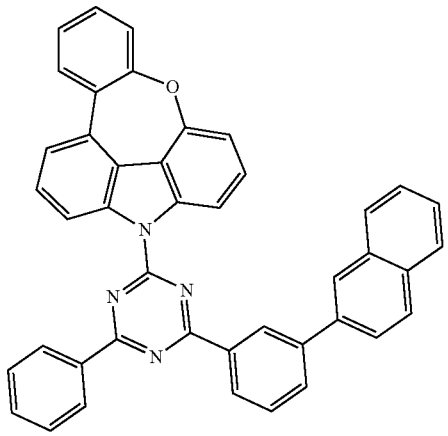
C-31
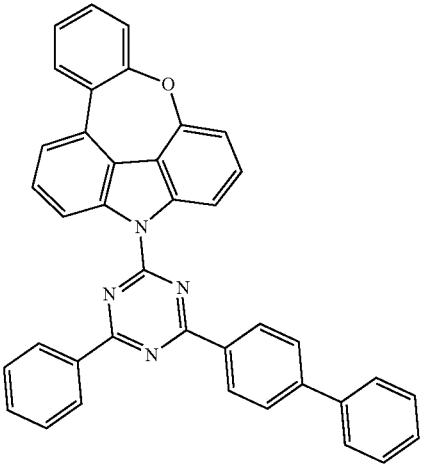

C-32
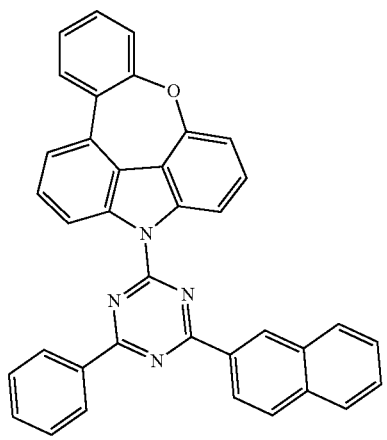
C-33
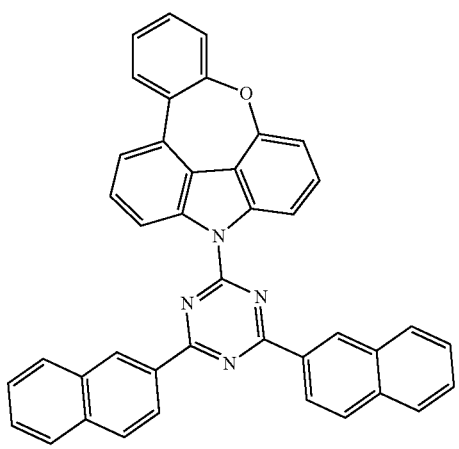
C-34
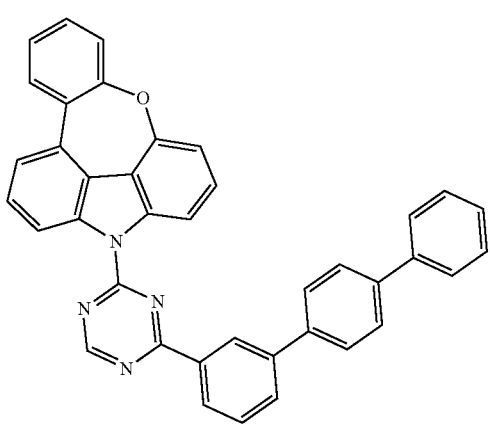
C-35
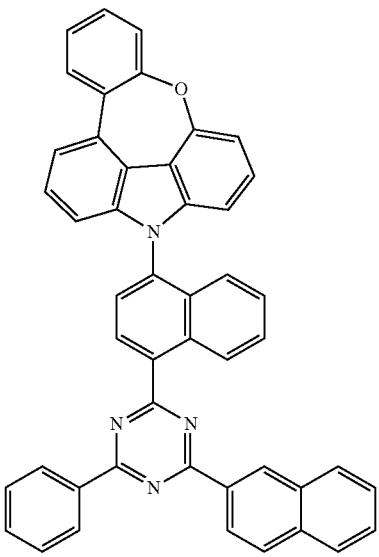
C-36
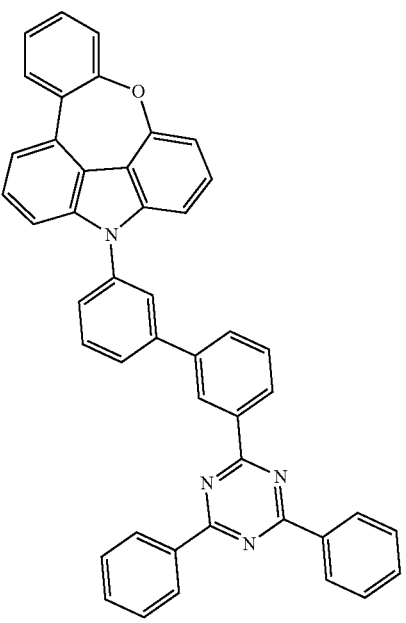

C-37
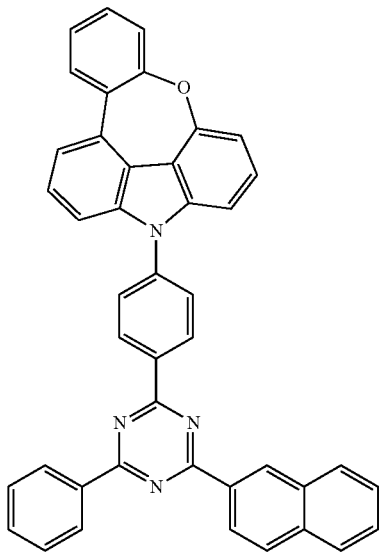
C-38
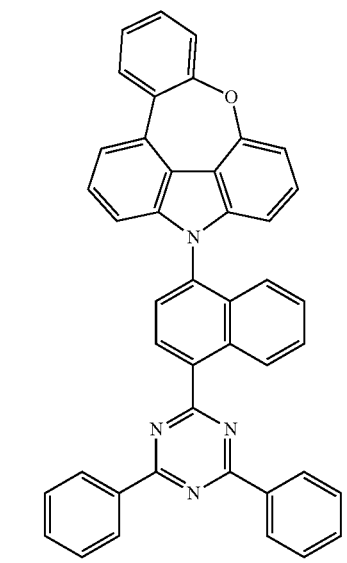
C-39
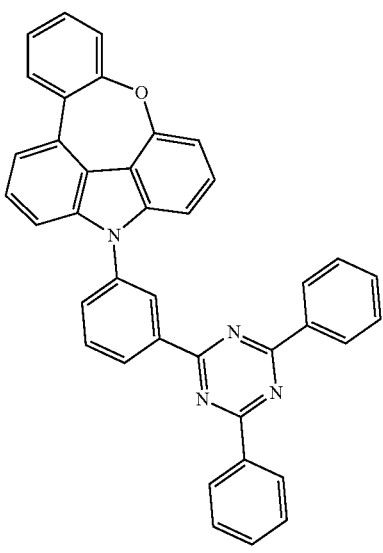
C-40
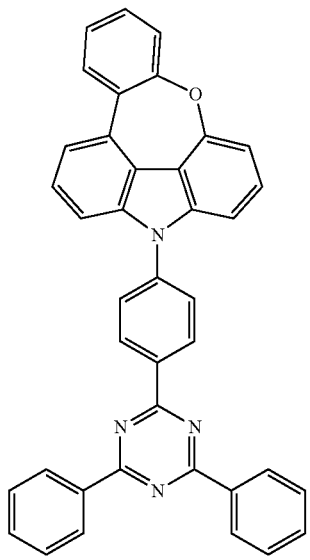
C-41
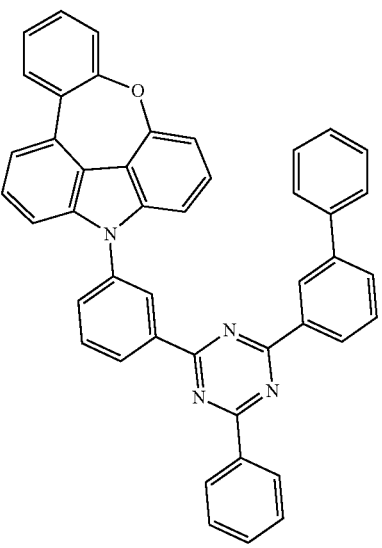

C-42
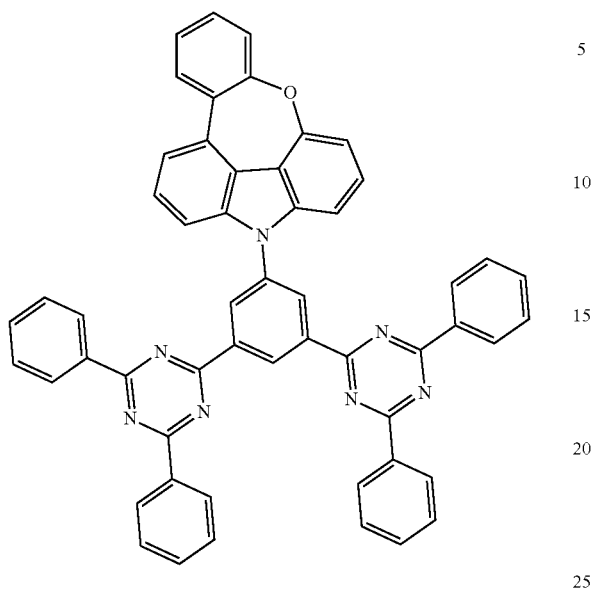
C-43
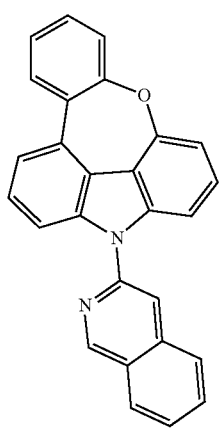
C-44
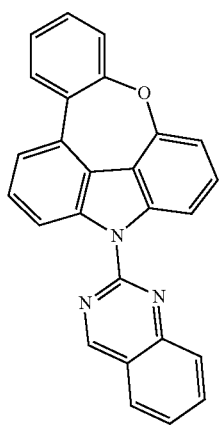
C-45
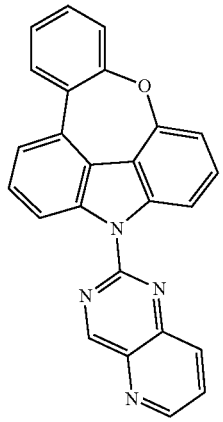
C-46
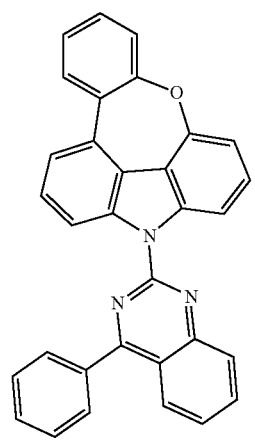
C-47
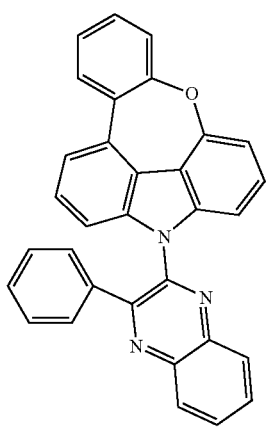

C-48
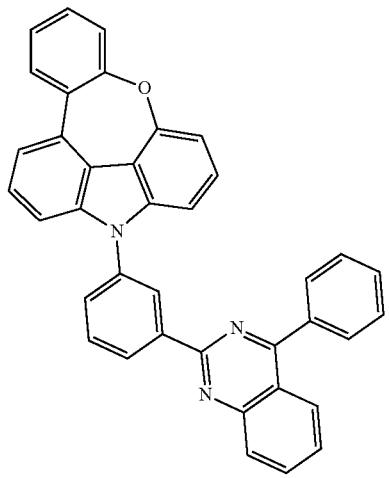
C-49
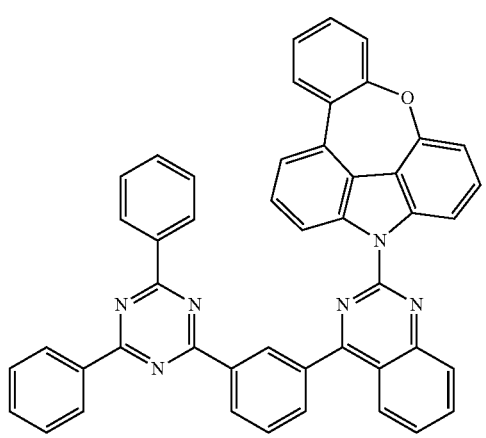
C-50
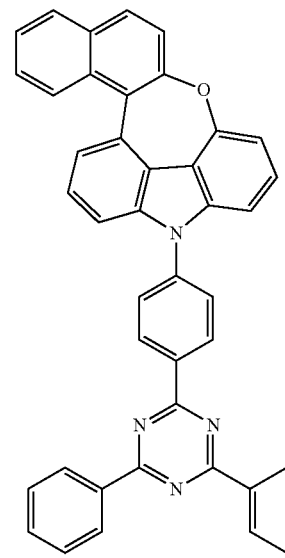
C-51
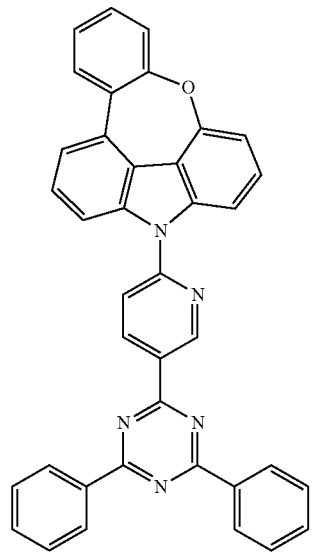
C-52
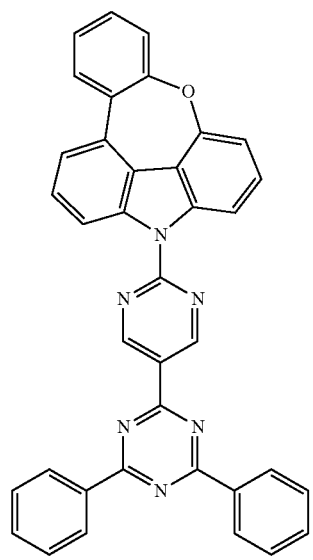
C-53
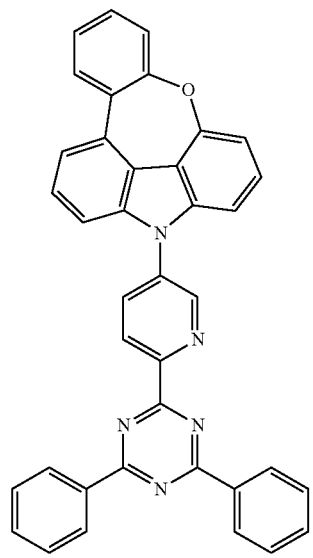

C-54
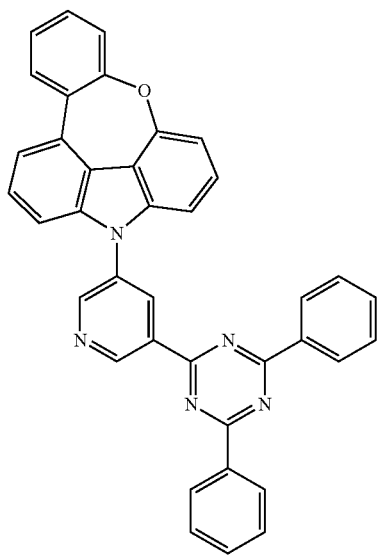
C-55
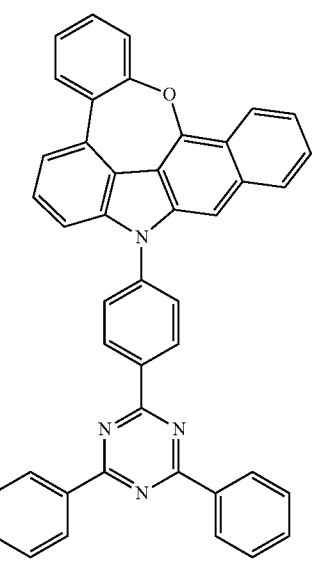
C-56
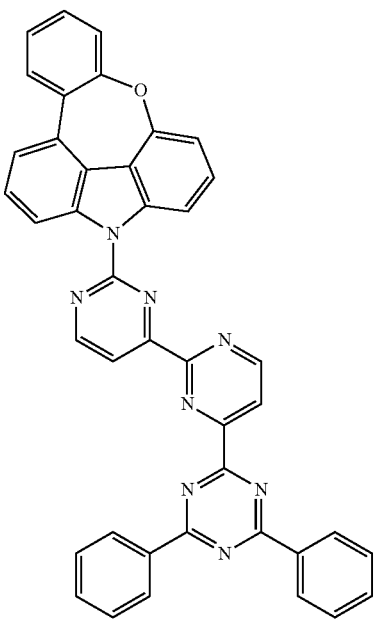
C-57
C-58
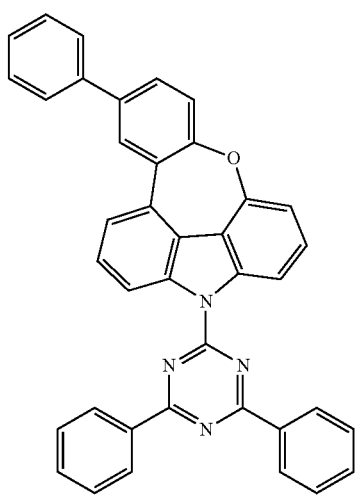

C-59
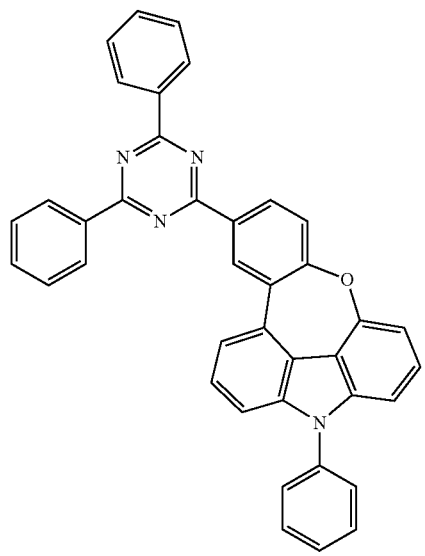
C-60
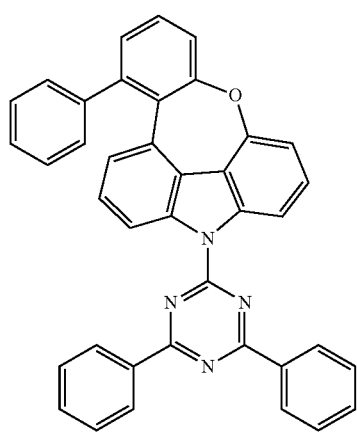
C-61
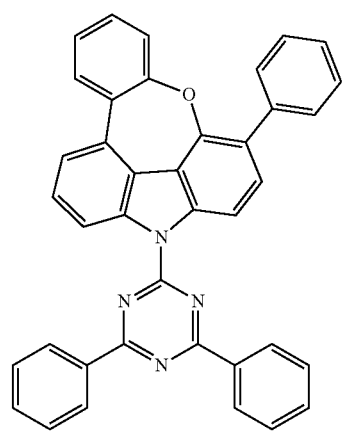
C-62
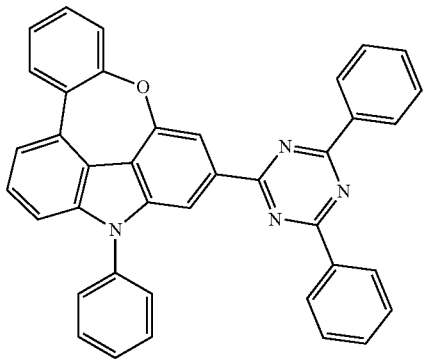
C-63
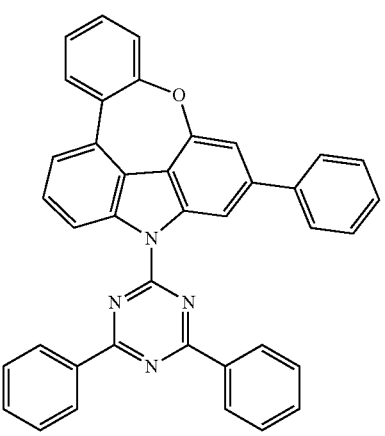
C-64
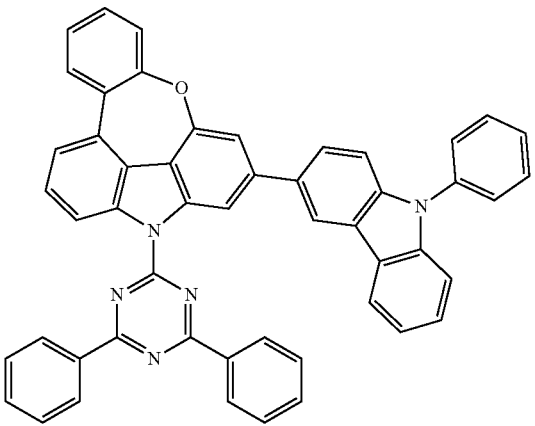

C-65
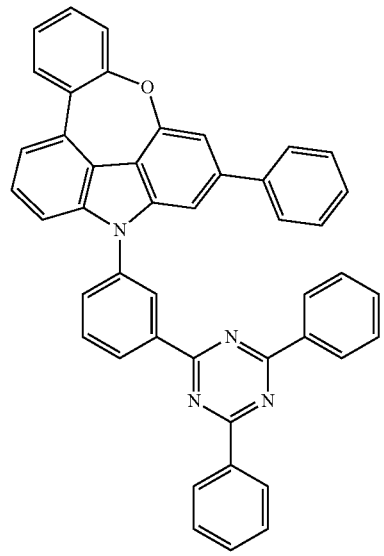
C-67
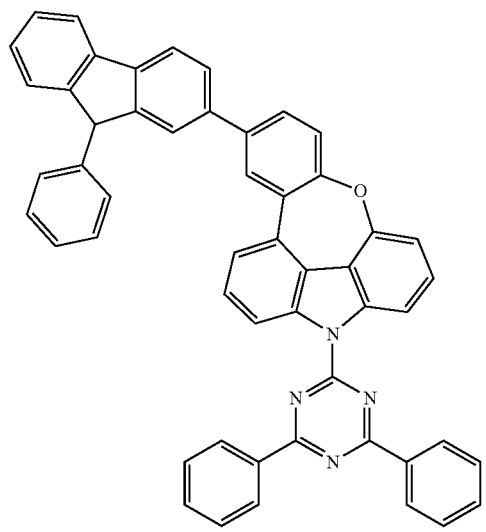
C-68
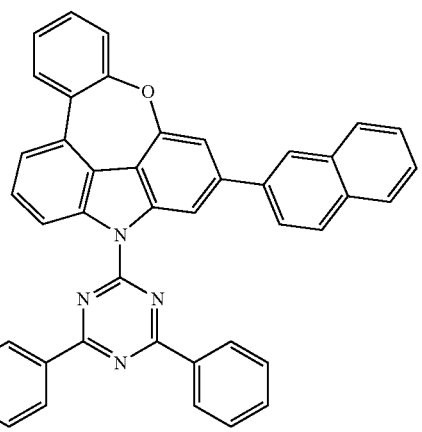
C-66
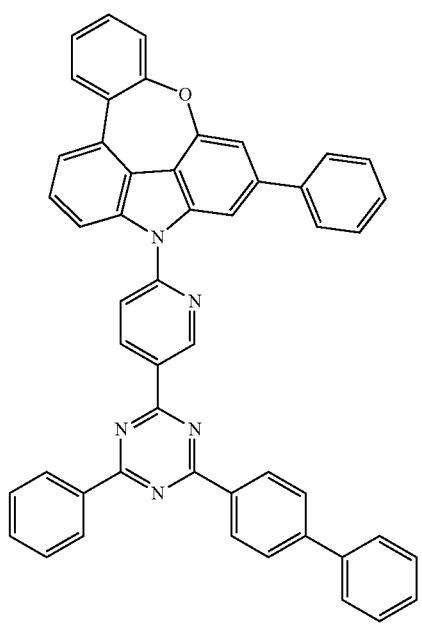
C-69
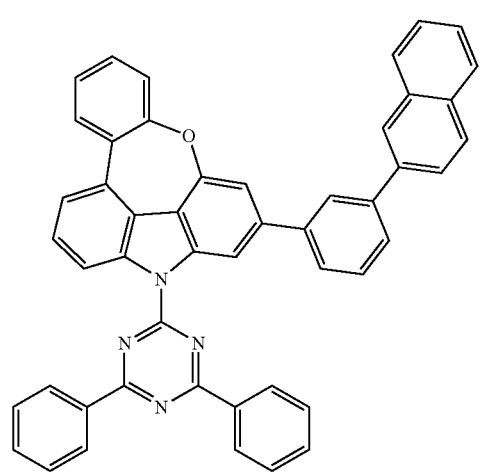

C-70
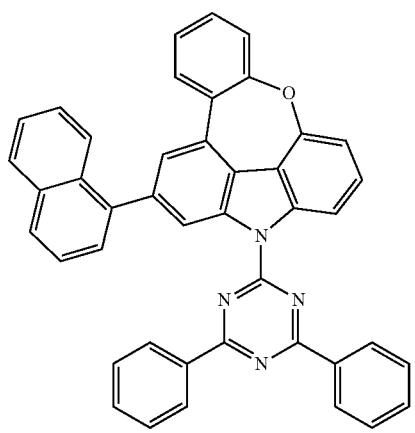
C-71
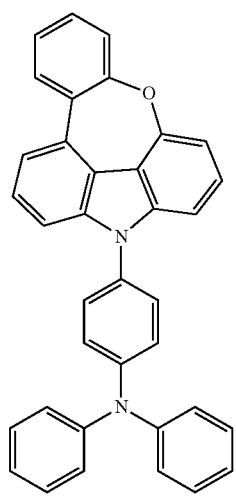
C-72
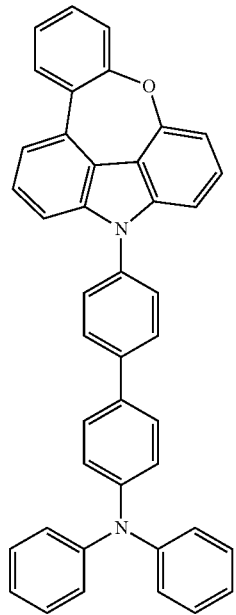
C-73
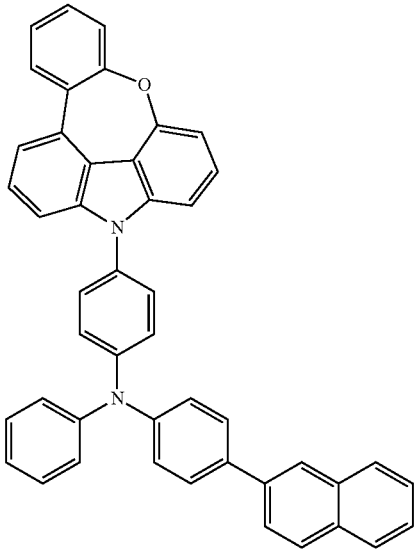
C-74
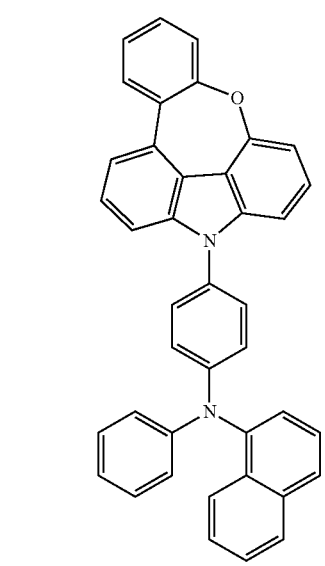
C-75
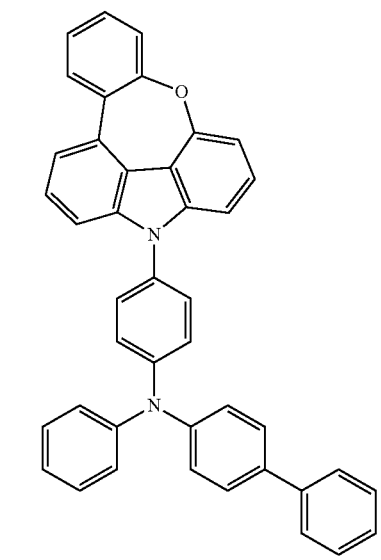

C-76
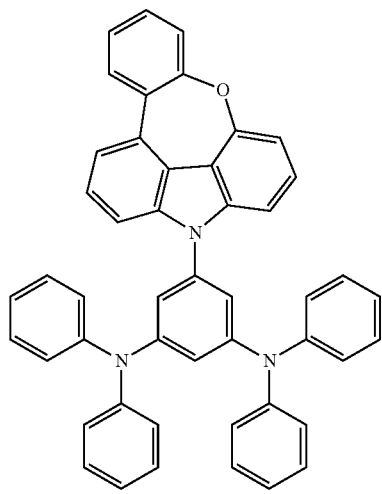
C-77
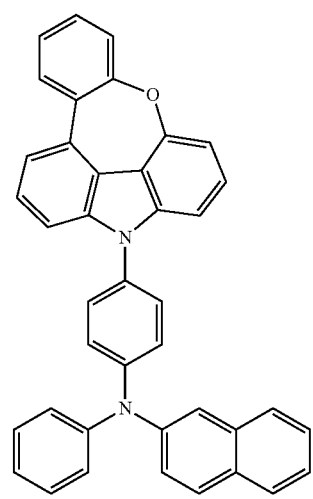
C-78
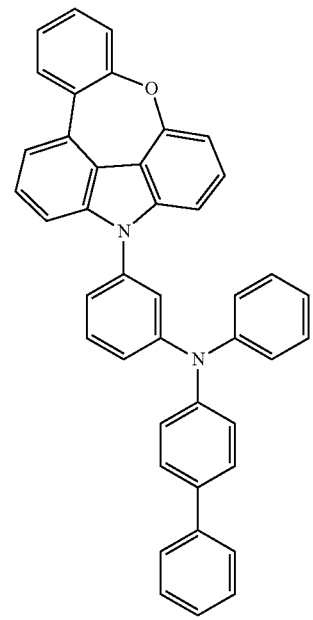
C-79
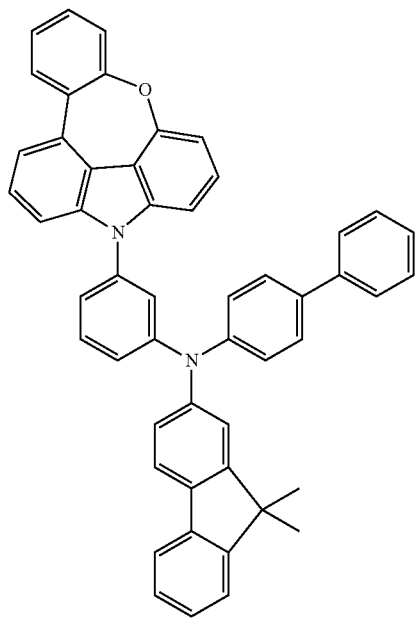
C-80
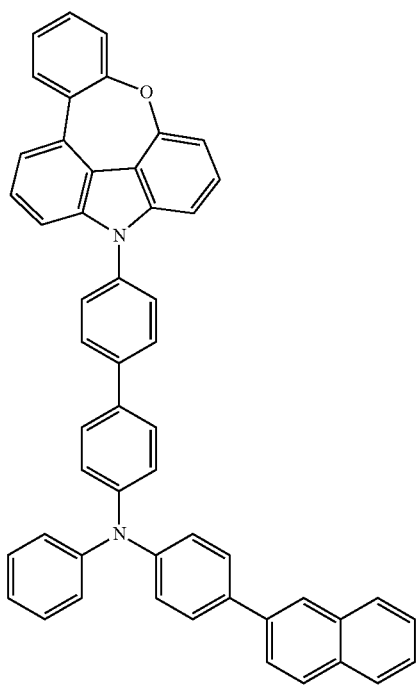

C-81
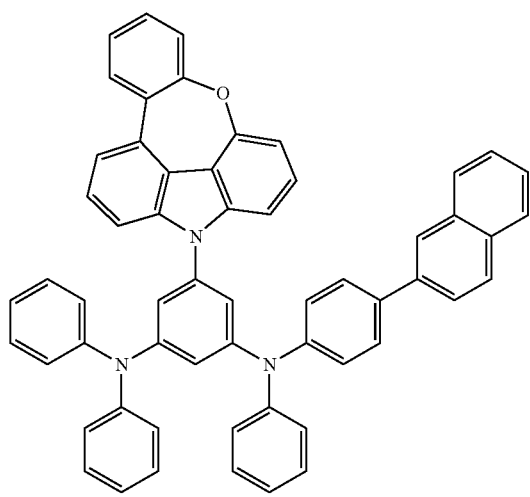
C-82
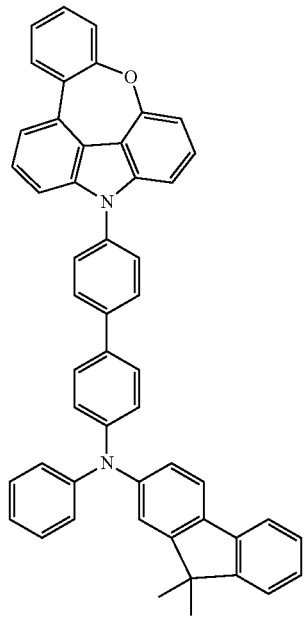
C-83
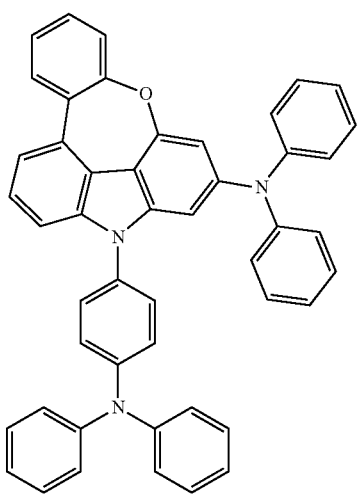
C-84
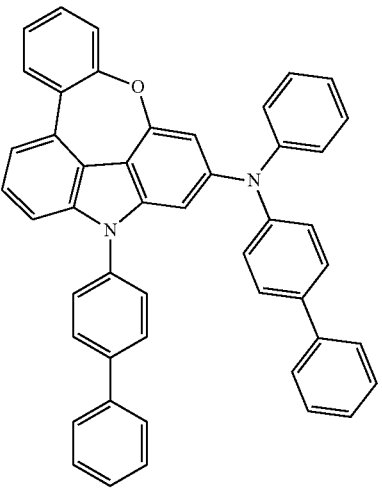
C-85

C-86
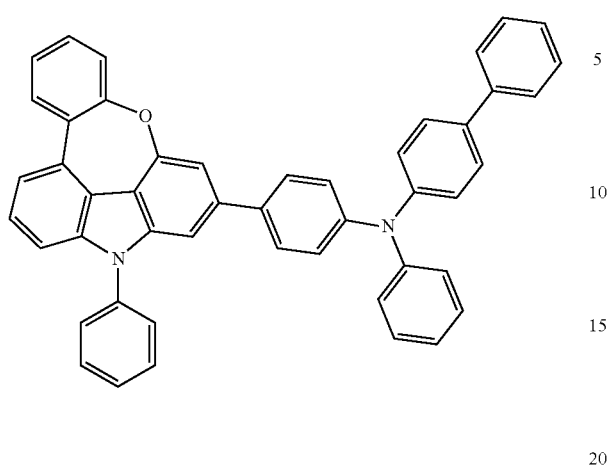
C-89
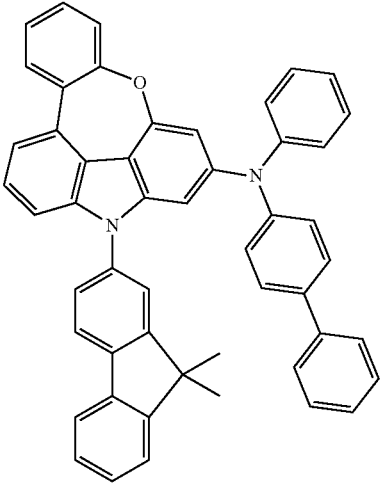
C-87
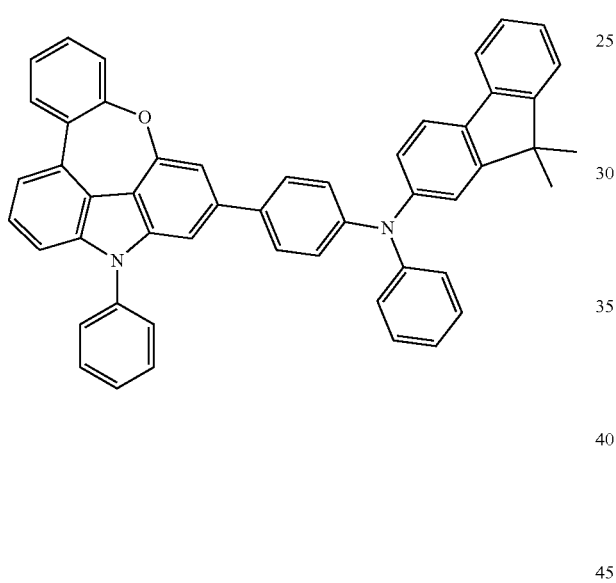
C-90
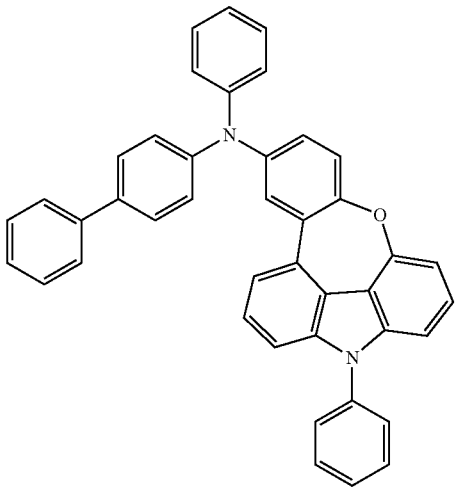
C-88
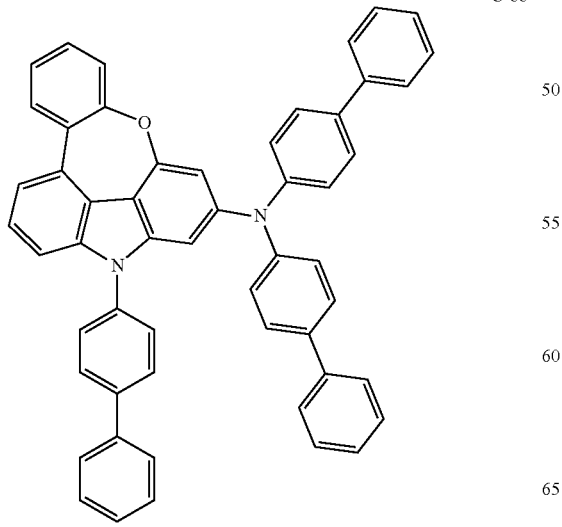
C-91
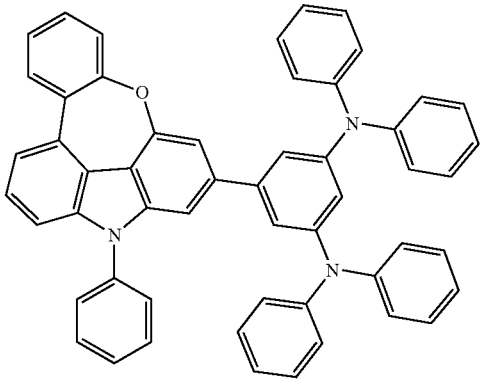

C-92
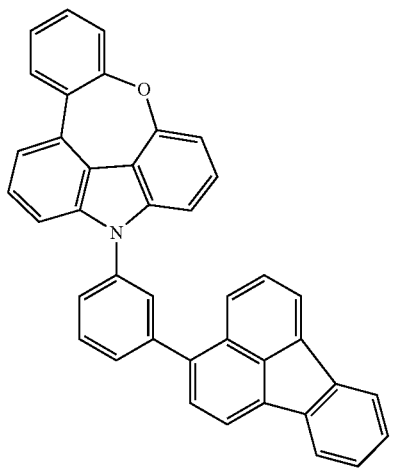
C-93
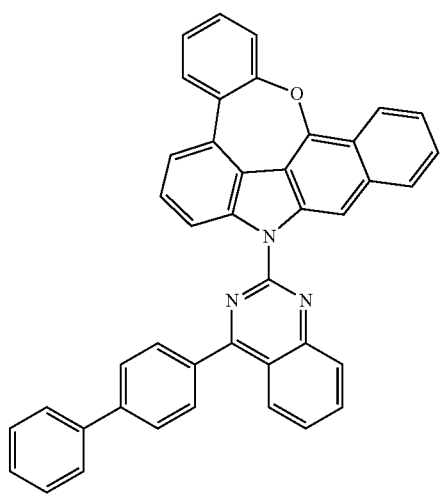
C-94
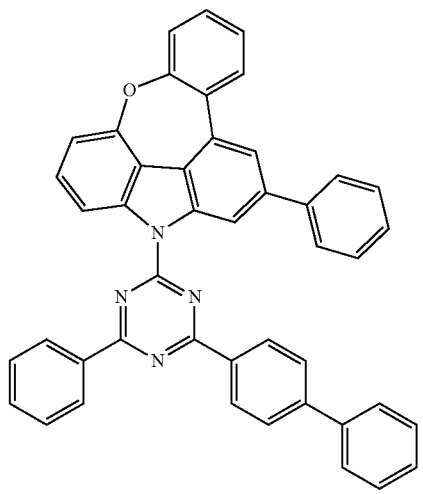
C-95
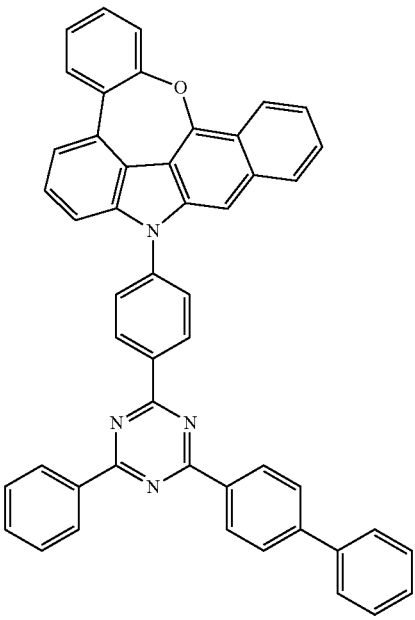
C-96
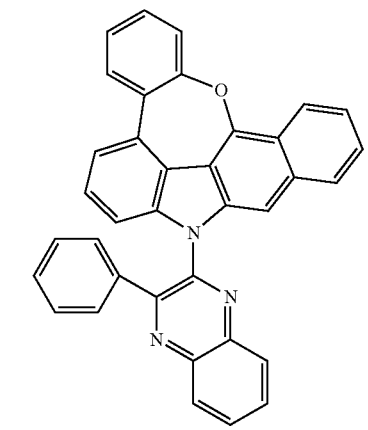
C-97
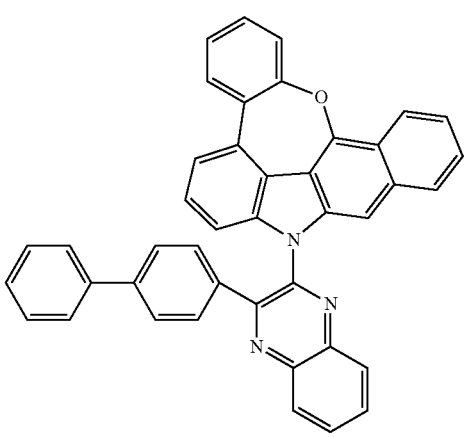

C-98
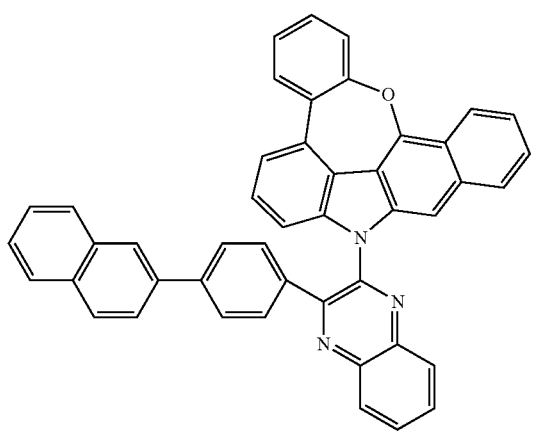
C-99
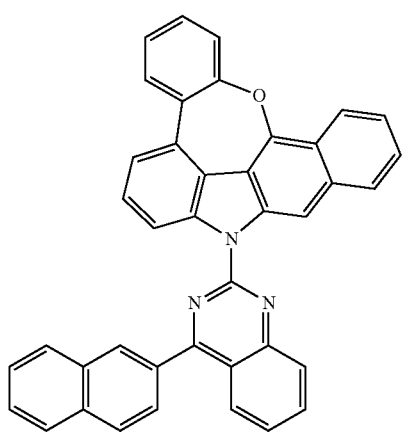
The organic electroluminescent compound of the present disclosure may be produced by a synthetic method known to a person skilled in the art, for example, the following reaction schemes:
[Reaction Scheme 1]
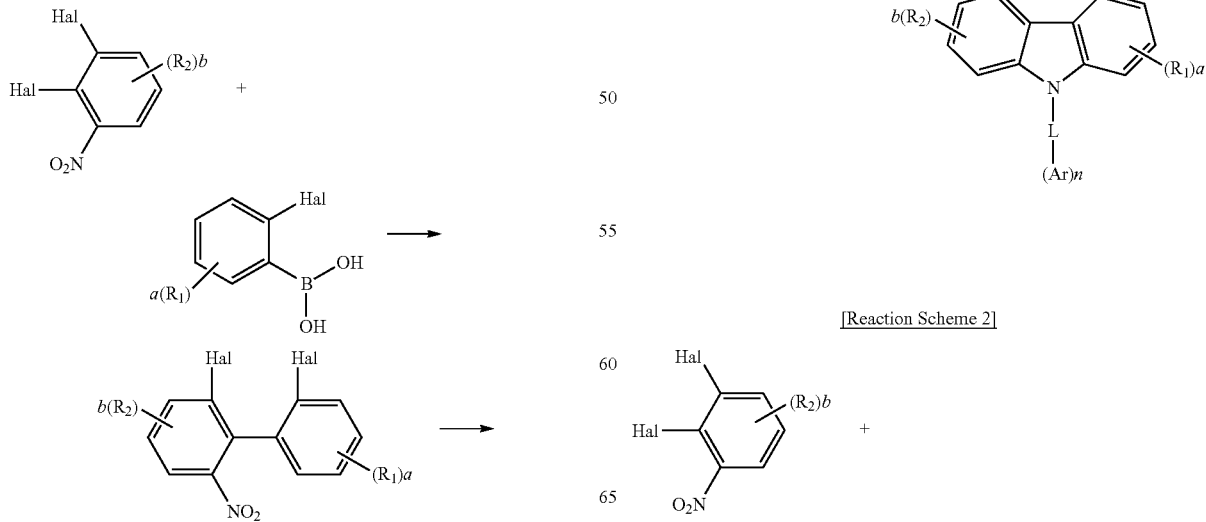
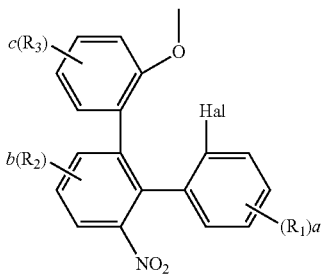
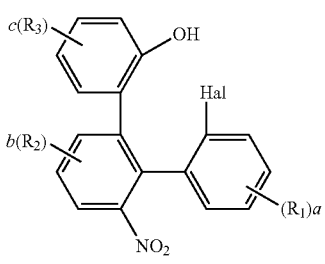
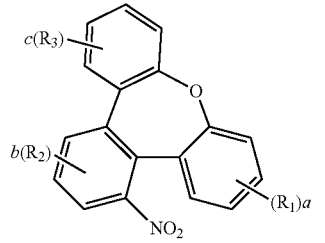
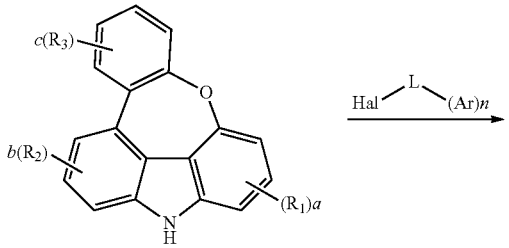
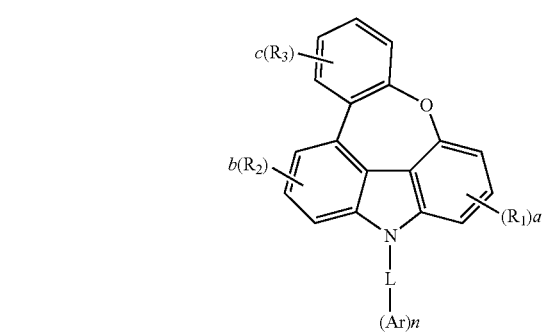
[Reaction Scheme 2]
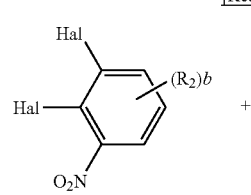

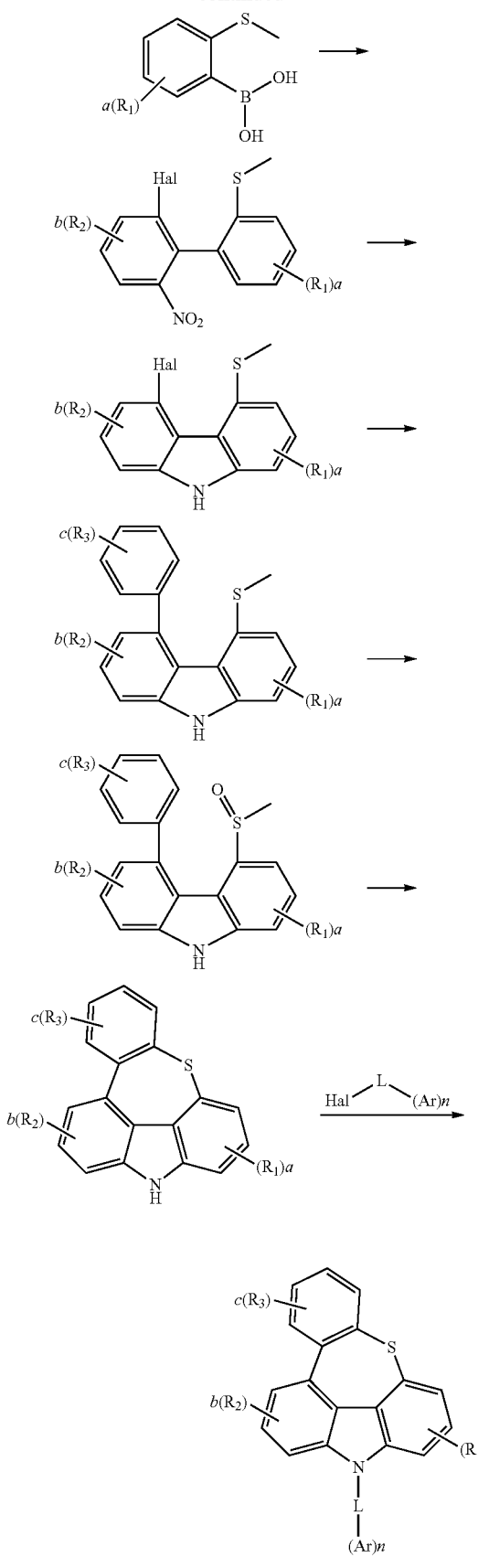
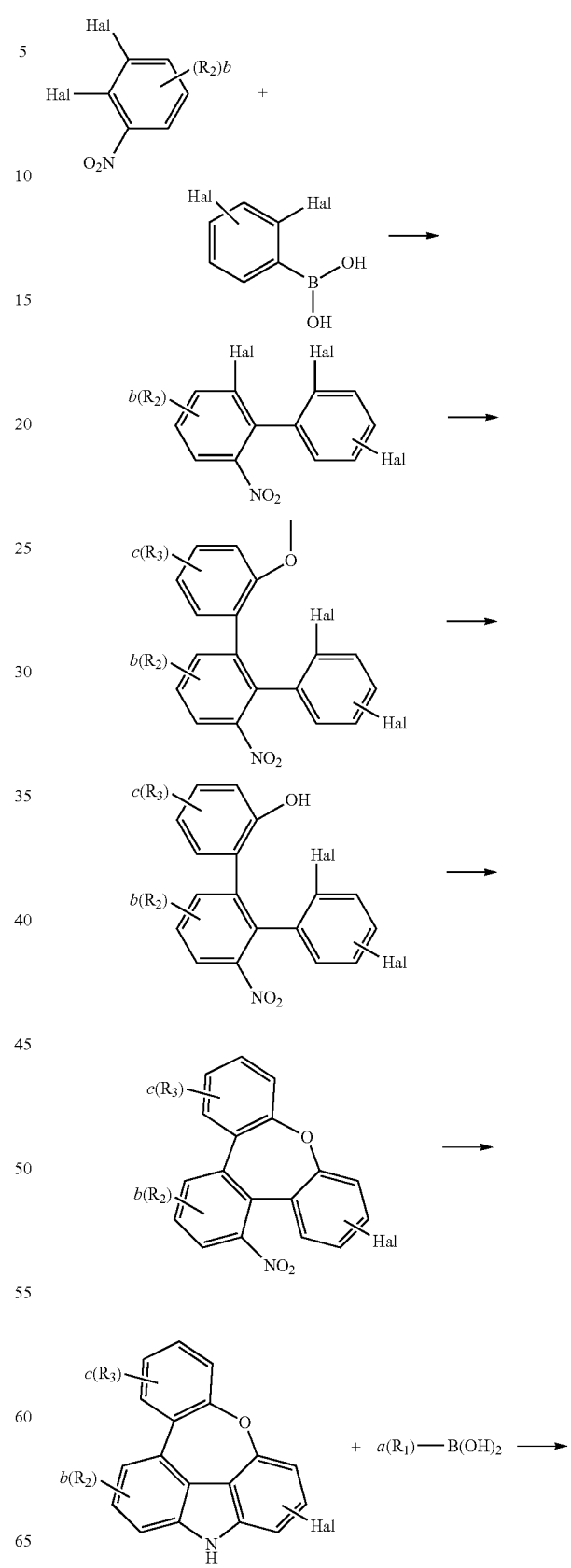
[Reaction Scheme 3]

47
-continued
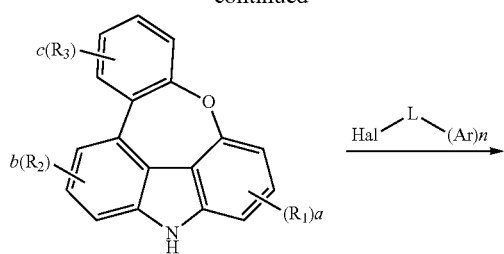
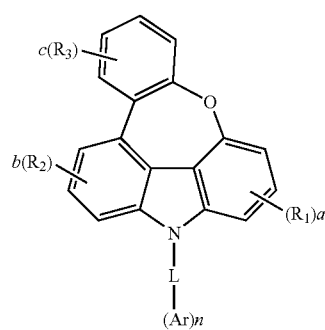
[Reaction Scheme 4]
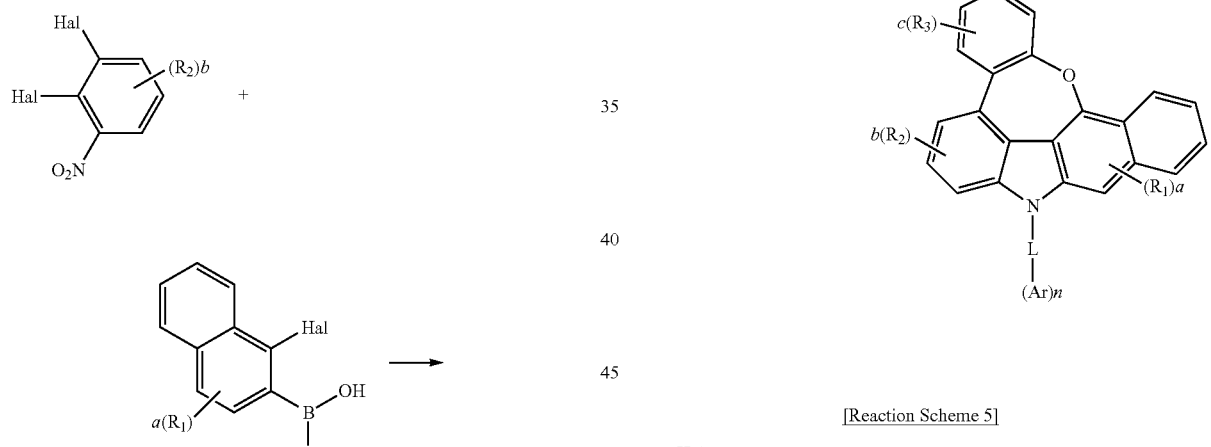
48
-continued
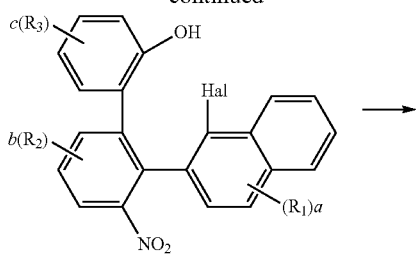
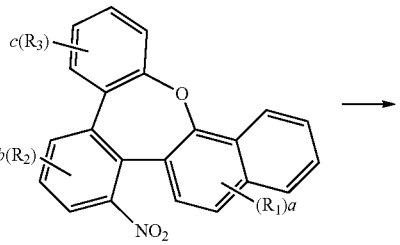
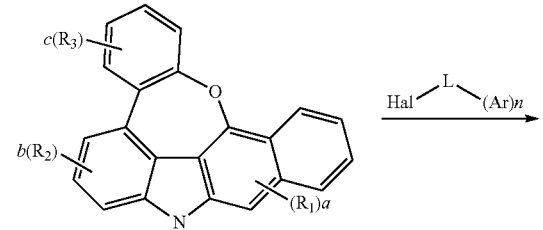
[Reaction Scheme 5]
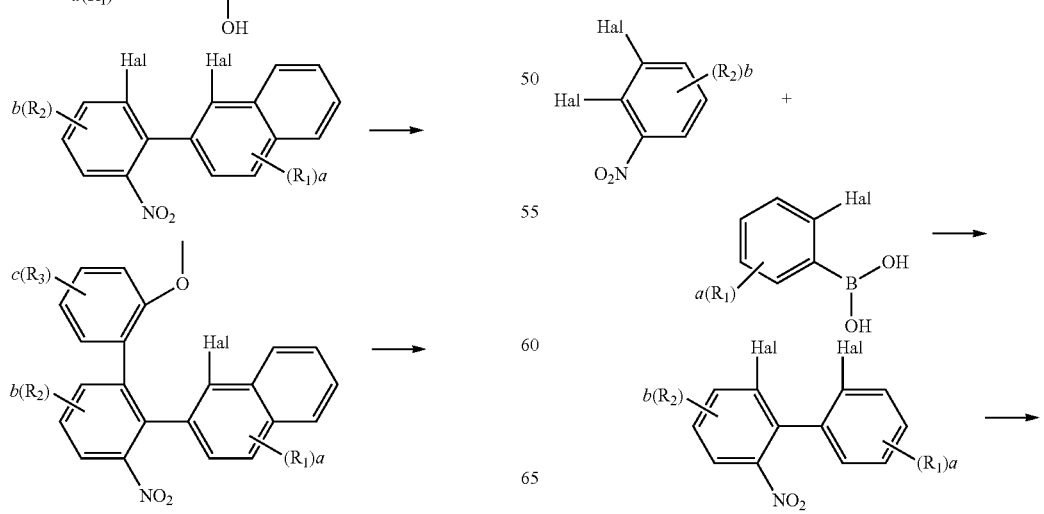

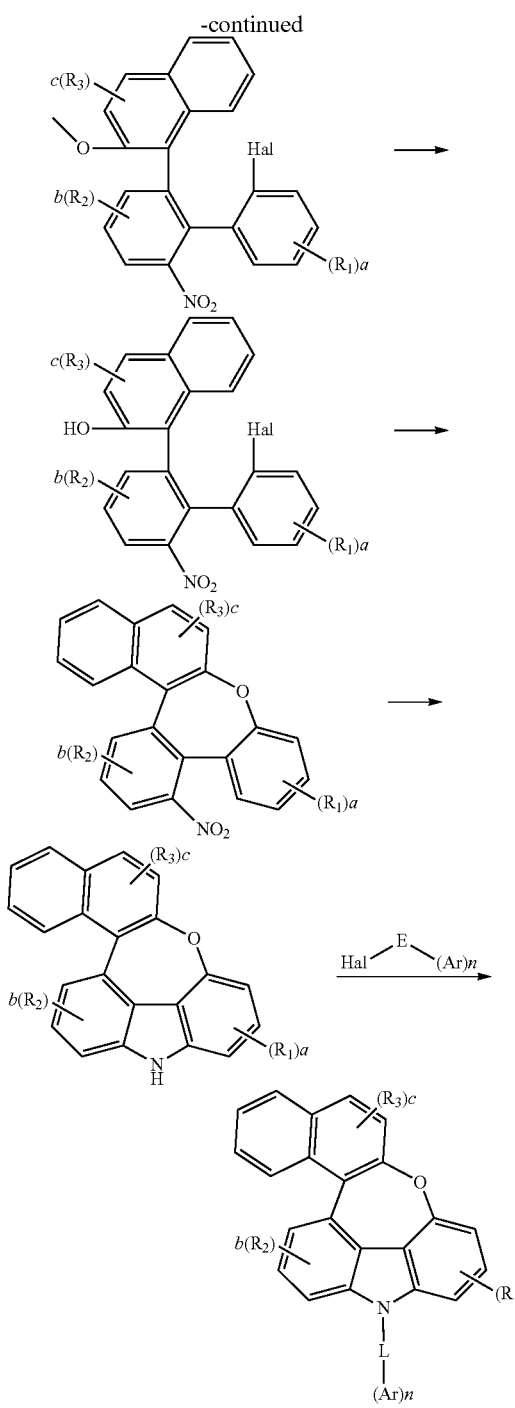

wherein, L, Ar, $R_1$ to $R_3$, n, a, b and c are as defined in formula 1.

The present disclosure also discloses an organic electroluminescent material comprising the compound of formula 1, and an organic electroluminescent device comprising the material.

The organic electroluminescent material may consist of the organic electroluminescent compound of the present disclosure as a sole compound, or may further comprise conventional materials generally used in organic electroluminescent materials.

The organic electroluminescent device of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer. Herein, the hole auxiliary layer or the light-emitting auxiliary layer may be placed between the hole transport layer and the light-emitting layer, which may control a transport rate of a hole. The hole auxiliary layer or the light-emitting auxiliary layer may be effective to produce an organic electroluminescent device having excellent efficiencies and/or improved lifespan.

The organic electroluminescent compound represented by formula 1 may be comprised in the light-emitting layer. When used in the light-emitting layer, the organic electroluminescent compound of formula 1 may be comprised as a host material. Preferably, the light-emitting layer may further comprise at least one dopant. If necessary, another compound besides the organic electroluminescent compound of formula 1 may be further comprised as a second host material. Herein, the weight ratio of the first host material to the second host material is in the range of 1:99 to 99:1. The doping concentration of a dopant compound to a host compound in the light-emitting layer is preferable to be less than 20 wt %.

The second host material can use any of the known phosphorescent hosts. Preferably, the second host material may comprise the compound selected from the group consisting of the compounds represented by the following formulas 11 to 16:

$$H\text{-}(Cz\text{-}L_4)_n\text{-}M \quad (11)$$

$$H\text{-}(Cz)_i\text{-}L_4\text{-}M \quad (12)$$

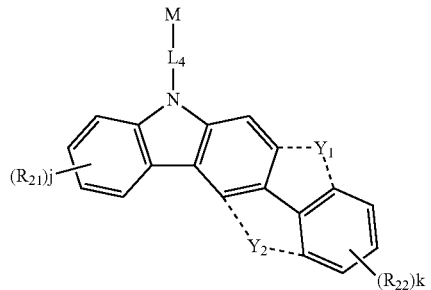

(13)

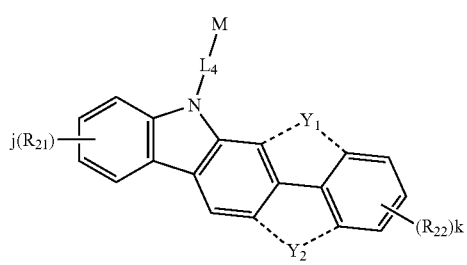

(14)

-continued

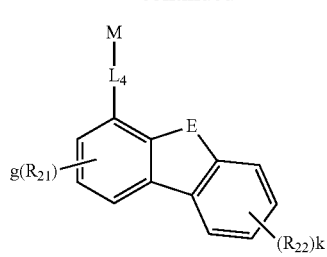
(15)

wherein
Cz represents the following structure:

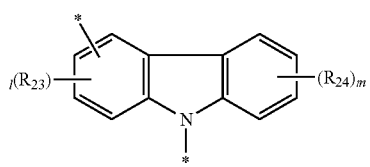

E represents O or S;
R$_{21}$ to R$_{24}$, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, or —SiR$_{25}$R$_{26}$R$_{27}$; in which R$_{25}$ to R$_{27}$, each independently, represent a substituted or unsubstituted (C1-C30)alkyl, or a substituted or unsubstituted (C6-C30)aryl; L$_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered) heteroaryl; Y$_1$ and Y$_2$, each independently, represent O, S, —NR$_{31}$ or —CR$_{32}$R$_{33}$, with the proviso that Y$_1$ and Y$_2$ are not present simultaneously; R$_{31}$ to R$_{33}$, each independently, represent a substituted or unsubstituted (C1-C30)alkyl, a substituted or unsubstituted (C6-C30) aryl, or a substituted or unsubstituted (5- to 30-membered)heteroaryl; R$_{32}$ and R$_{33}$ may be the same or different; h and i, each independently, represent an integer of 1 to 3; g represents an integer of 0 to 3; j, k, l and m, each independently, represent an integer of 0 to 4; where if g, h, i, j, k, l and m, each independently, represent an integer of 2 or more, each (Cz-L$_4$), each (Cz), each R$_{21}$, each R$_{22}$, each R$_{23}$ and each R$_{24}$ may be the same or different.

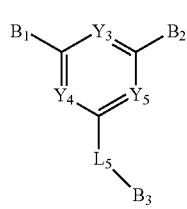
(16)

wherein
Y$_3$ to Y$_5$, each independently, represent CR$_{34}$ or N, in which R$_{34}$ represents hydrogen, a substituted or unsubstituted (C1-C30)alkyl, a substituted or unsubstituted (C6-C30)aryl, or a substituted or unsubstituted (5- to 30-membered)heteroaryl;

B$_1$ and B$_2$, each independently, represent hydrogen, a substituted or unsubstituted (C6-C30)aryl, or a substituted or unsubstituted (5- to 30-membered)heteroaryl;
B$_3$ represents a substituted or unsubstituted (C6-C30)aryl, or a substituted or unsubstituted (5- to 30-membered) heteroaryl;
L$_5$ represents a single bond, a substituted or unsubstituted (C6-C30)arylene, or a substituted or unsubstituted (5- to 30-membered)heteroarylene.

Specifically, the preferred examples of the second host material are as follows:

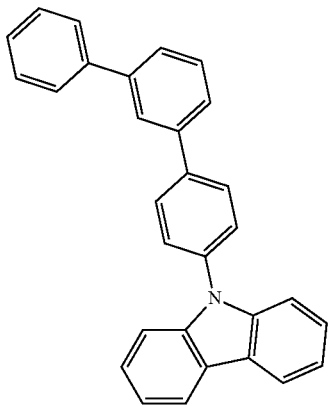
B-1

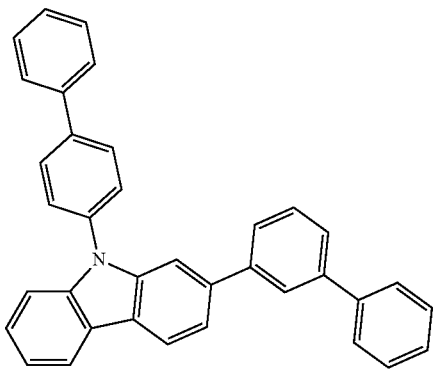
B-2

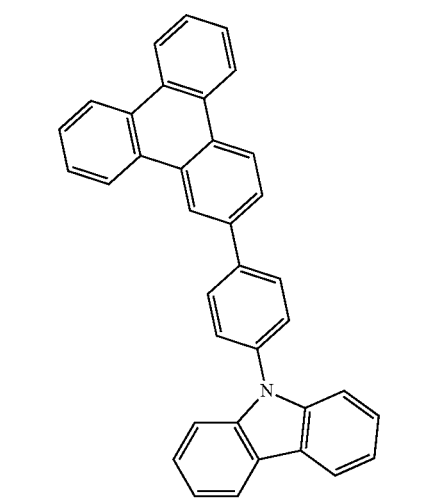
B-3

B-4
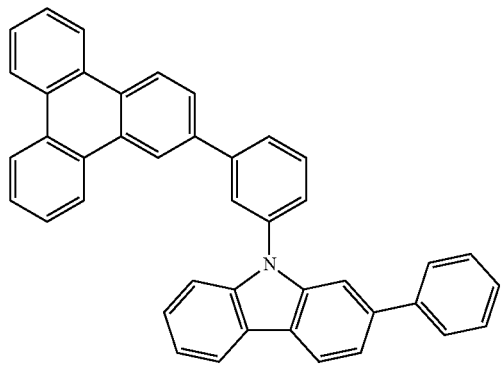
B-5
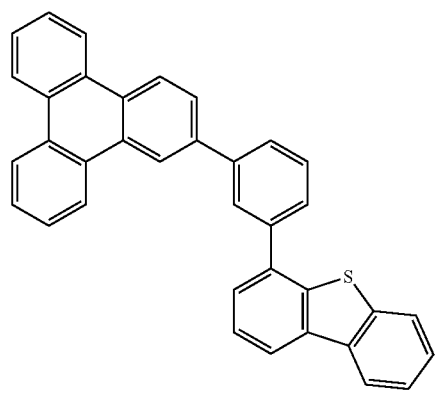
B-6
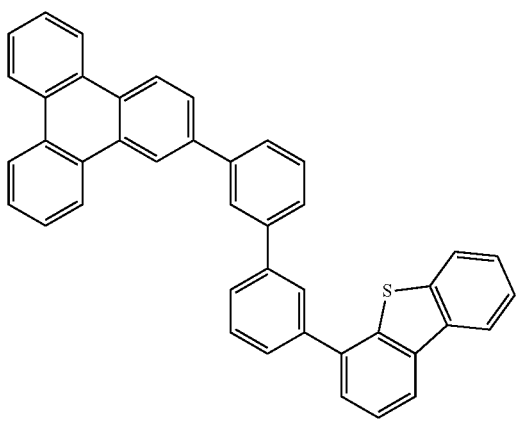
B-7
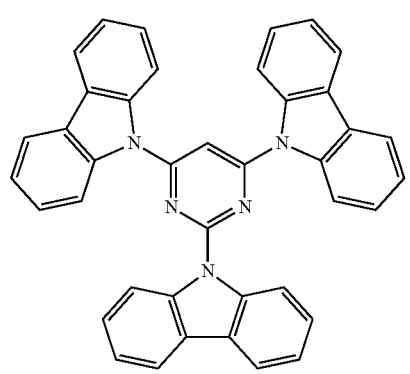
B-8
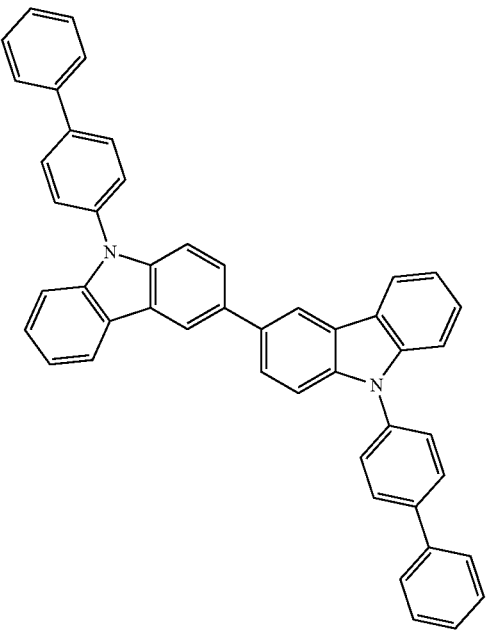
B-9
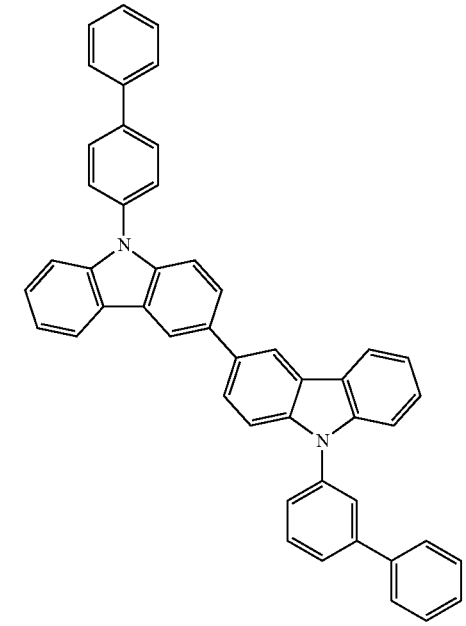

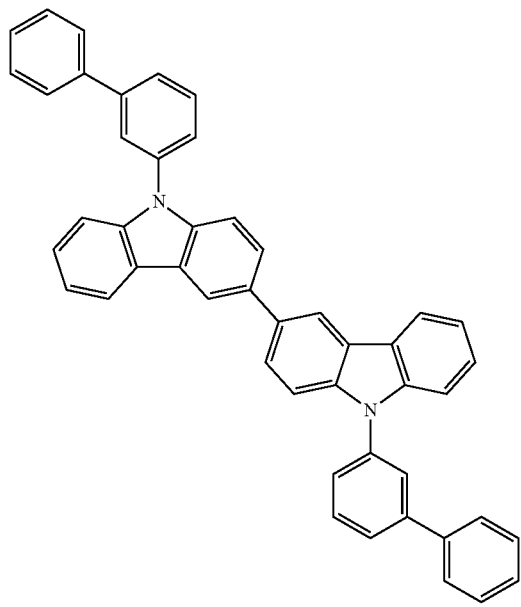
B-10
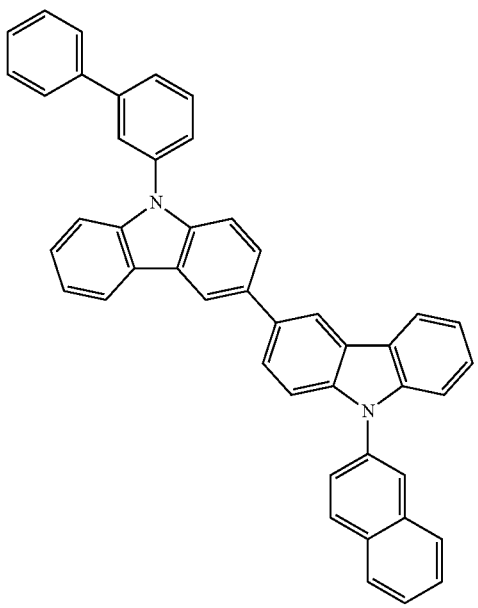
B-12
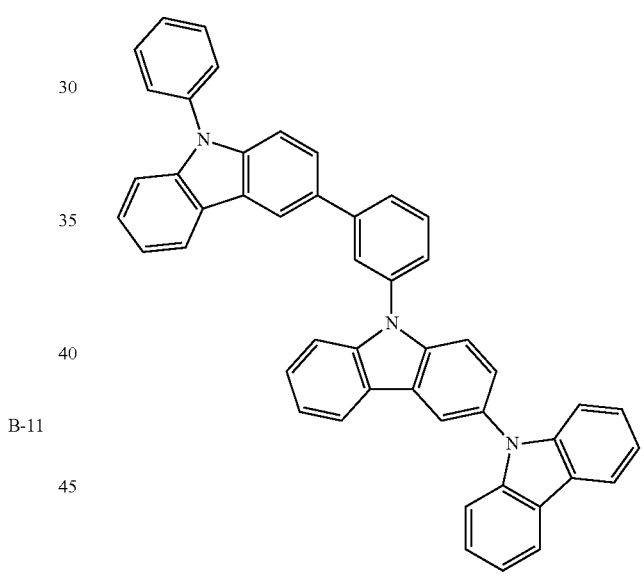
B-13
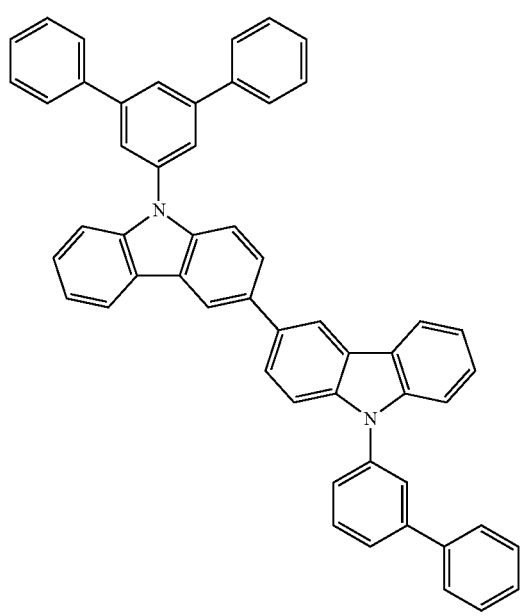
B-11
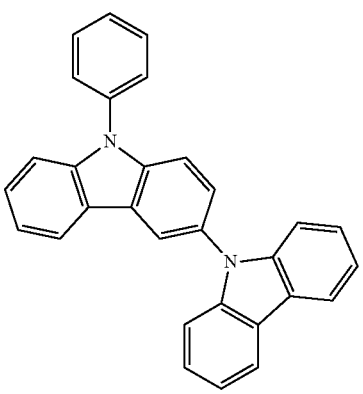
B-14

B-15
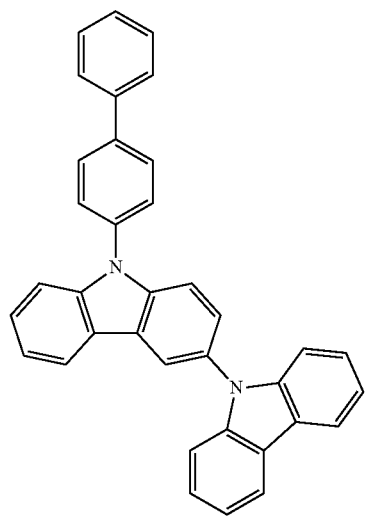
B-16
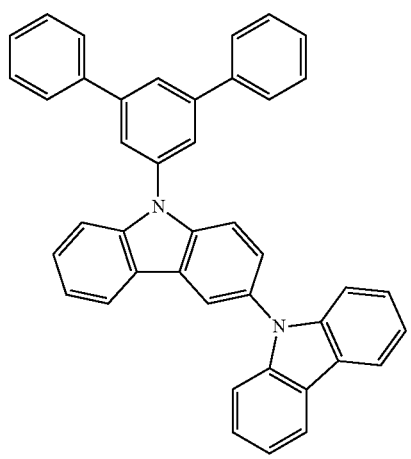
B-17
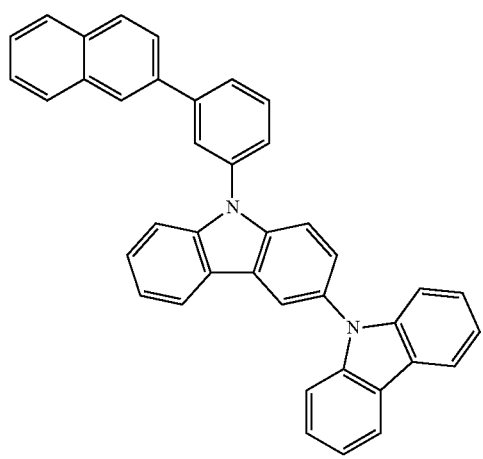
B-18
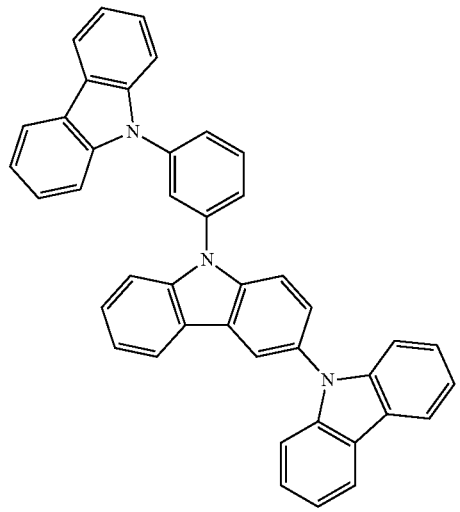
B-19
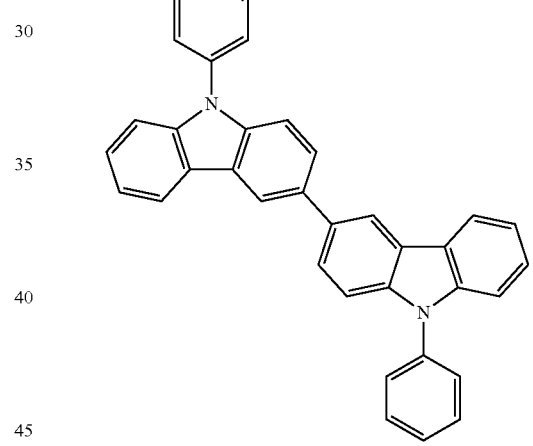
B-20
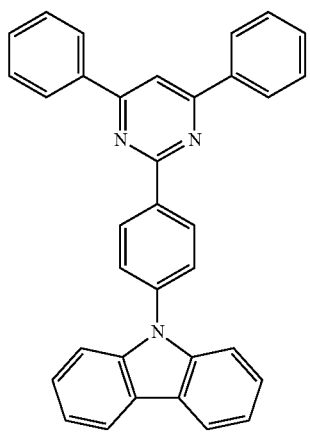

B-21
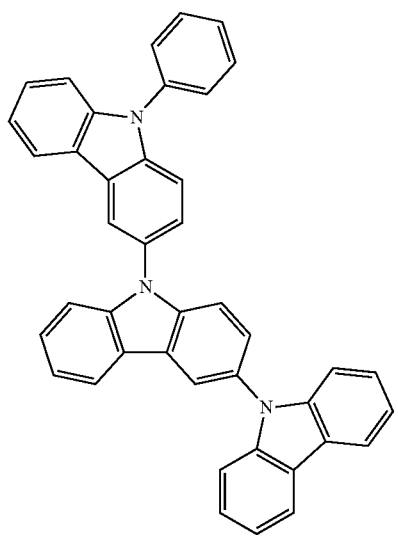
B-23
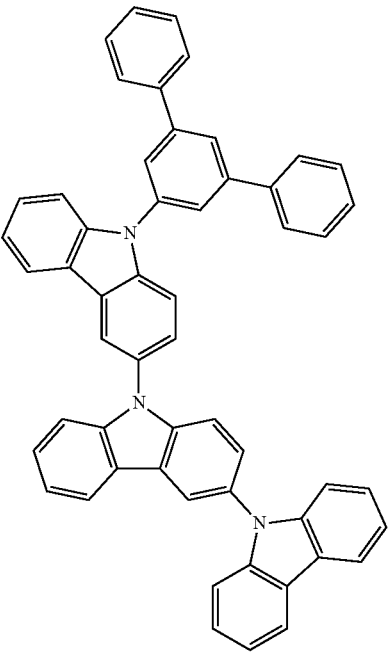
B-22
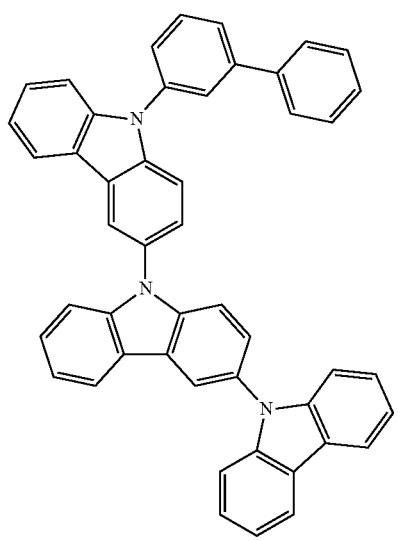
B-24
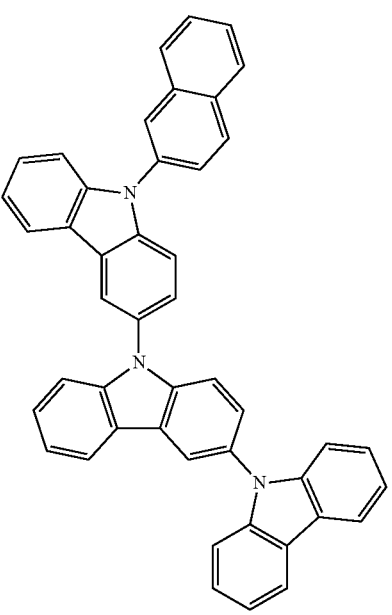

B-25
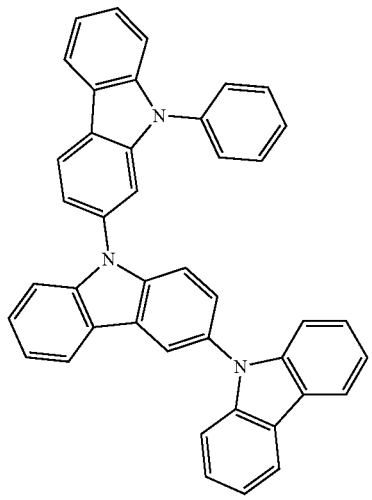
B-26
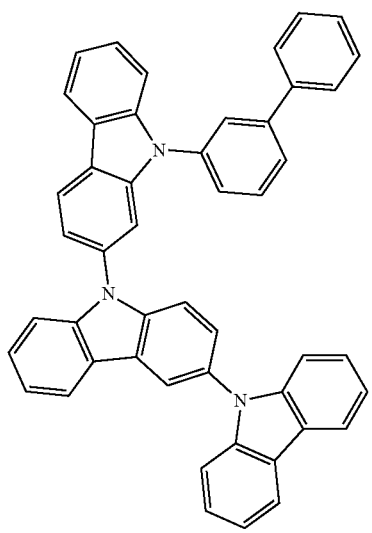
B-27
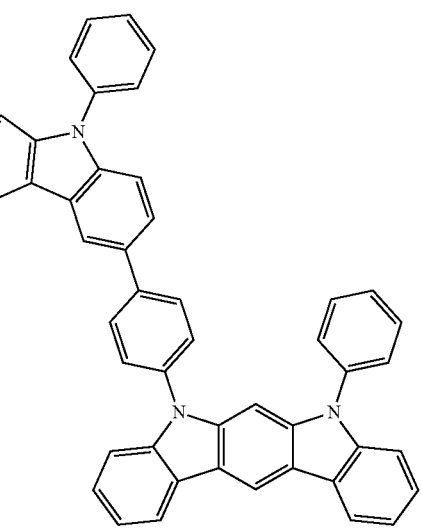
B-28
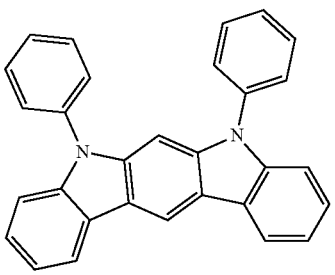
B-29
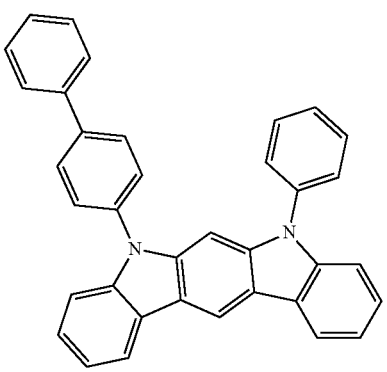
B-30
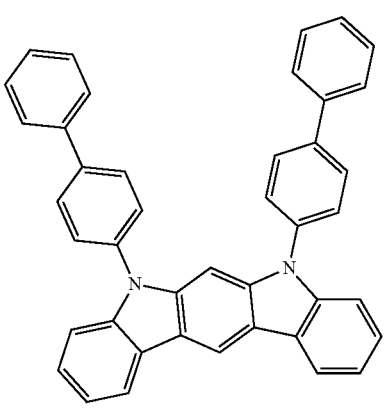
B-31
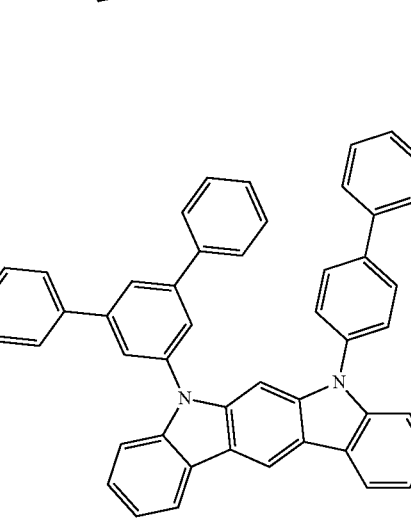

B-32
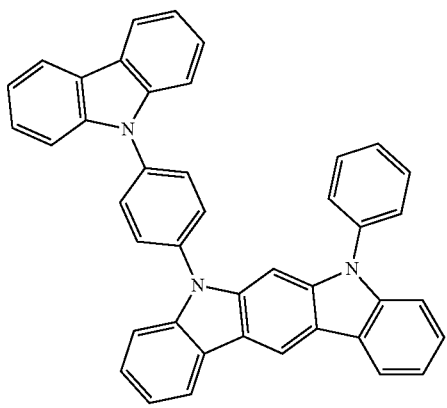
B-33
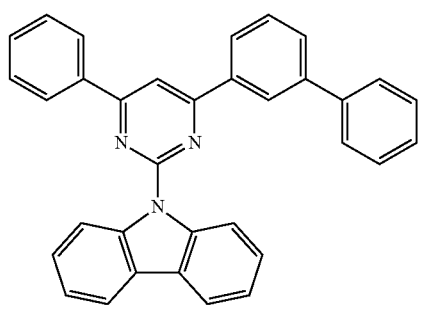
B-34
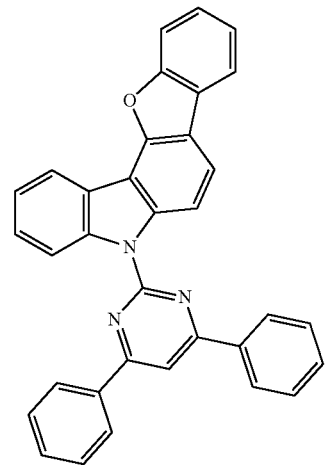
B-35
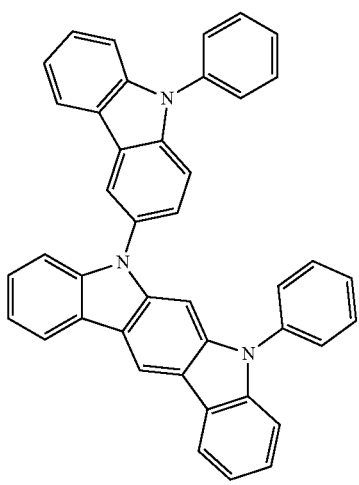
B-36
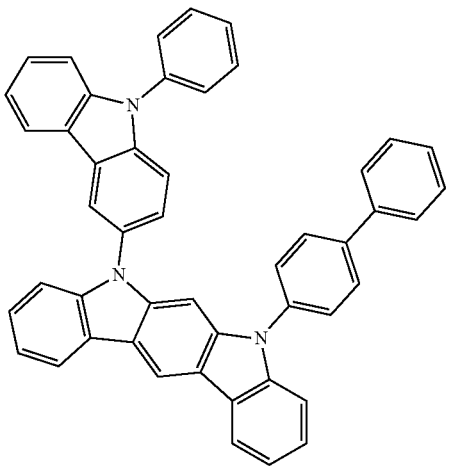
B-37
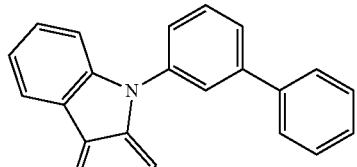
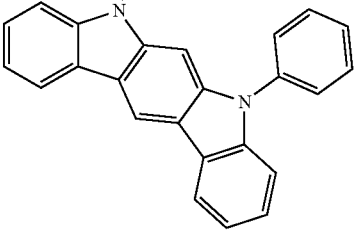
B-38
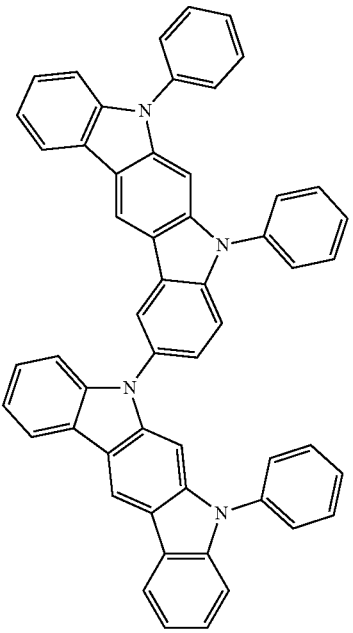

B-39
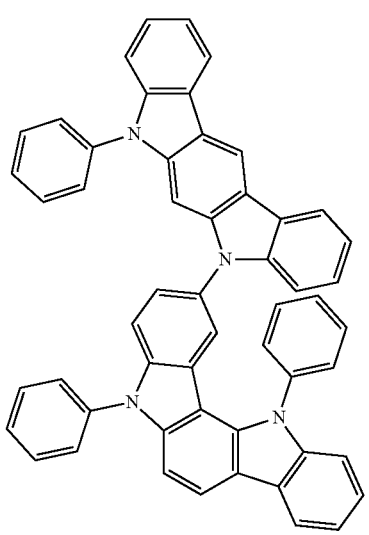
B-40
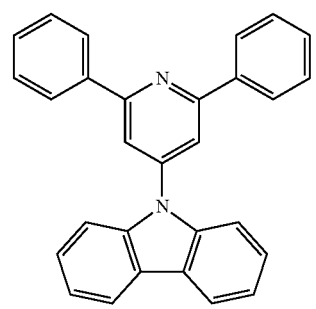
B-41
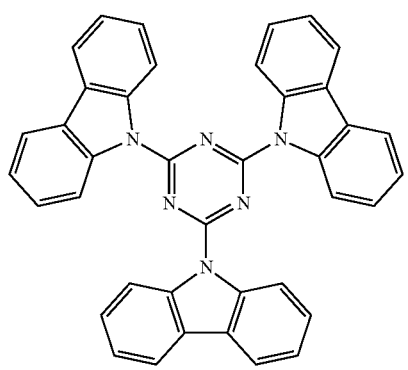
B-42
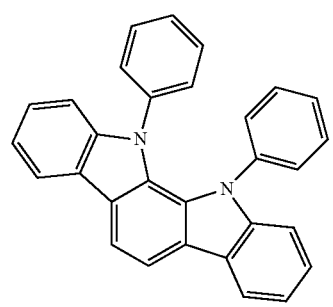
B-43
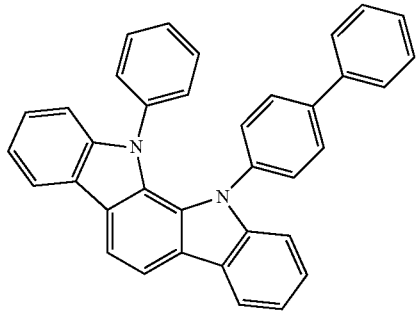
B-44
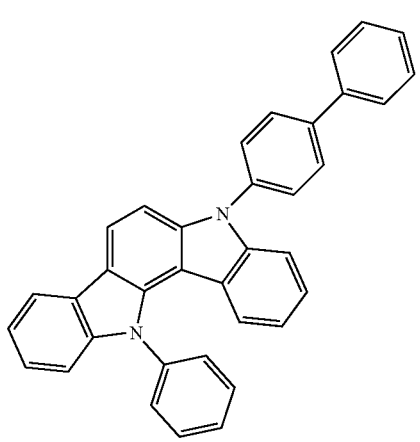
B-45
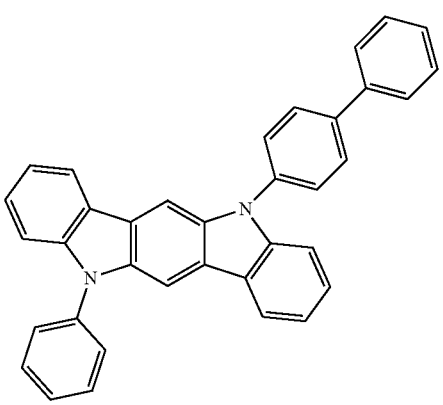
B-46
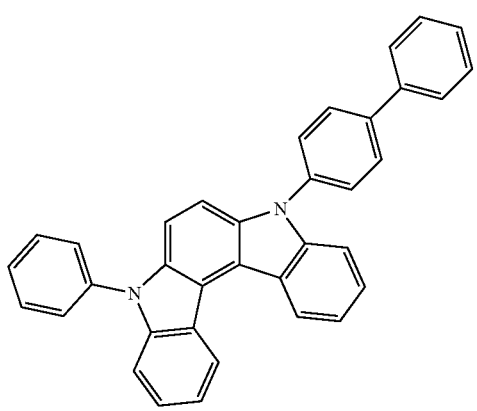

-continued
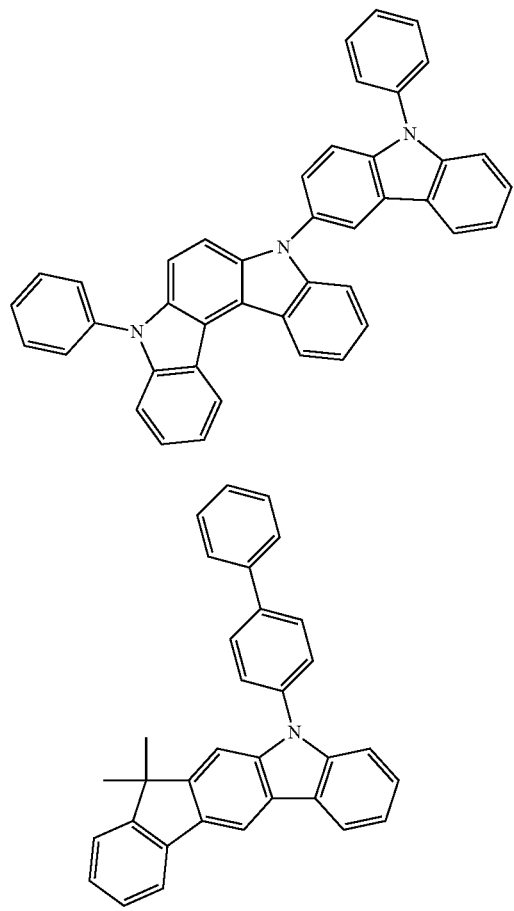
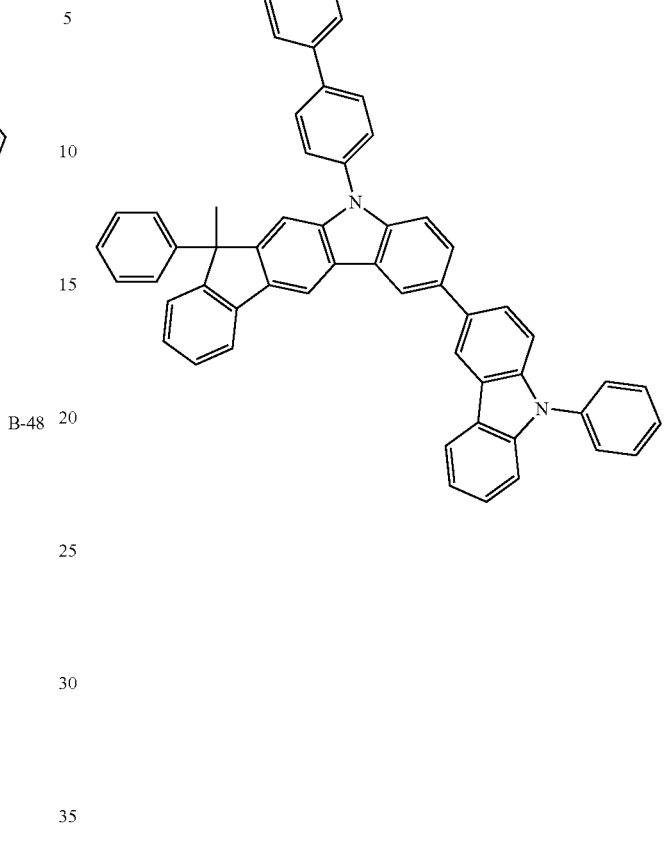
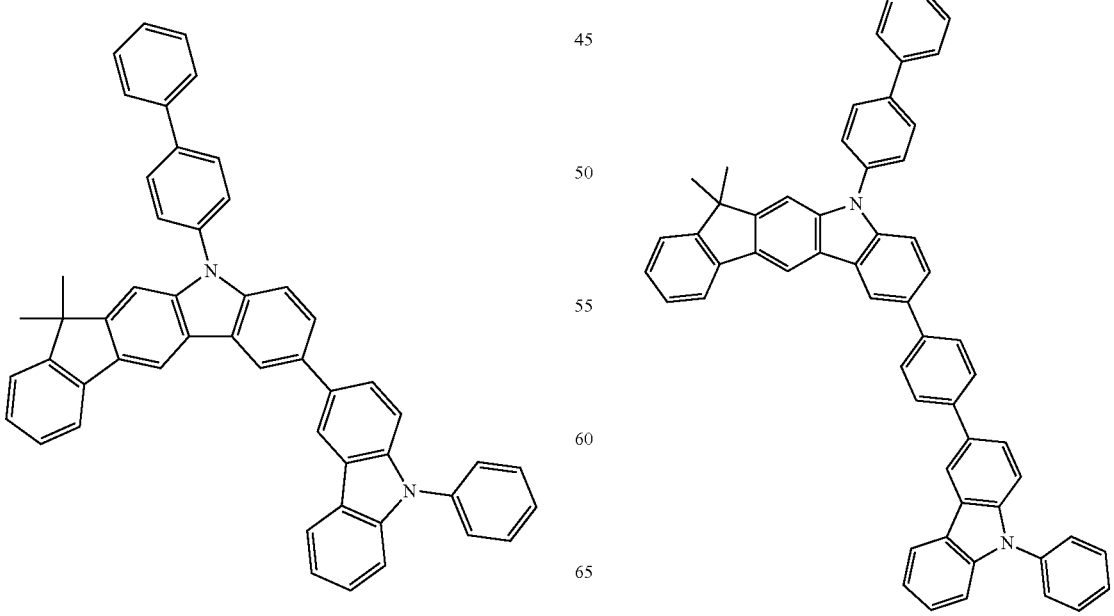

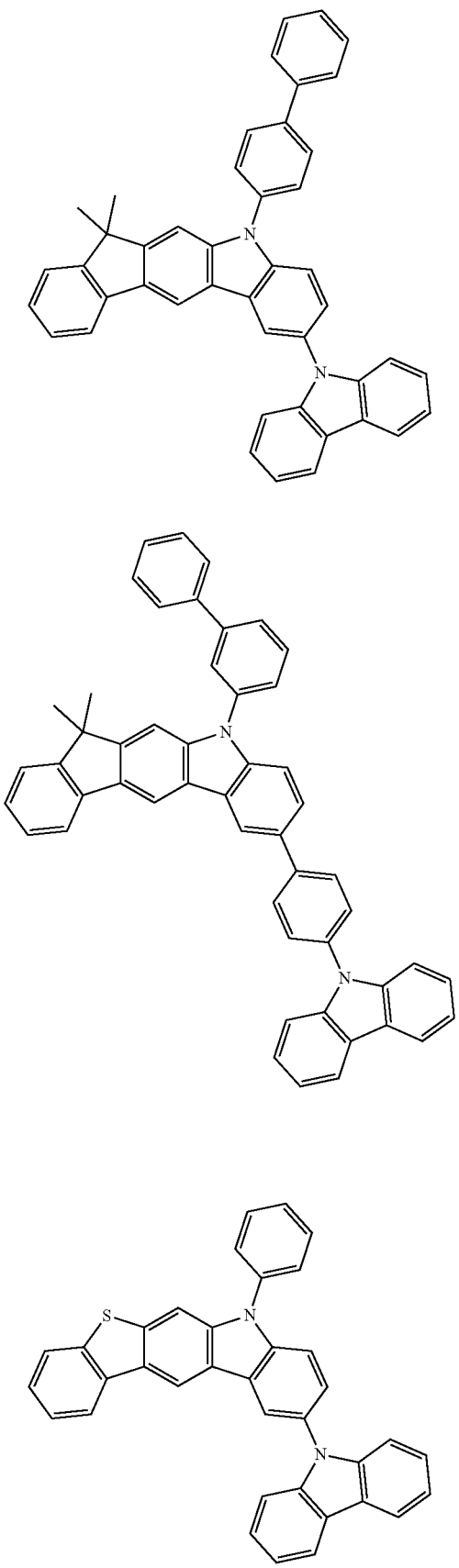
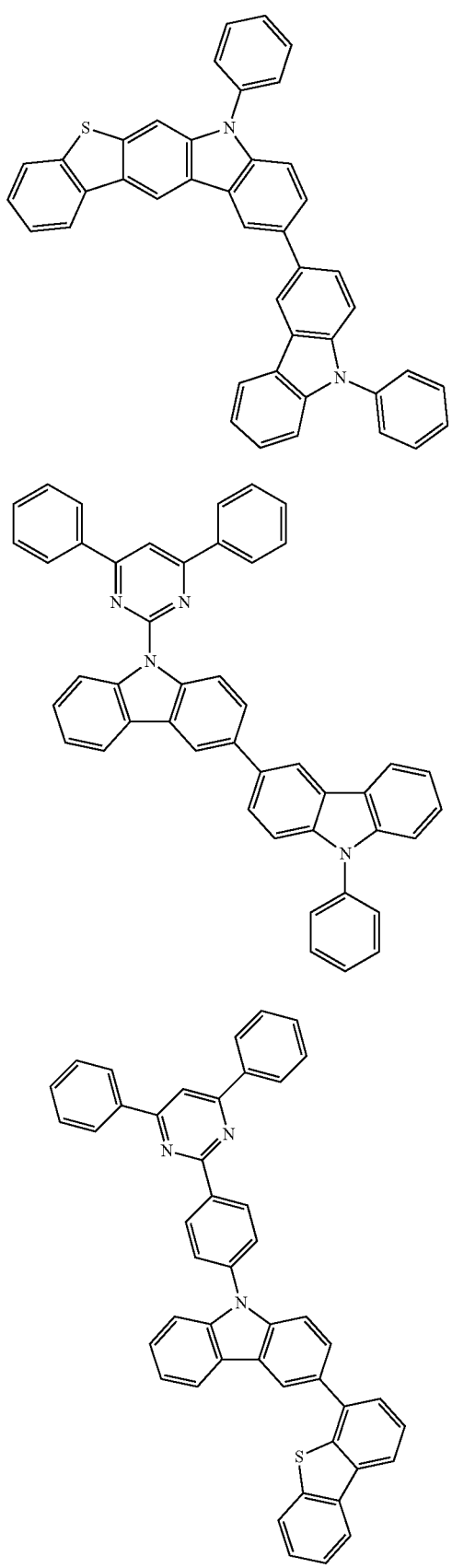

B-58
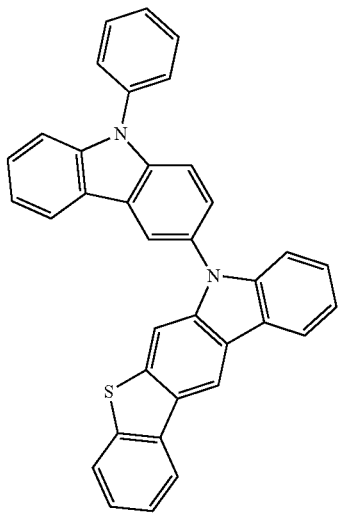
B-61
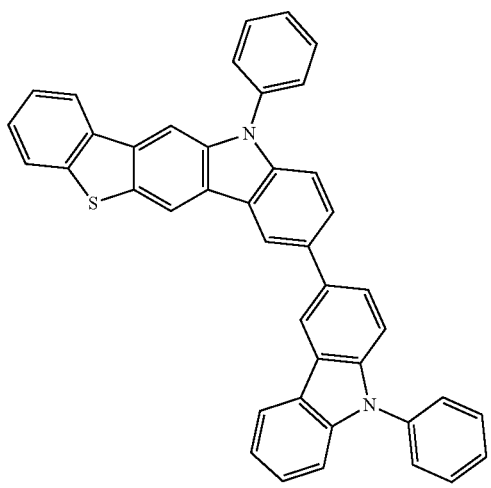
B-59
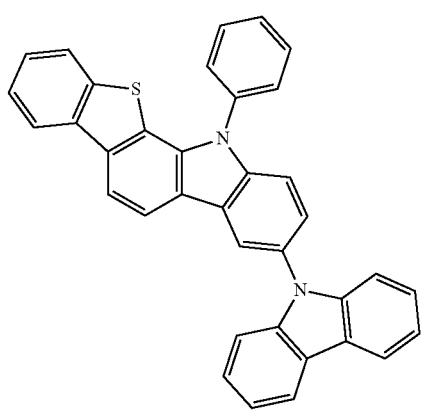
B-62
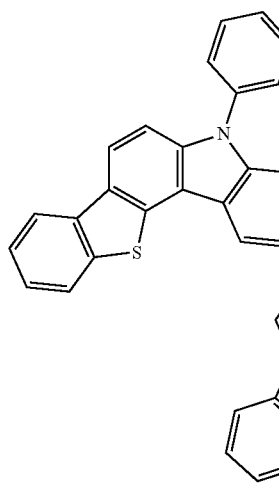
B-60
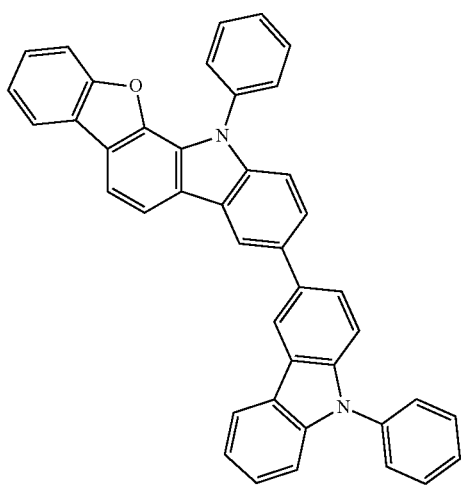
B-63
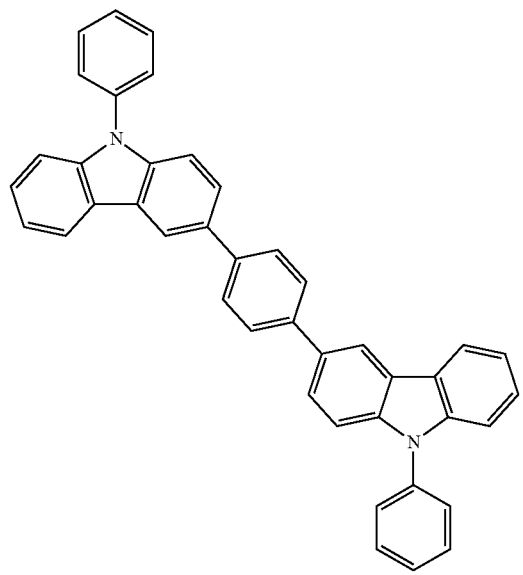

B-64
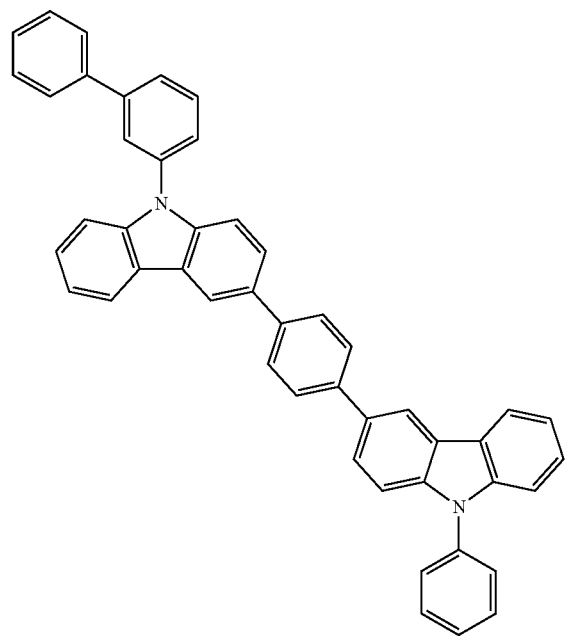
B-65
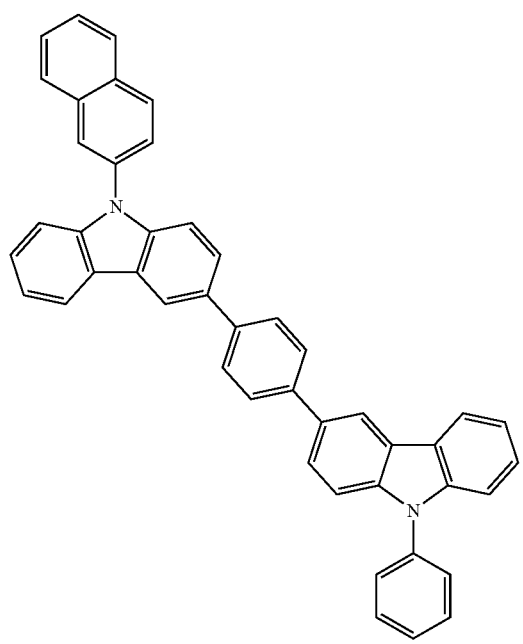
B-66
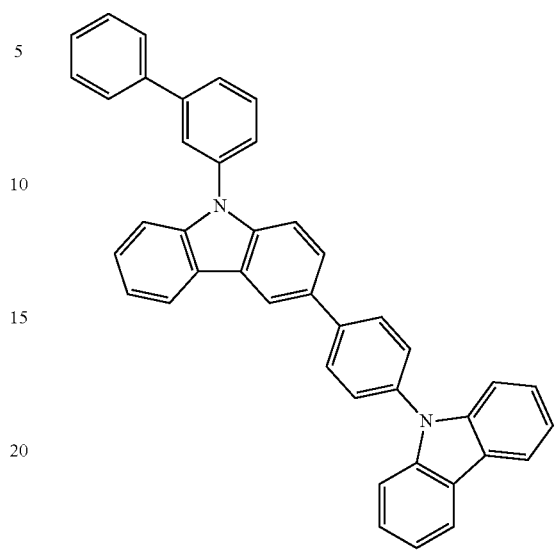
B-67
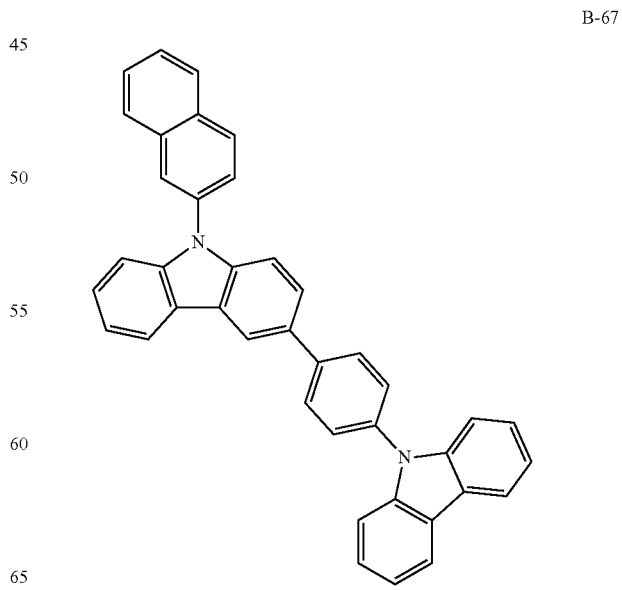

-continued
B-68
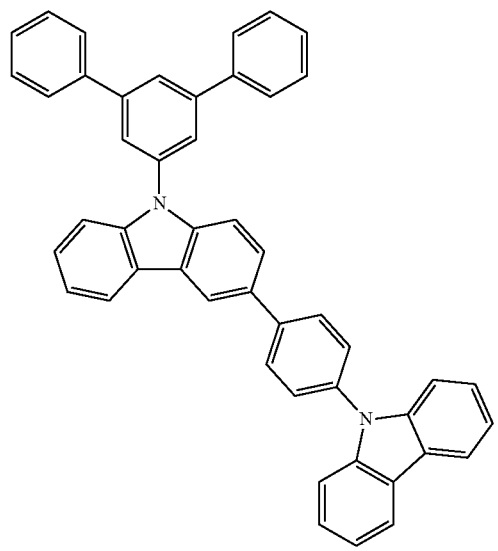
B-70
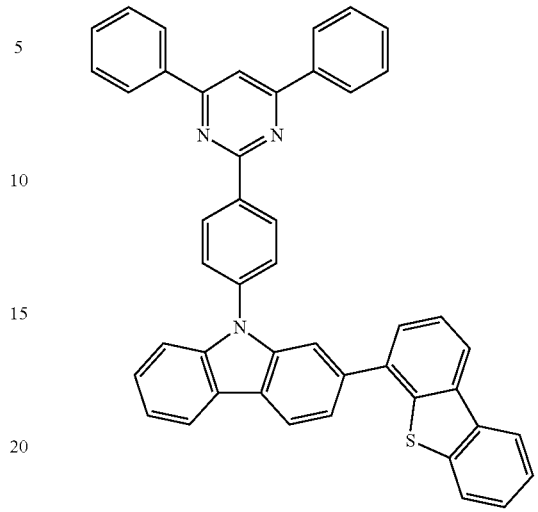
B-71
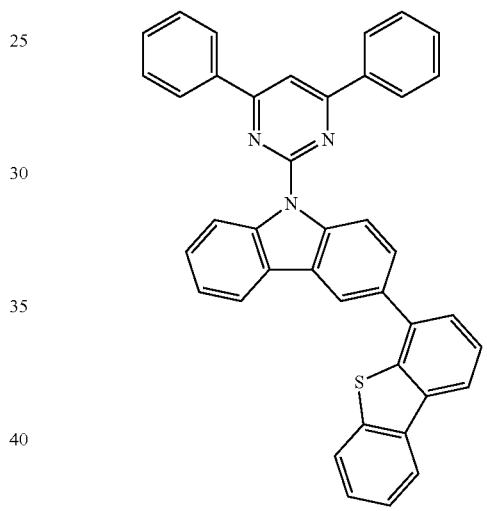
B-69
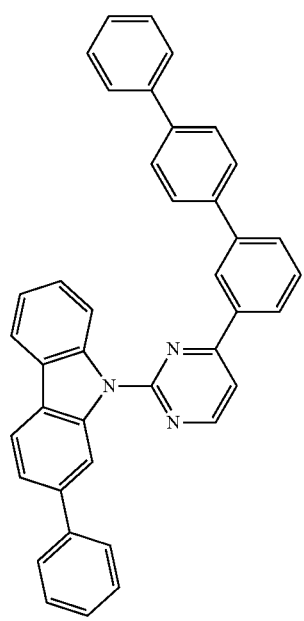
B-72
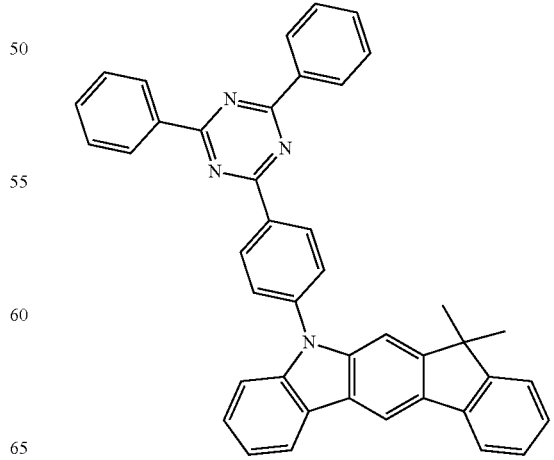

B-73
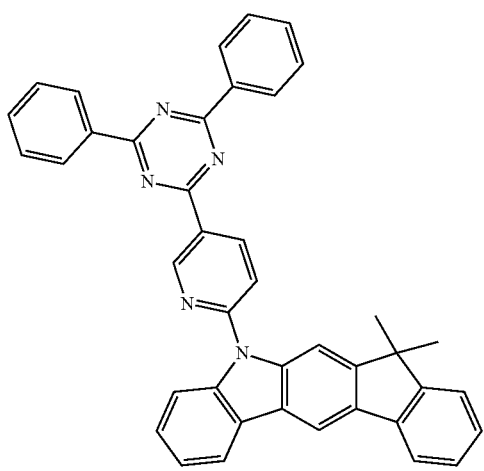
B-74
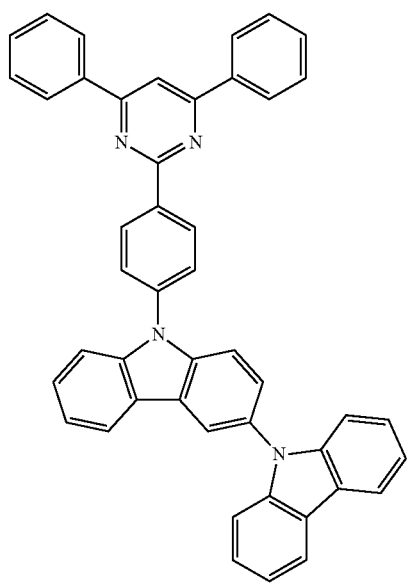
B-75
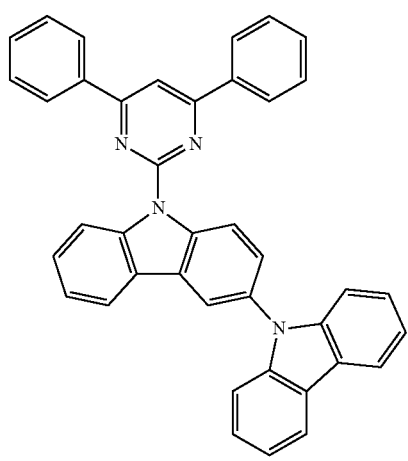
B-76
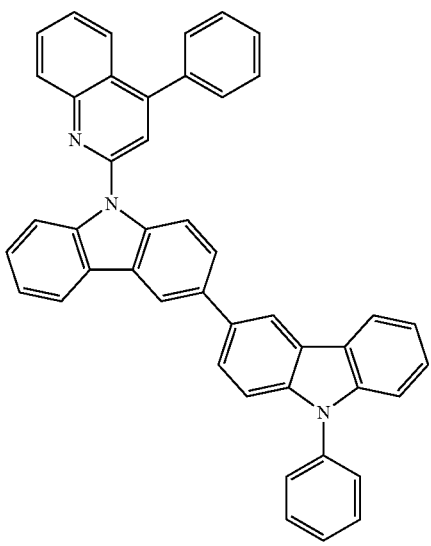
B-77
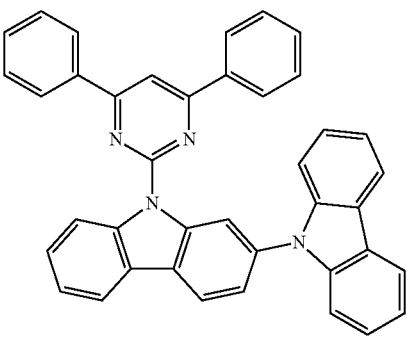
B-78
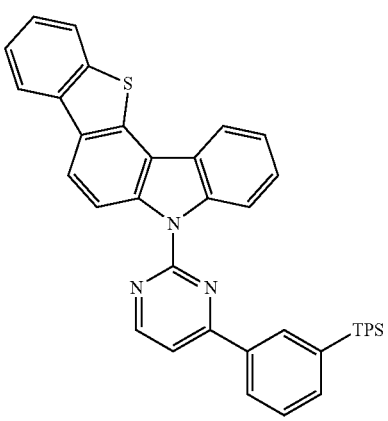

B-79
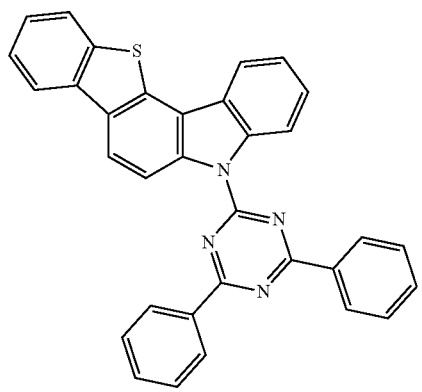
B-80
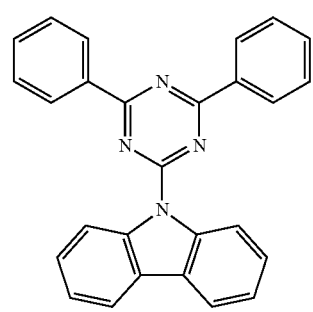
B-81
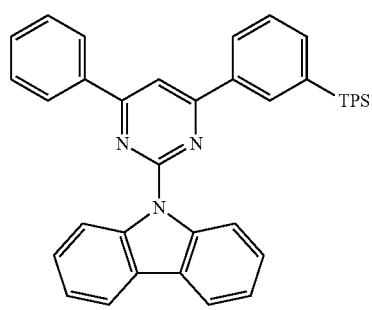
B-82
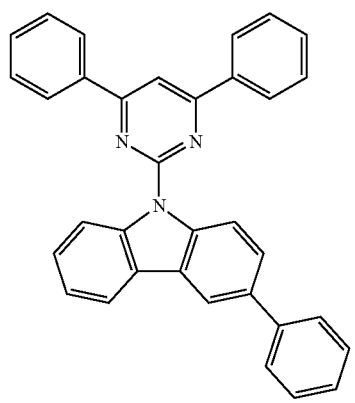
B-83
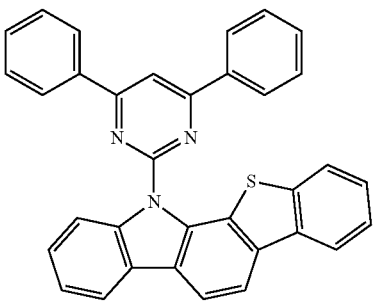
B-84
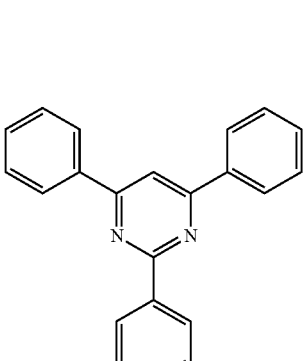
B-85

B-86
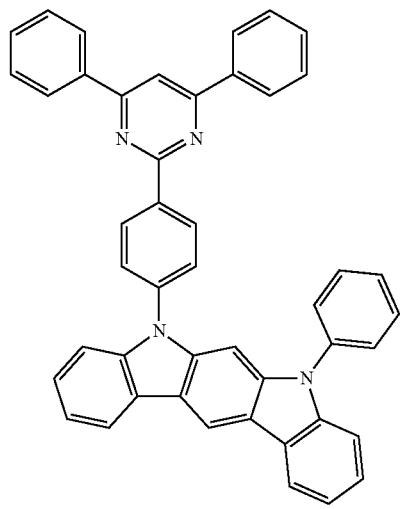
B-87
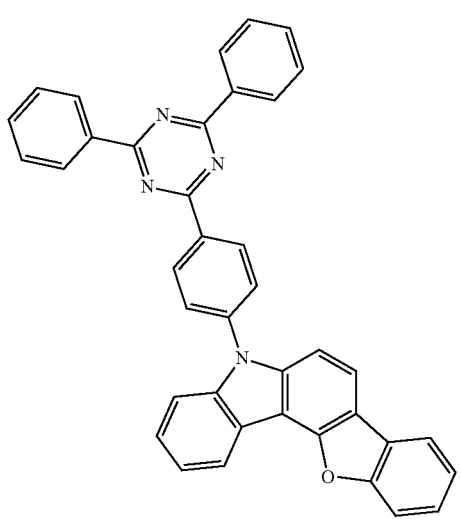
B-88
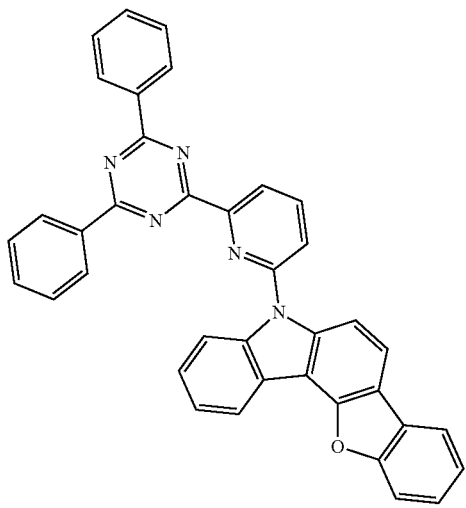
B-89
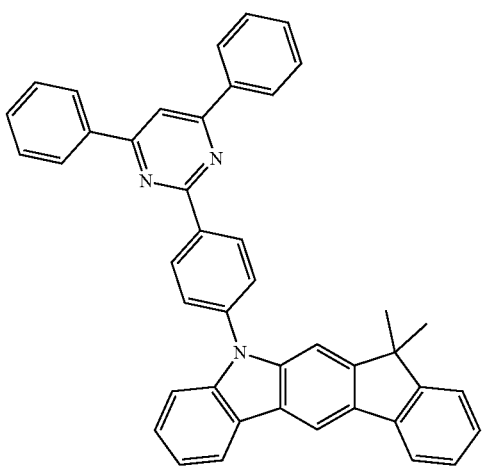
B-90
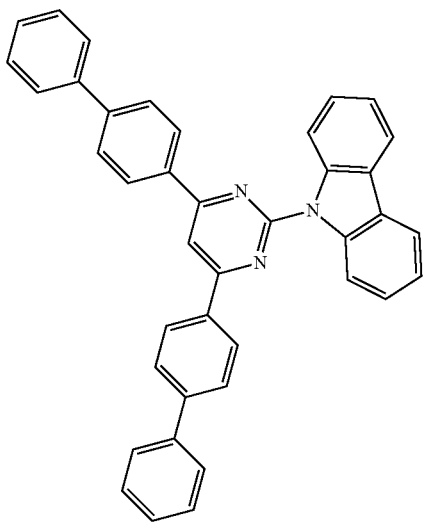
B-91
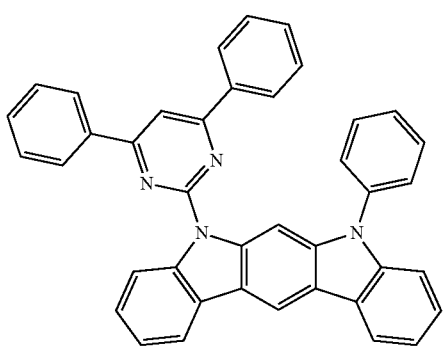

B-92
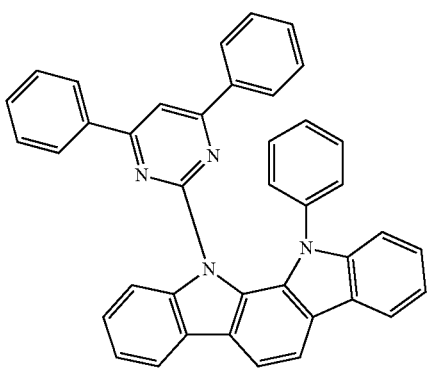
B-93
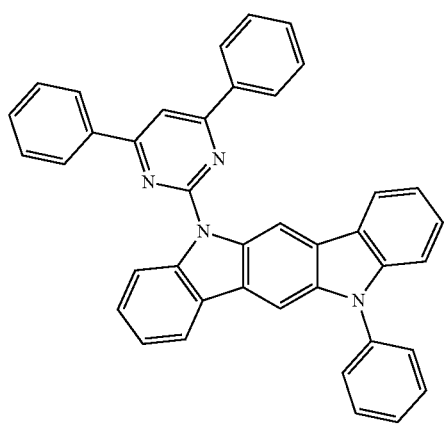
B-94
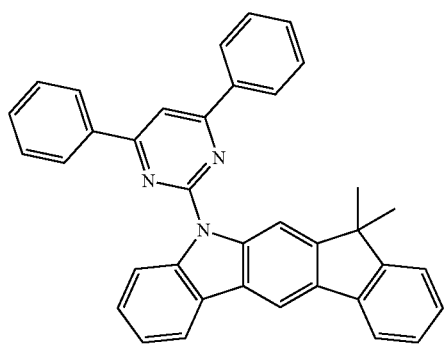
B-95
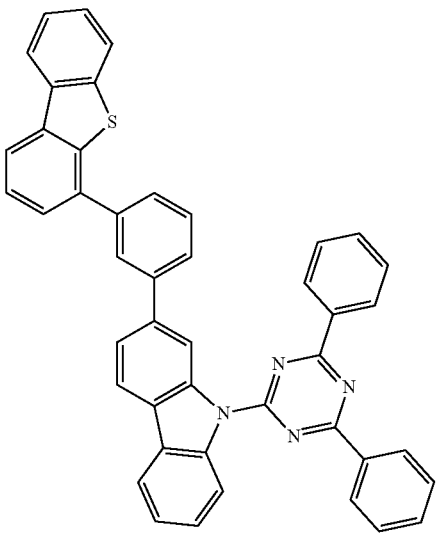
B-96
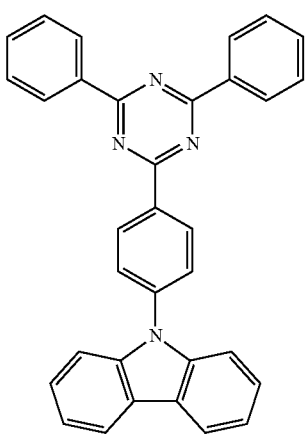
B-97
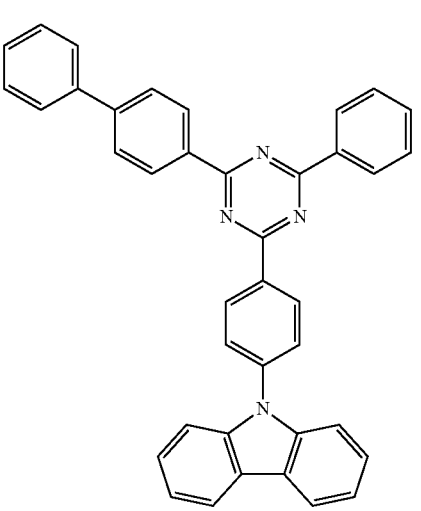

B-98
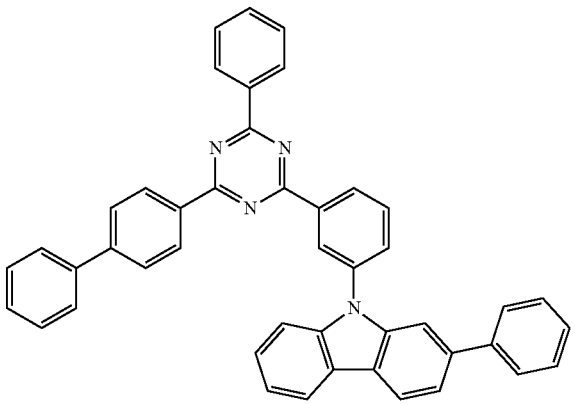
B-99
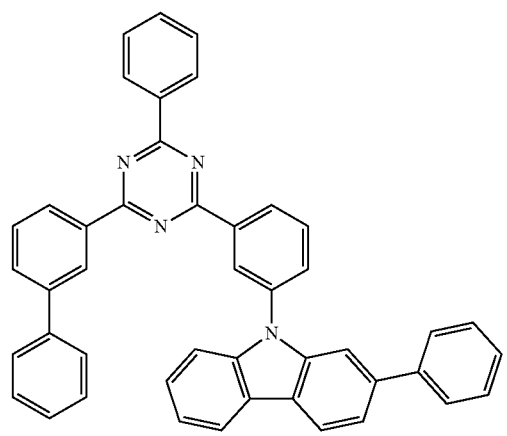
B-100
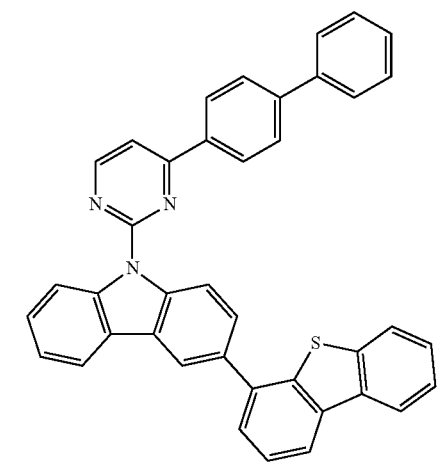
B-101
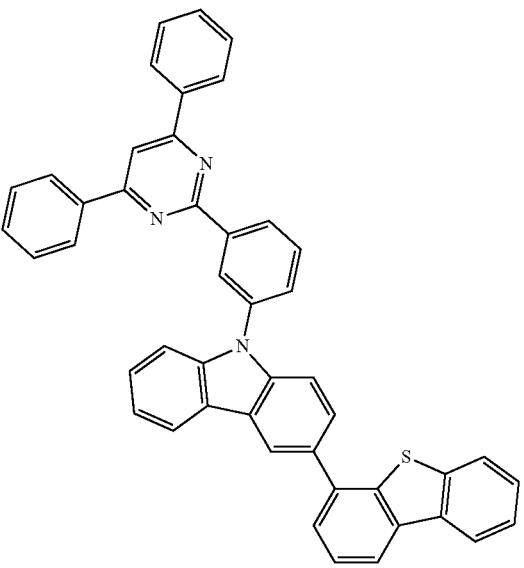
B-102
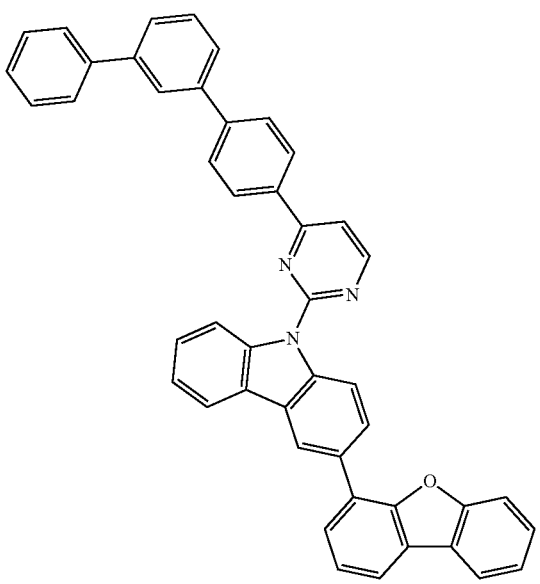

-continued
B-103
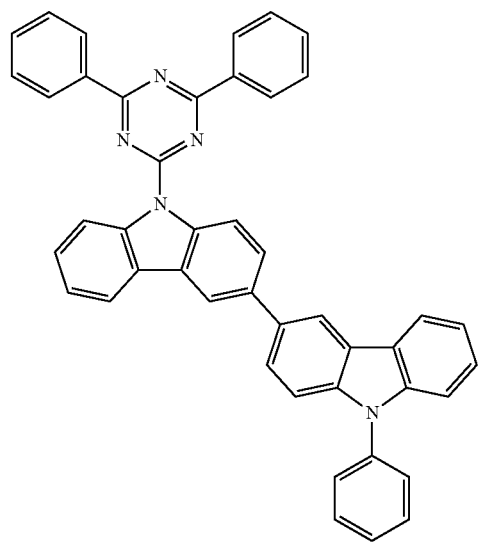
B-104
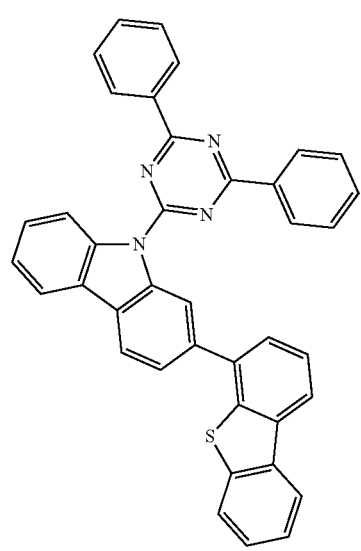
B-105
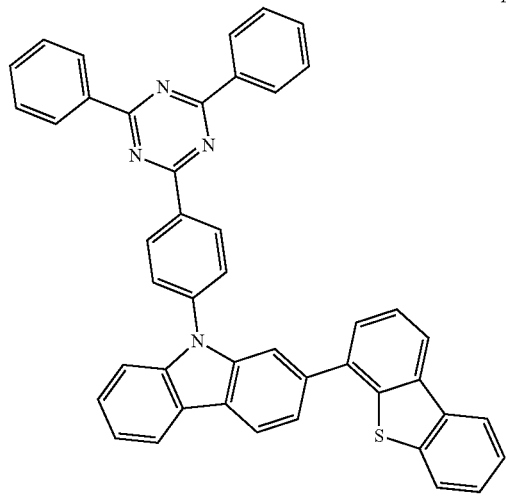
-continued
B-106
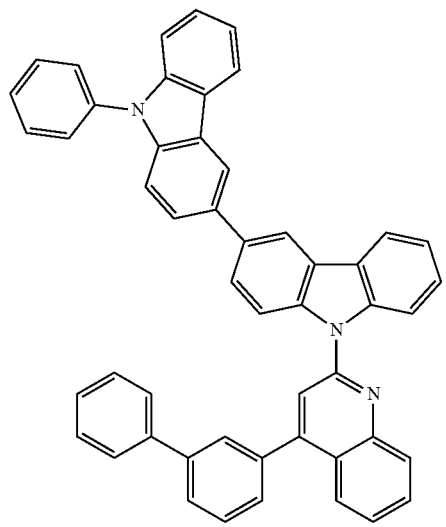
B-107
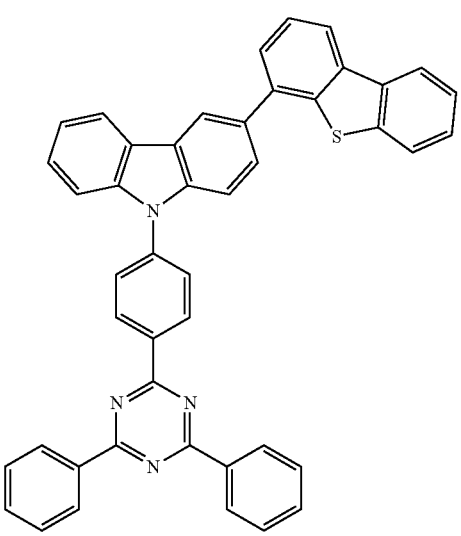
B-108
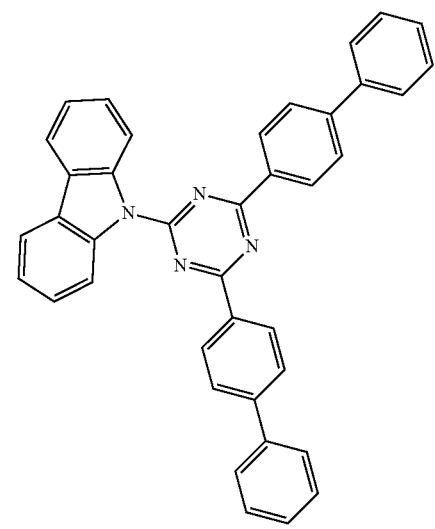

B-109
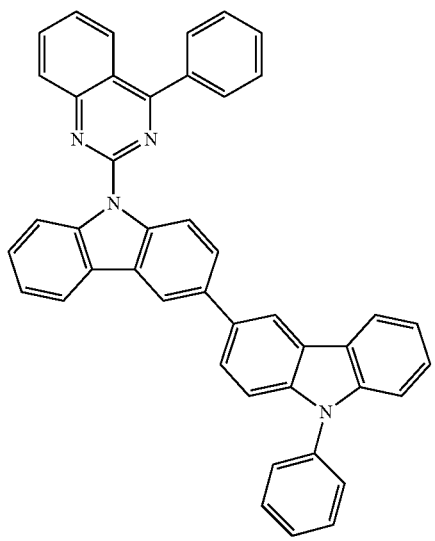
B-110
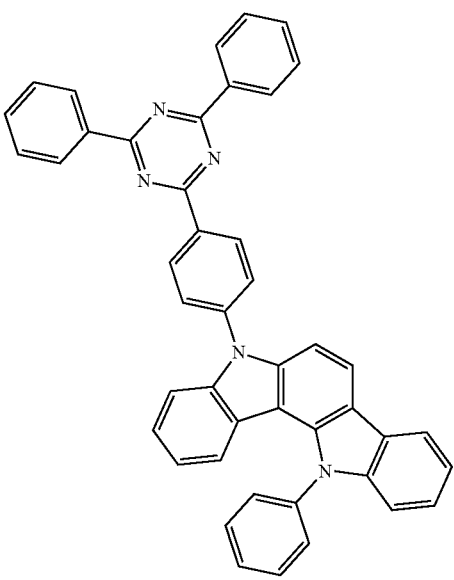
B-111
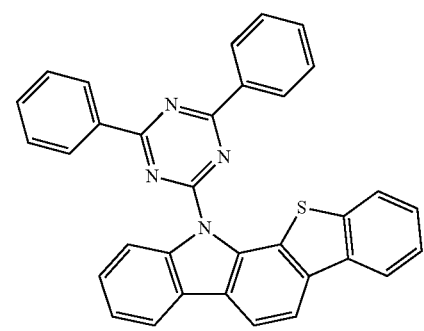
B-112
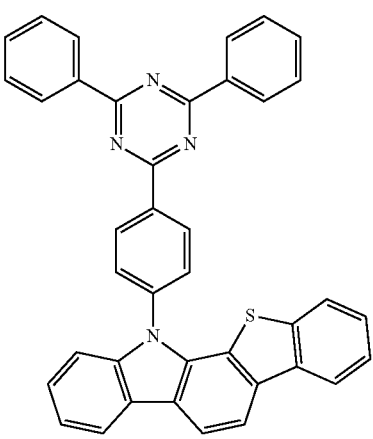
B-113
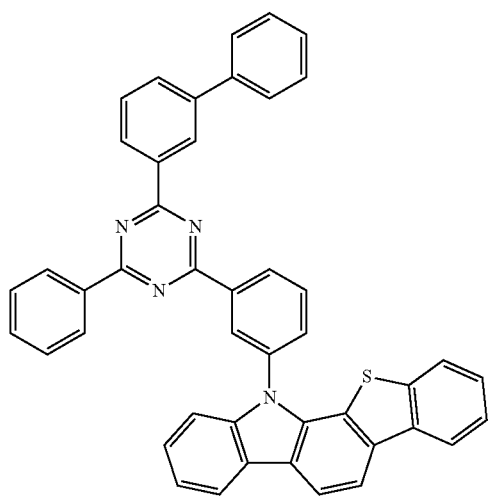
B-114
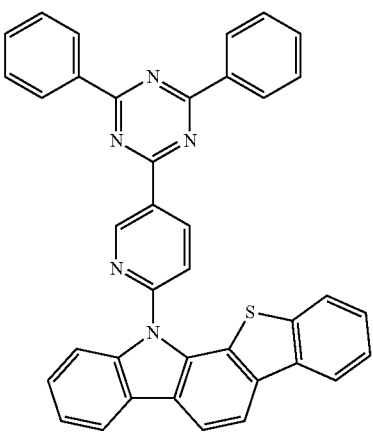

B-115
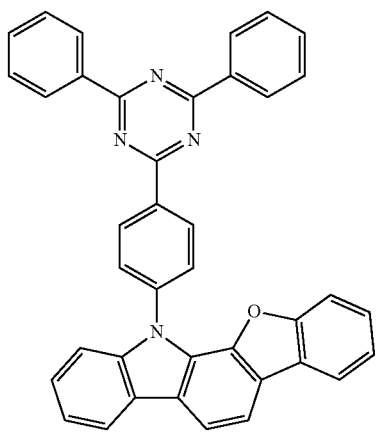
B-116
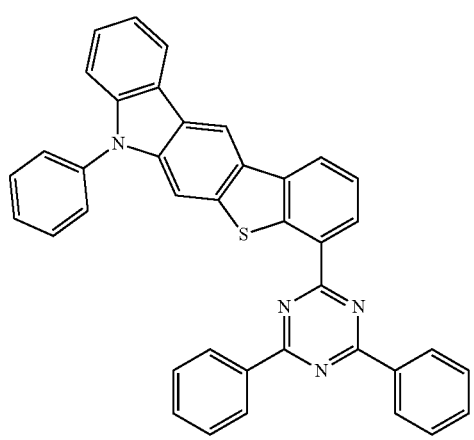
B-117
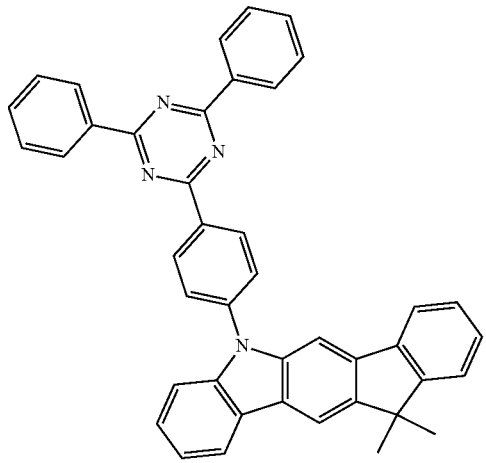
B-118
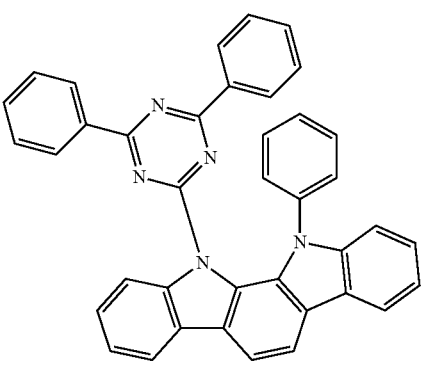
B-119
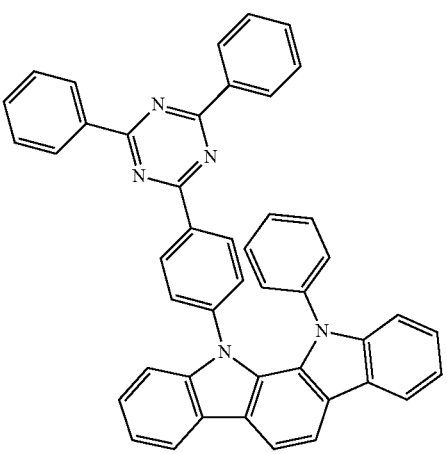
B-120

B-121
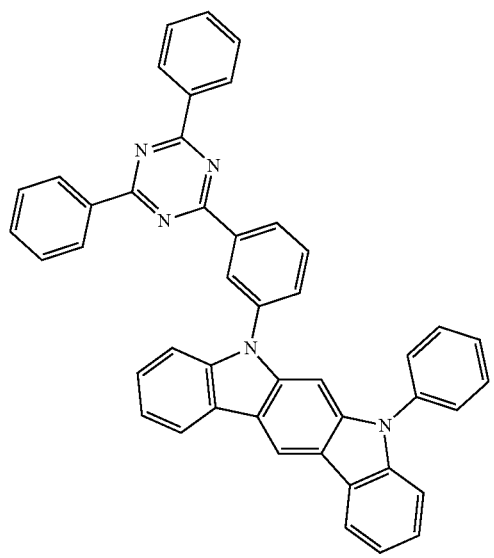
B-124
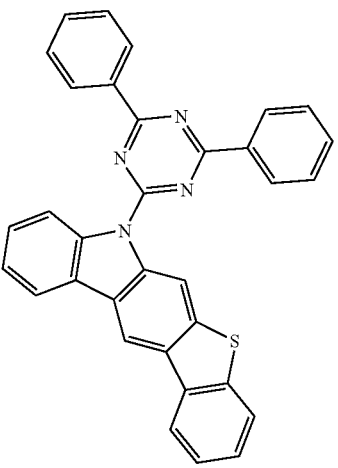
B-122
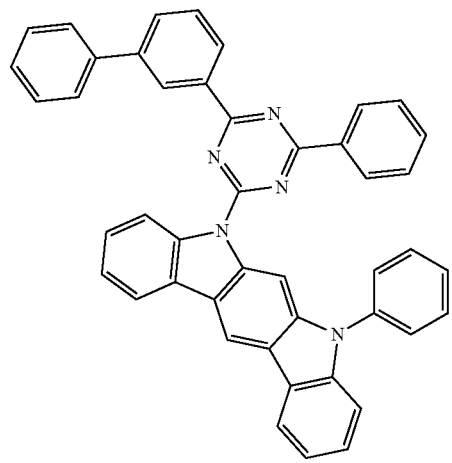
B-125
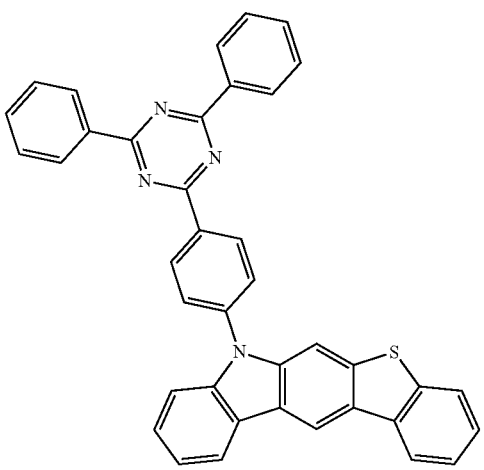
B-123
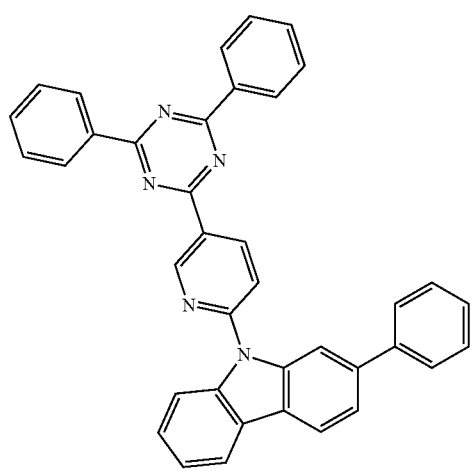
B-126
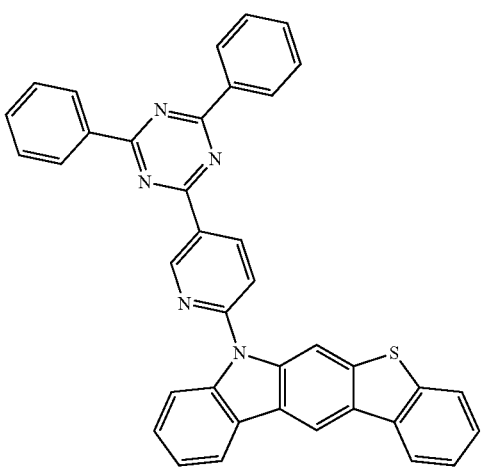

B-127
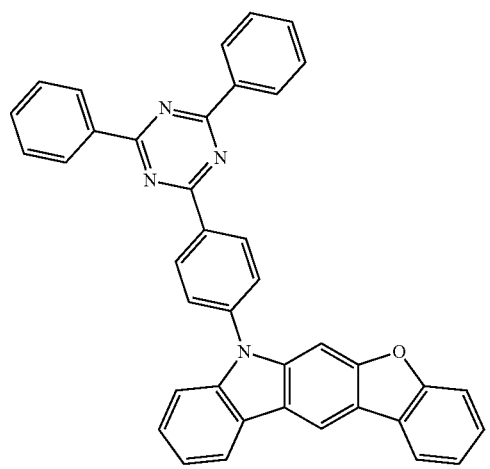
B-128
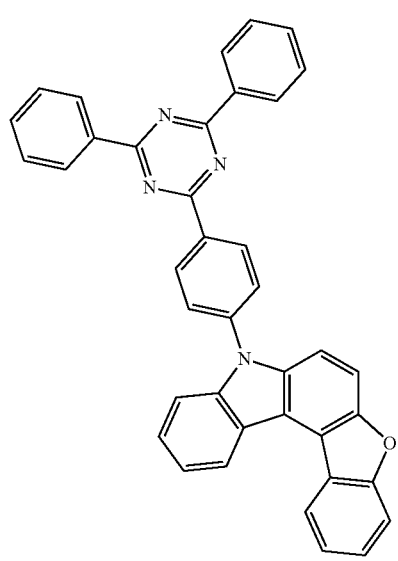
B-129
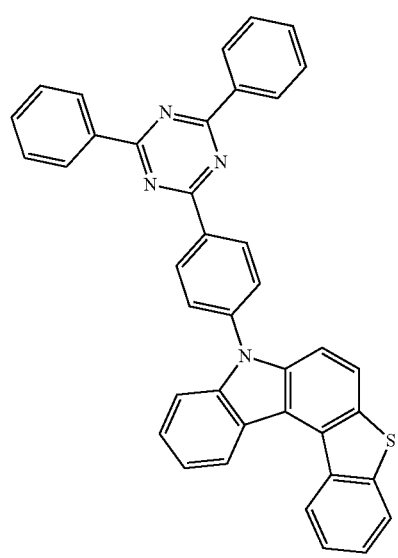
B-130
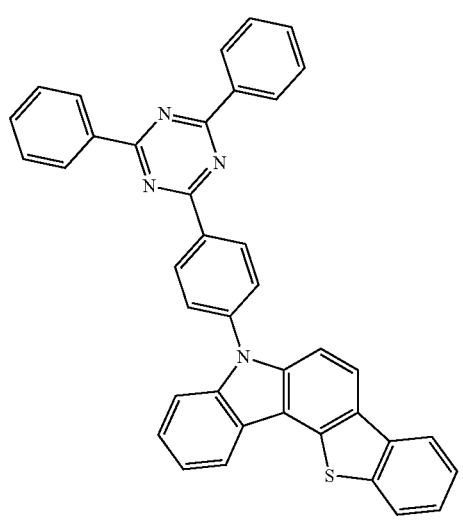
B-131
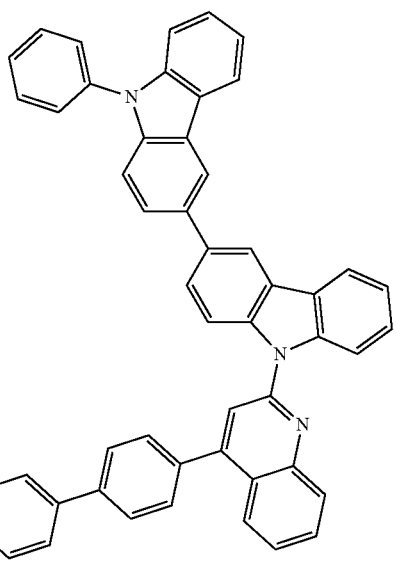
B-132
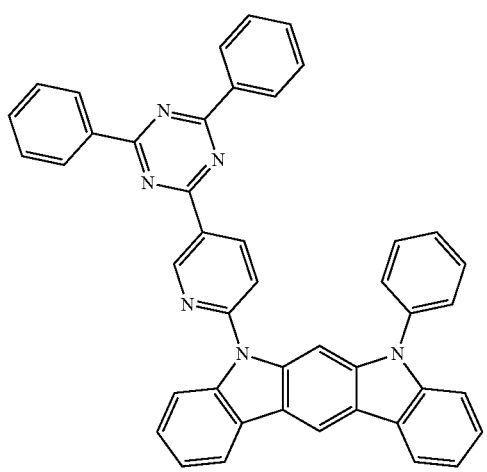

-continued
B-133
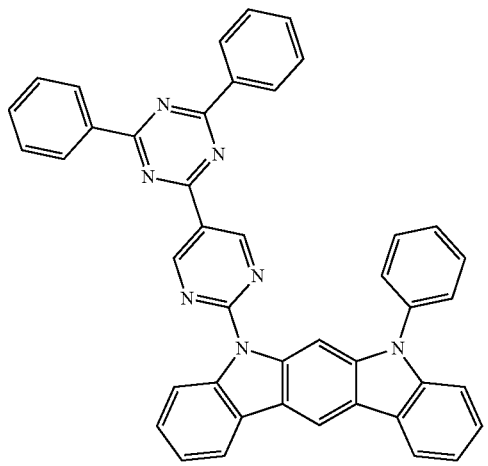
B-134
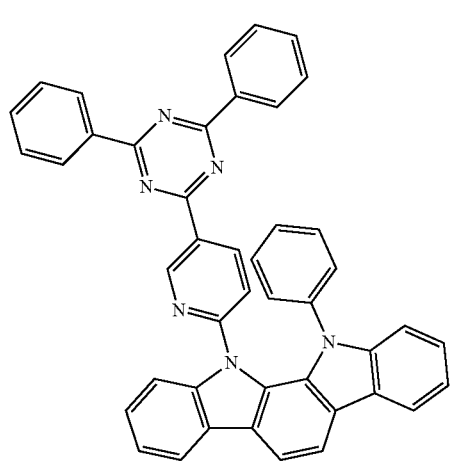
B-135
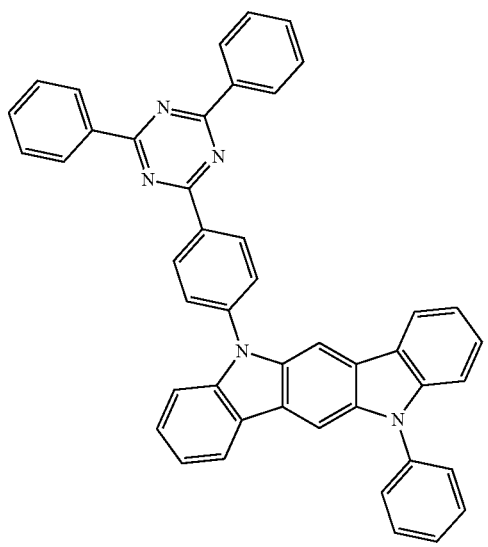
-continued
B-136
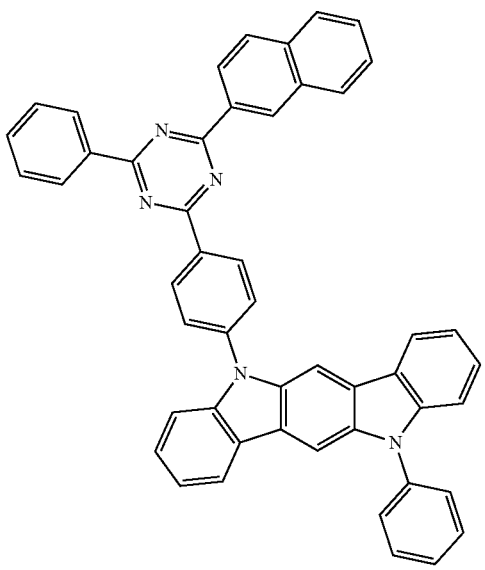
B-137
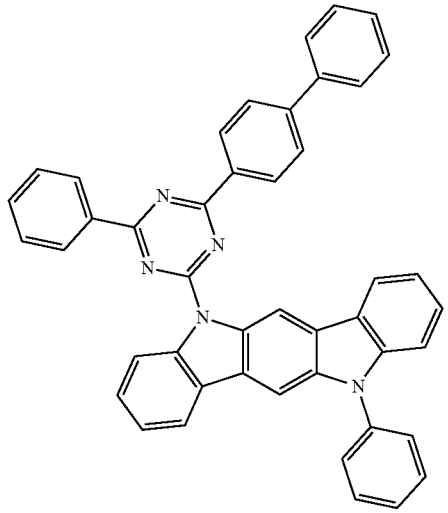
B-138
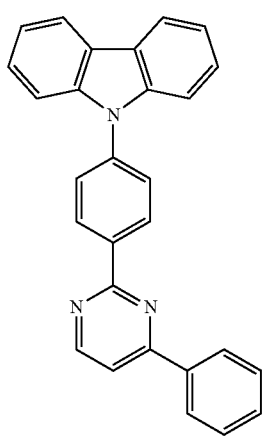

B-139
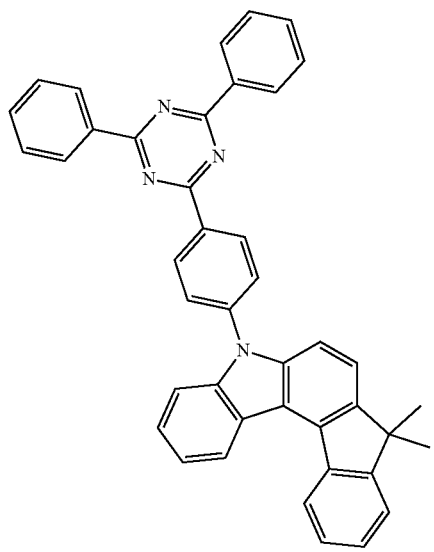
B-140
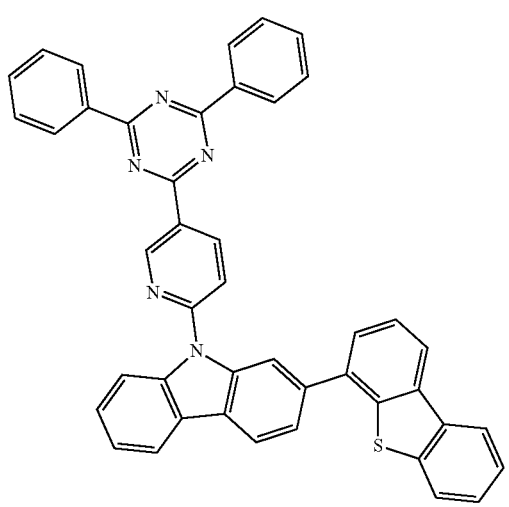
B-141
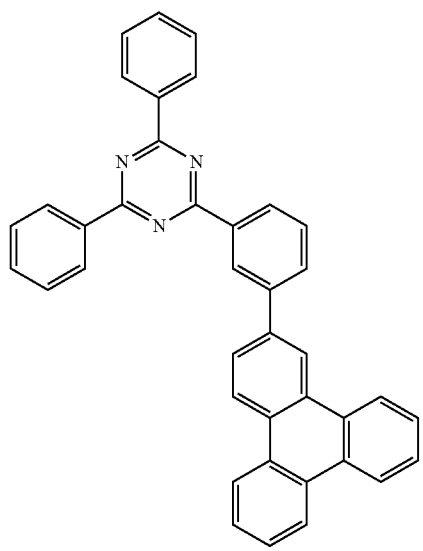
B-142
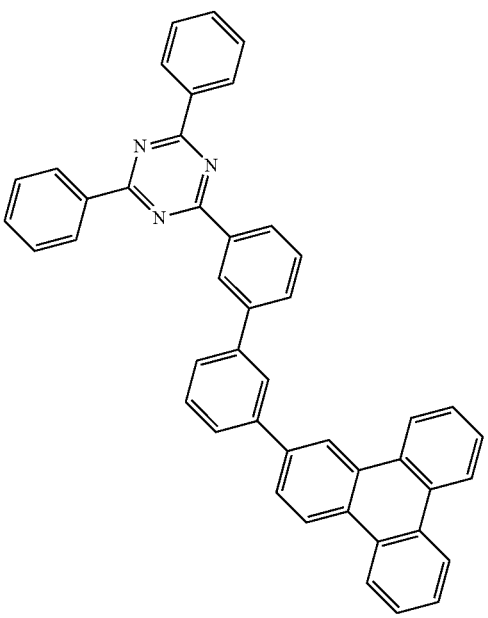
B-143
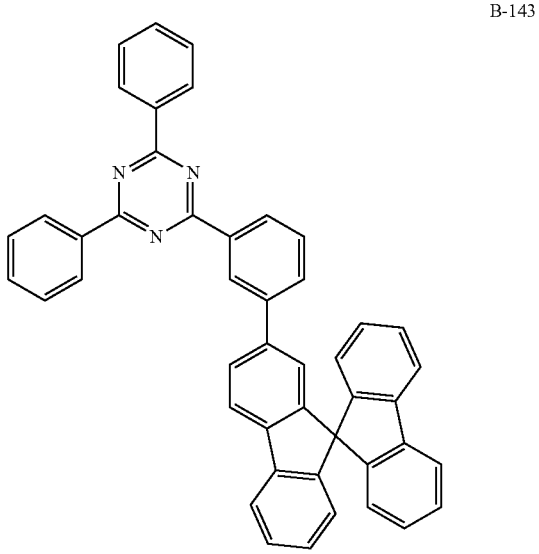

-continued
B-144
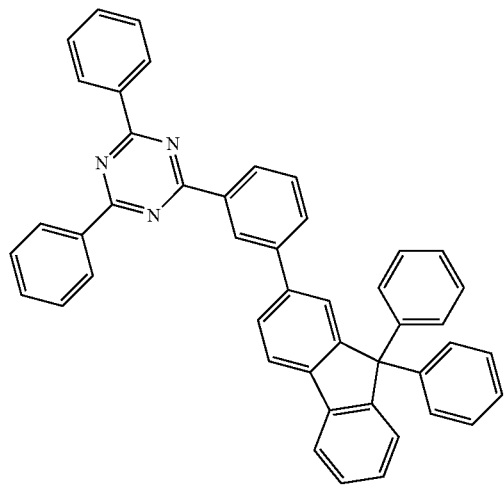
B-145
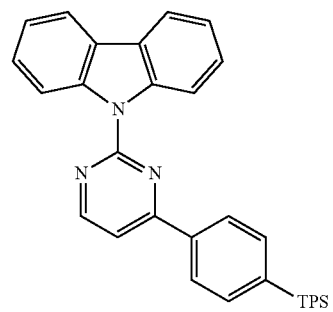
B-146
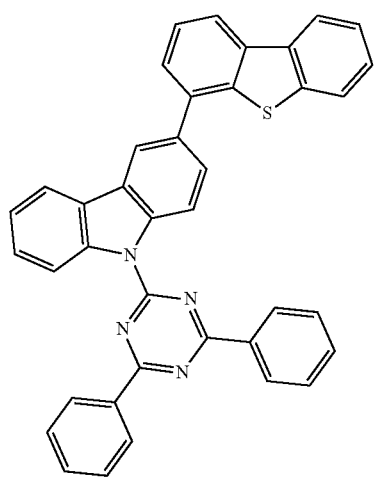
-continued
B-147
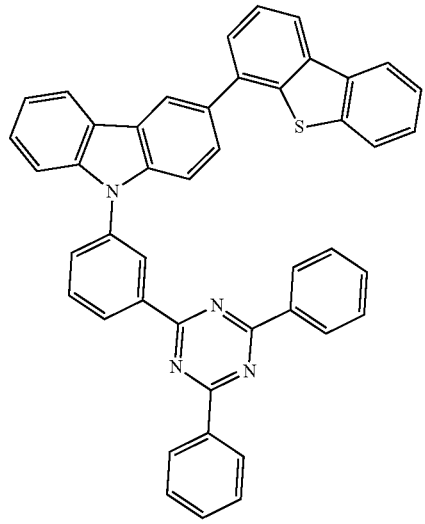
B-148
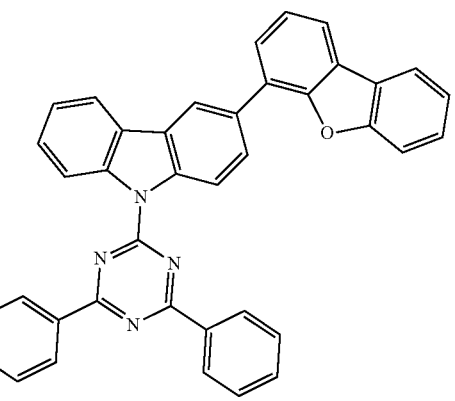
B-149
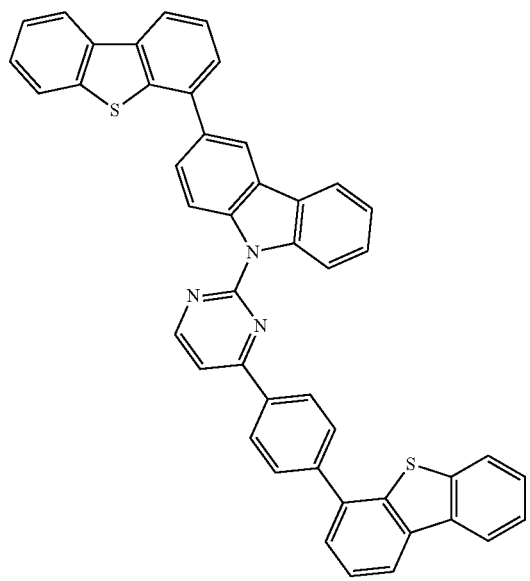

B-150
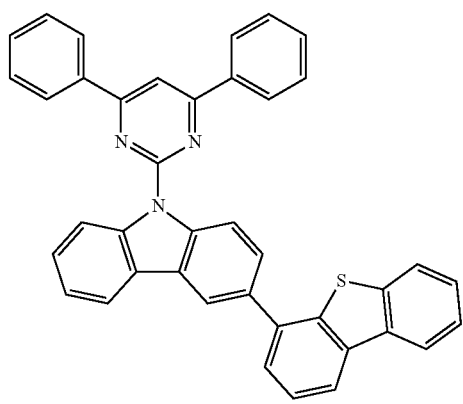
B-151
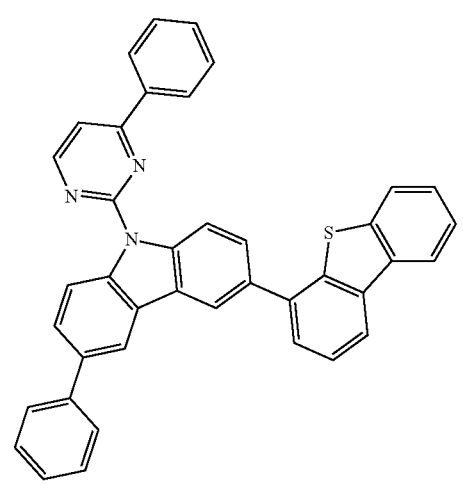
B-152
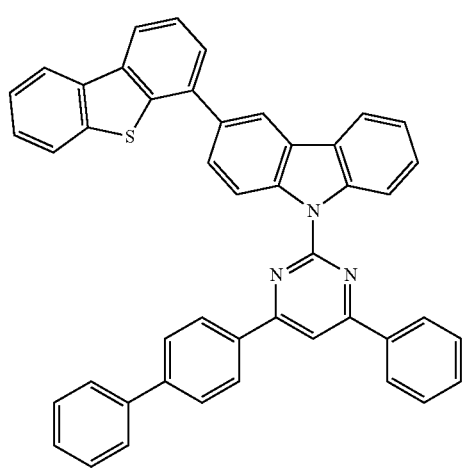
B-153
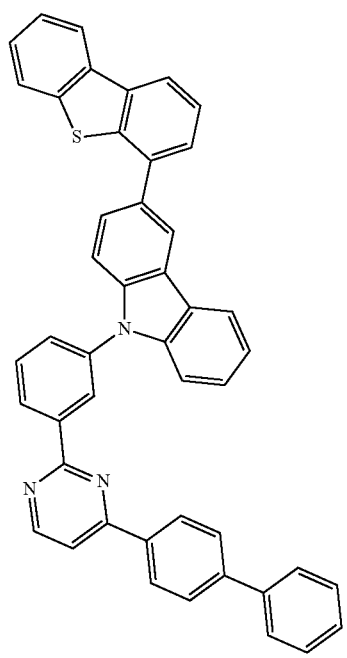
B-154
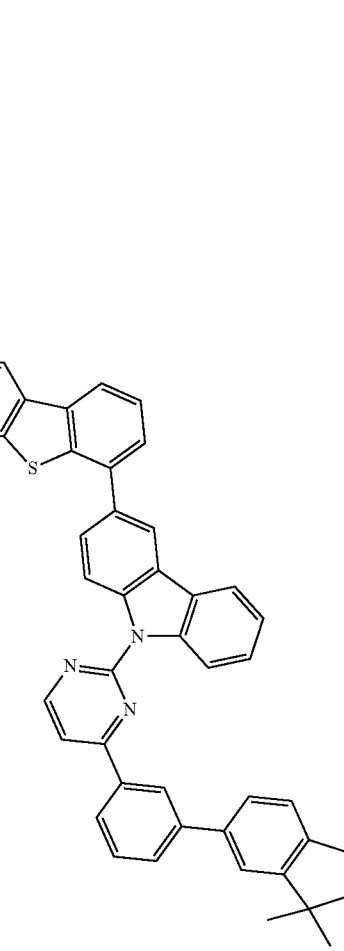

B-155
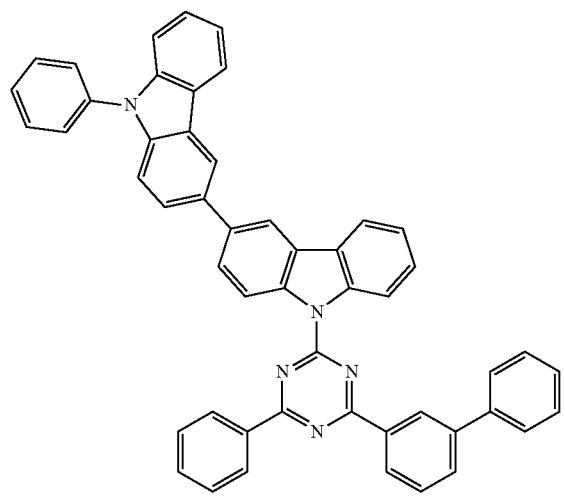
B-156
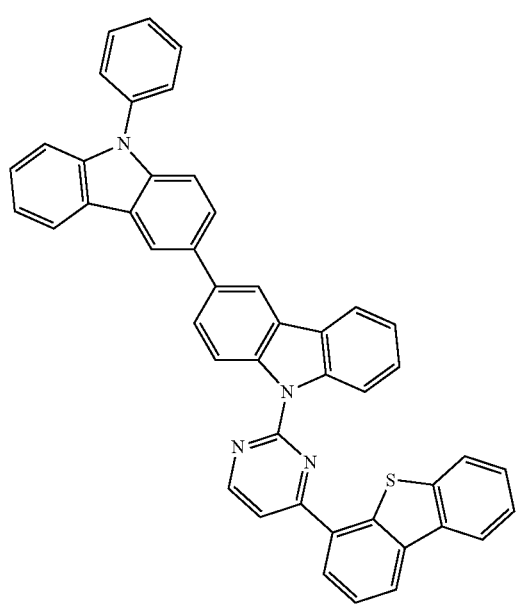
B-157
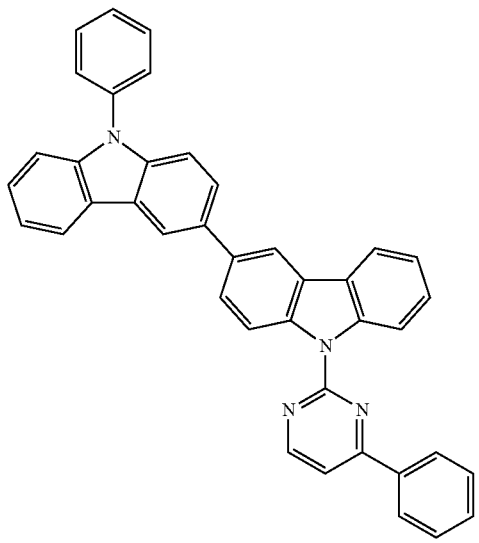
B-158
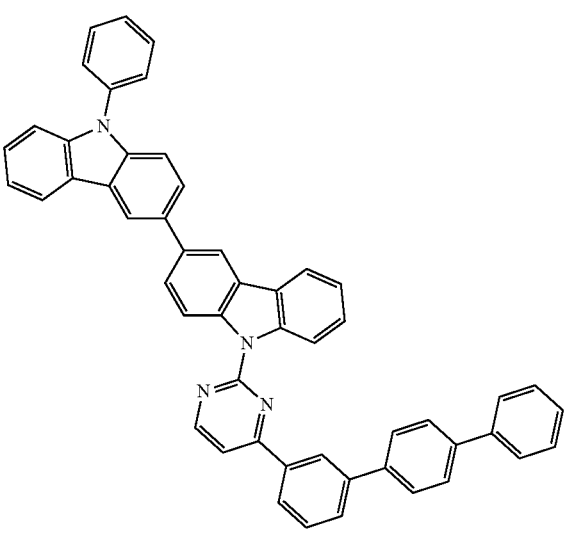

B-159
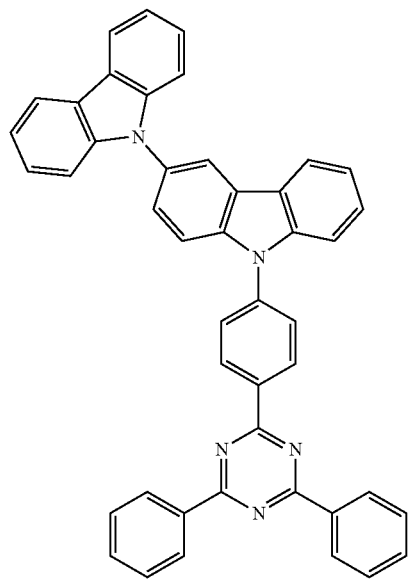
B-160
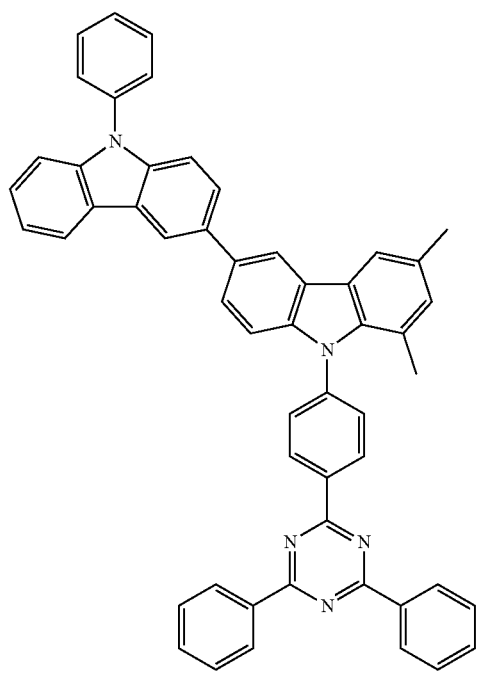
B-161
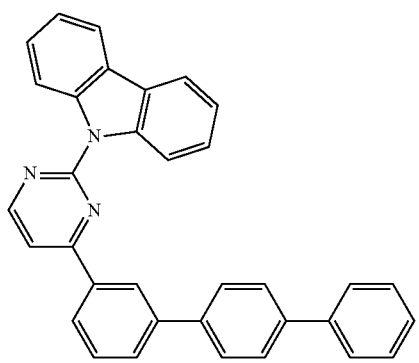
B-162
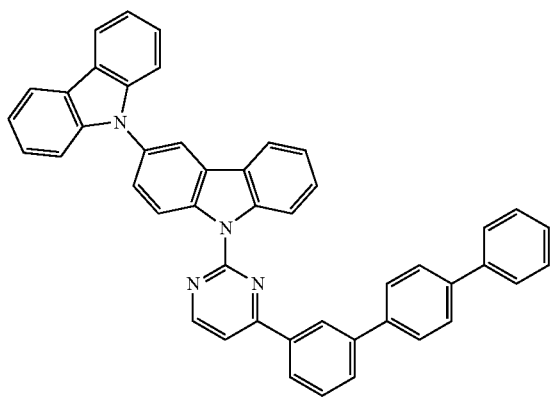
B-163
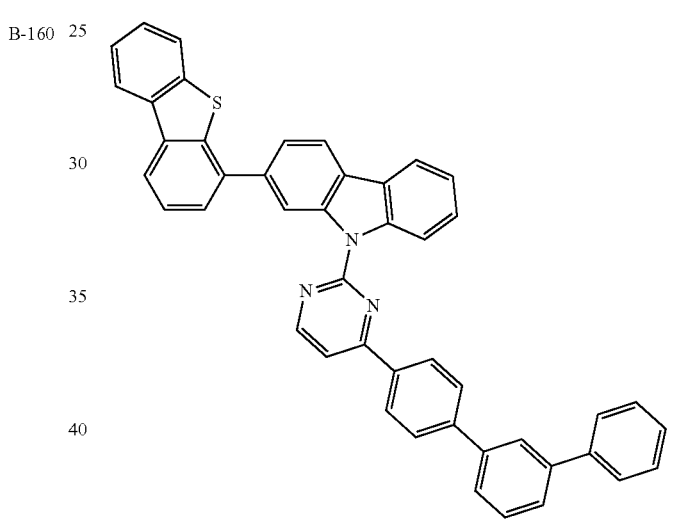
B-164
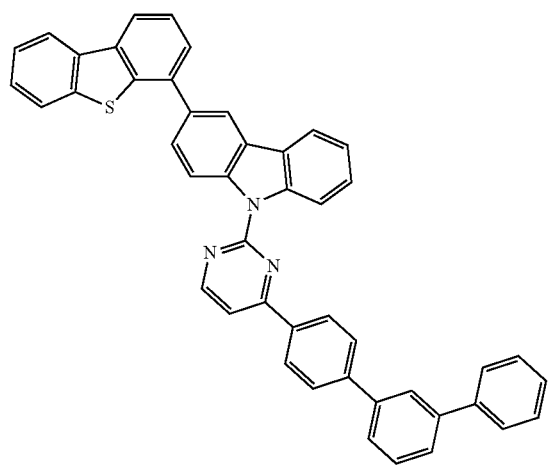

B-165
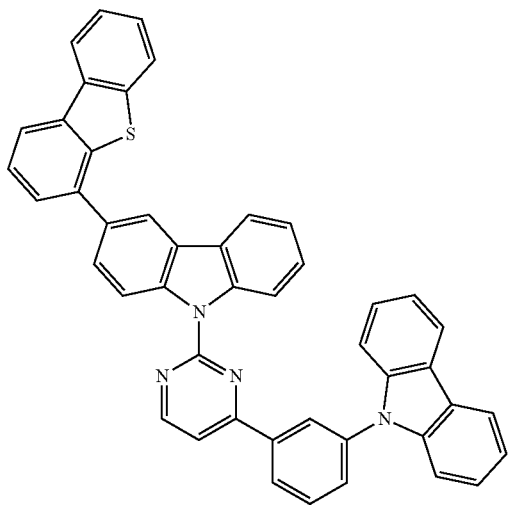
B-166
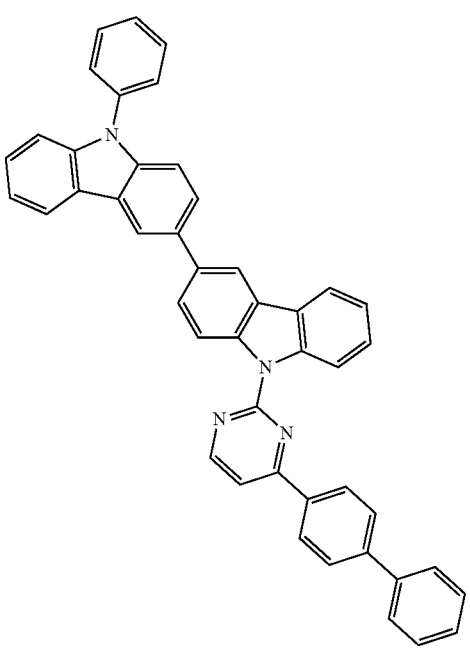
B-167
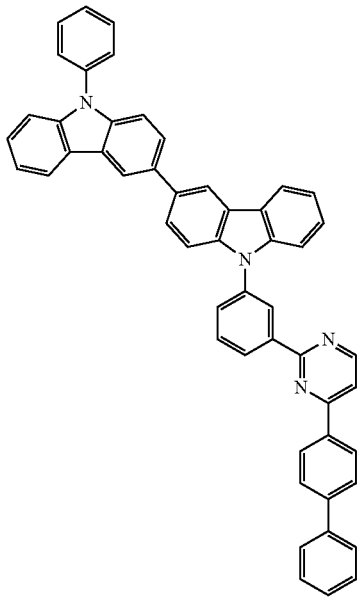
B-168
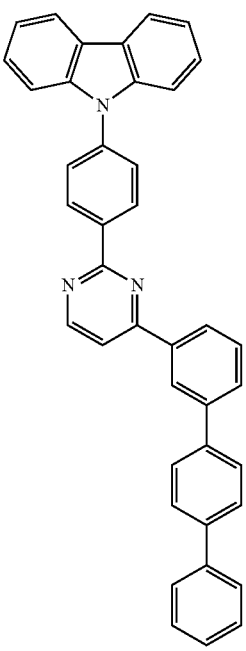

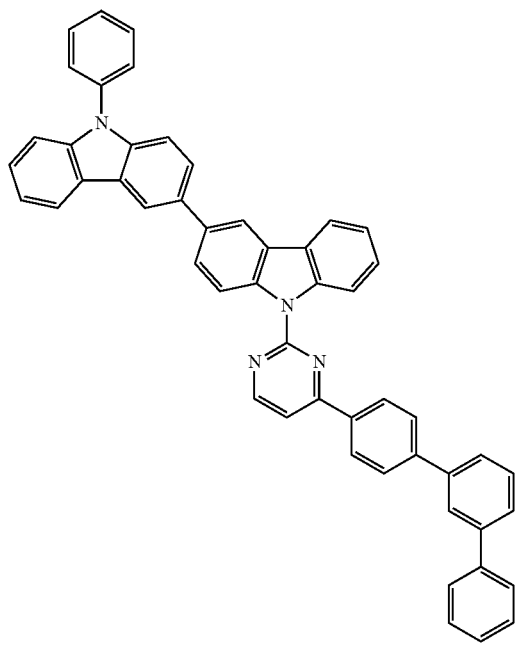
B-169
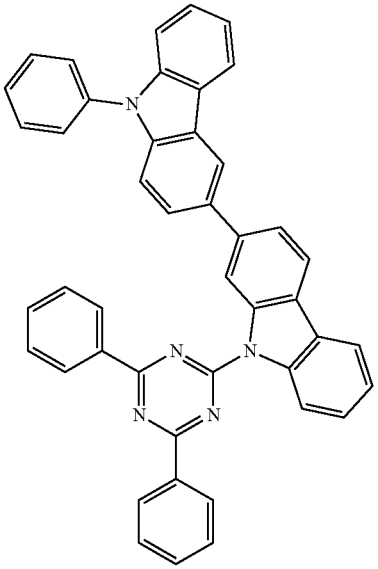
B-171
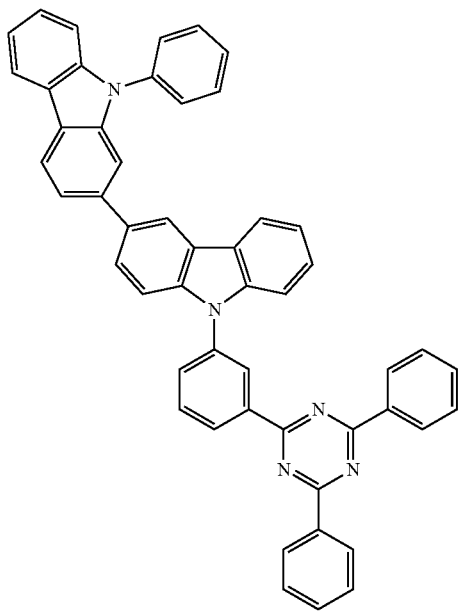
B-172
B-170

B-173
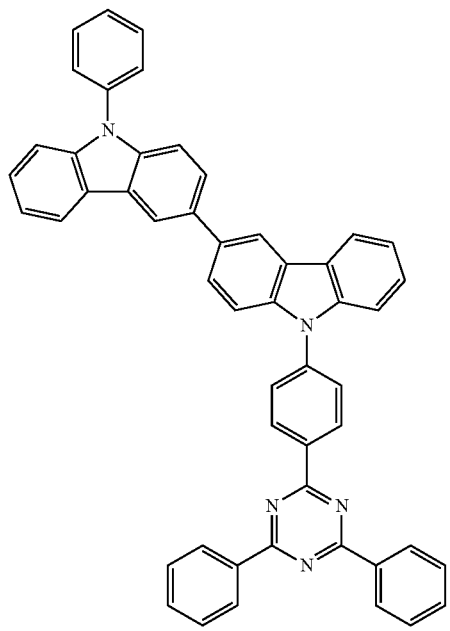
B-174
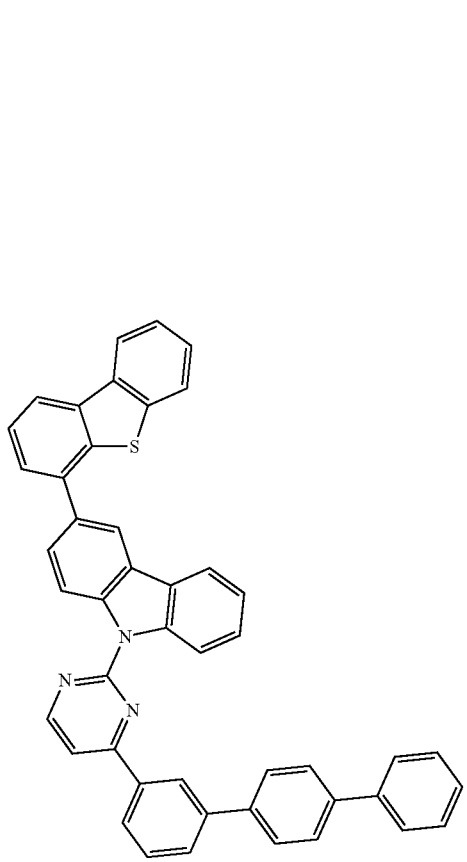
B-175
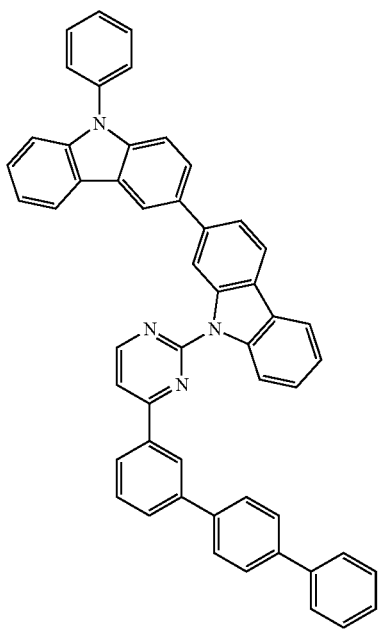
B-176
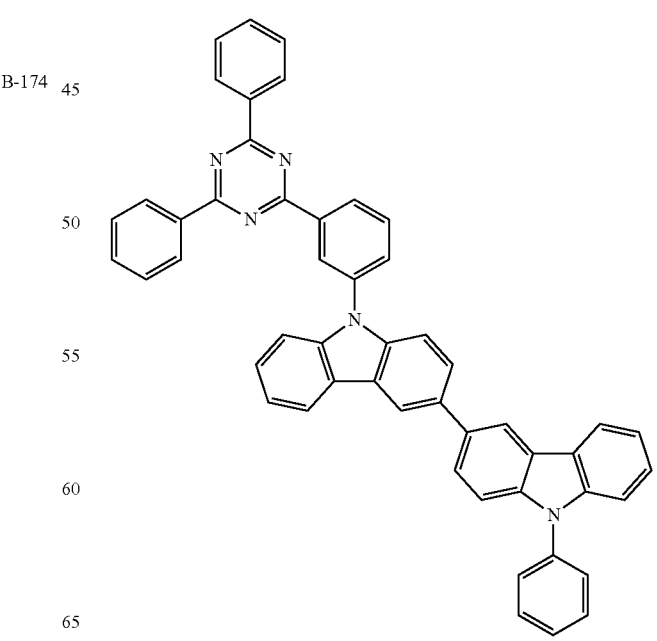

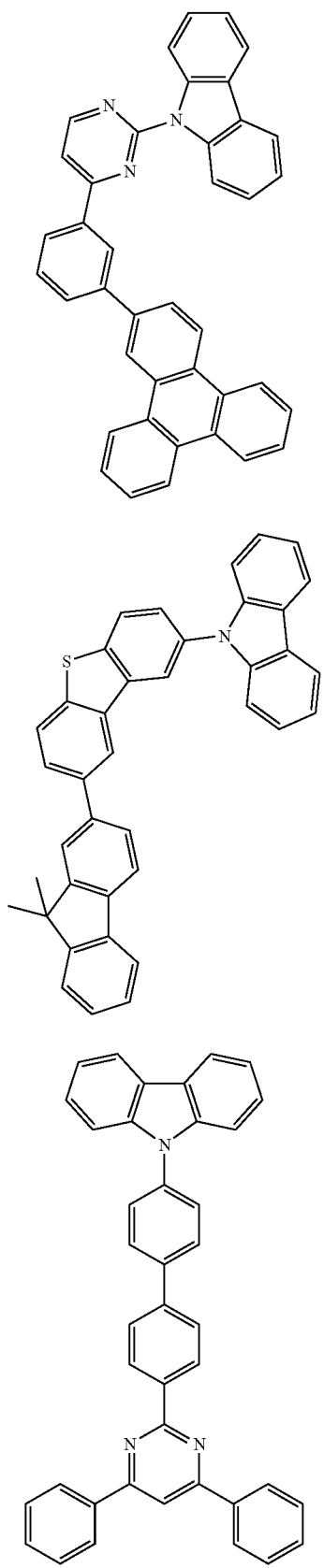
B-177
B-178
B-179
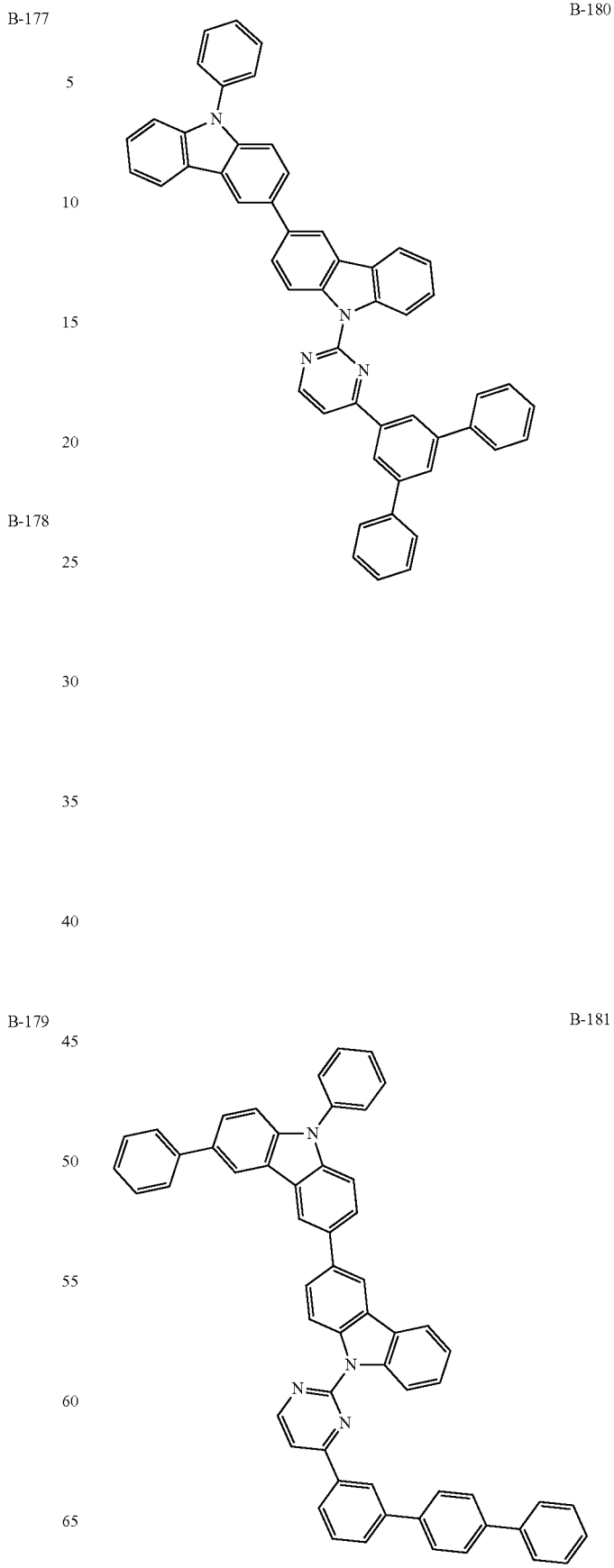
B-180
B-181

B-182
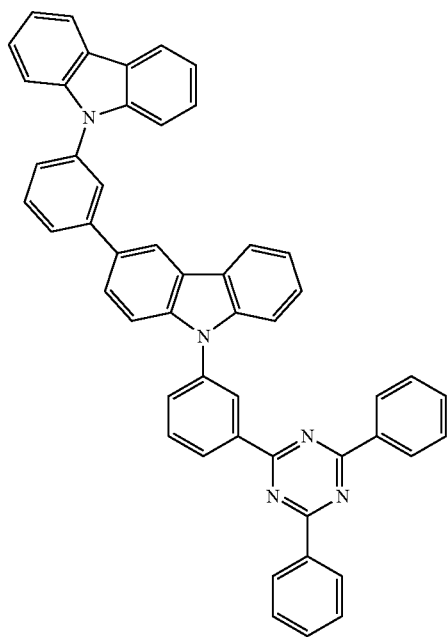
B-184
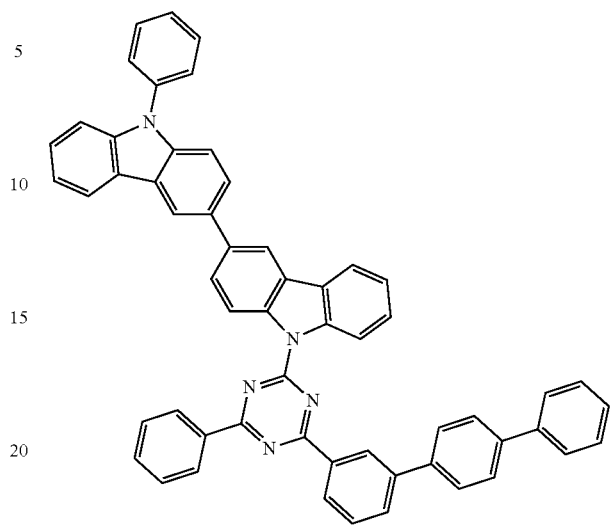
B-185
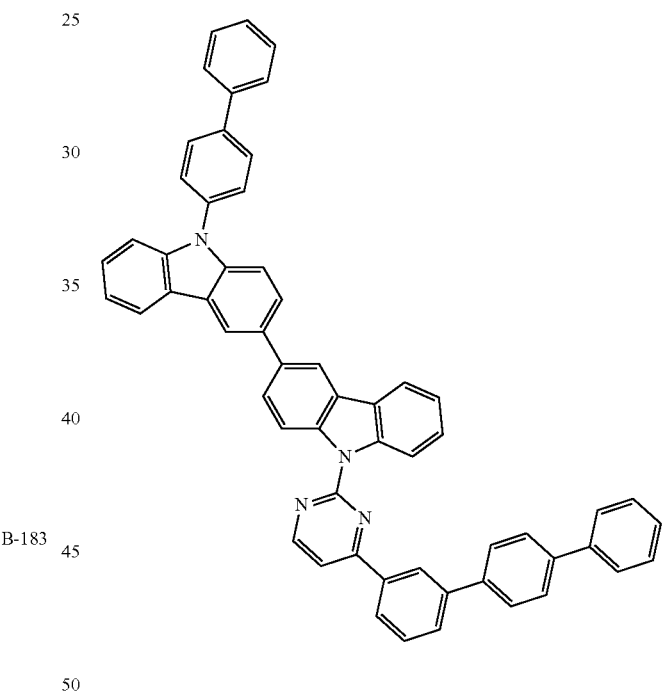
B-183
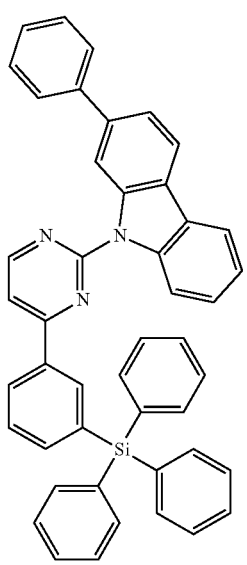
B-186

B-187
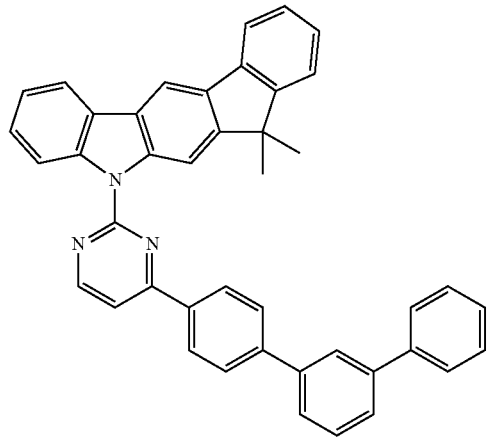
B-188
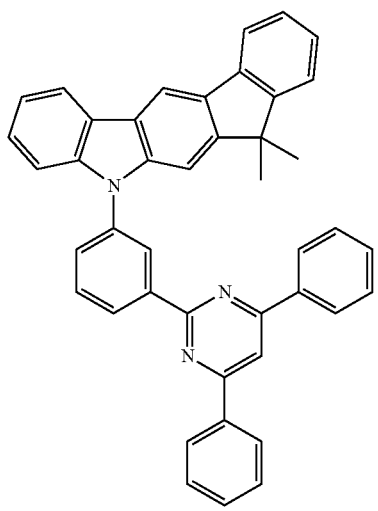
B-189
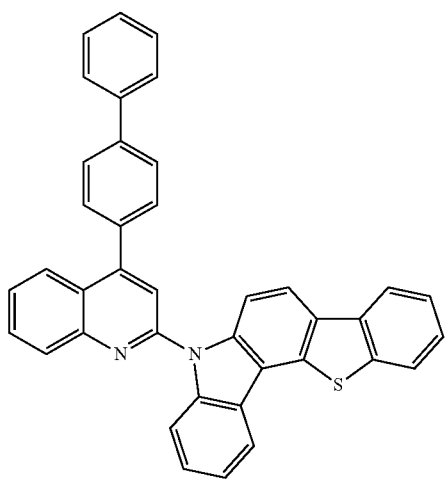
B-190
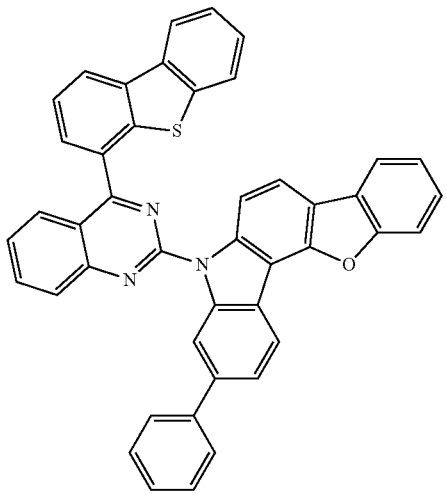
B-191
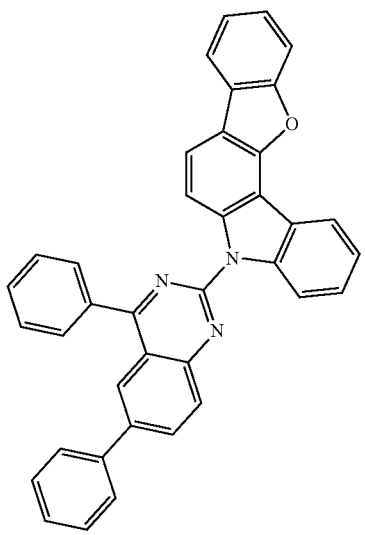
B-192
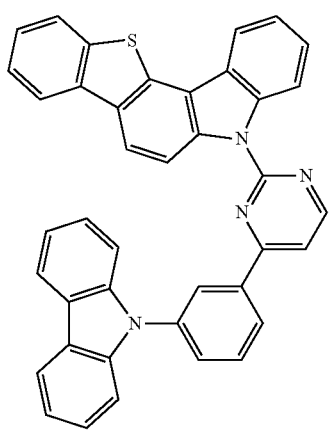

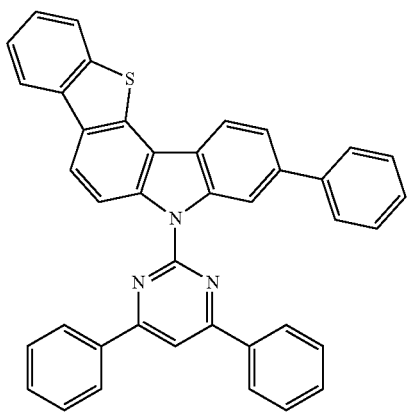
B-193

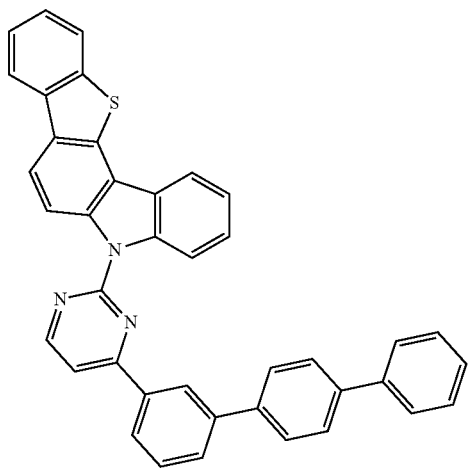
B-196

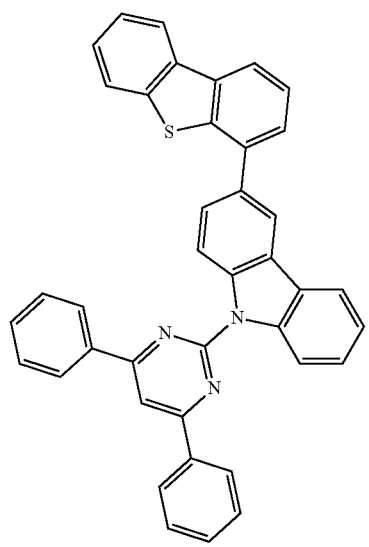
B-194

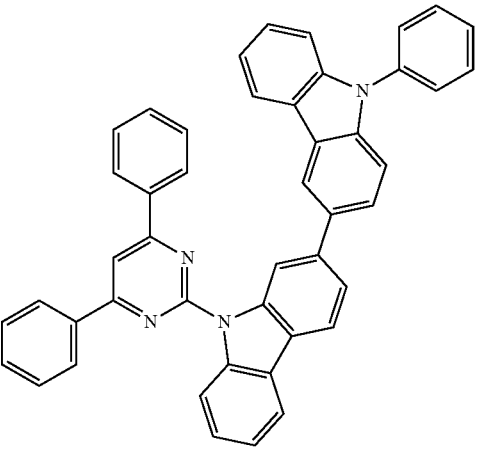
B-197

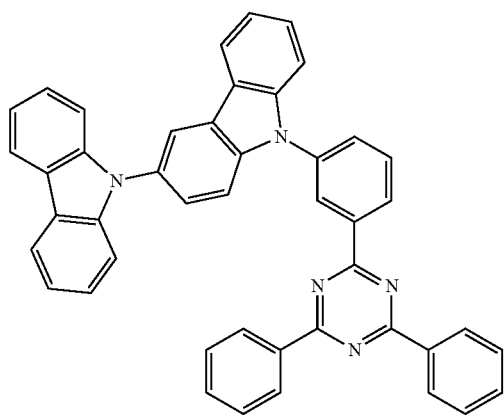
B-195

[Wherein, TPS represents a triphenylsilyl group.]

The dopant comprised in the organic electroluminescent device of the present disclosure is preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise the compound selected from the group consisting of the compounds represented by the following formulas 101 to 103.

wherein, La is selected from the following structures:

(101)

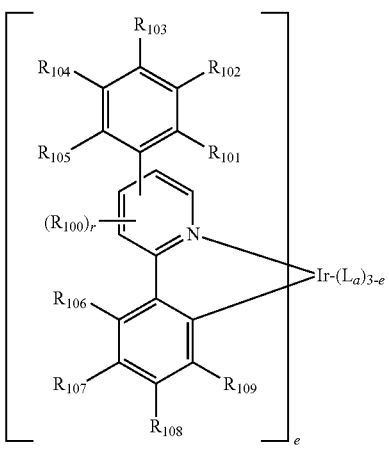

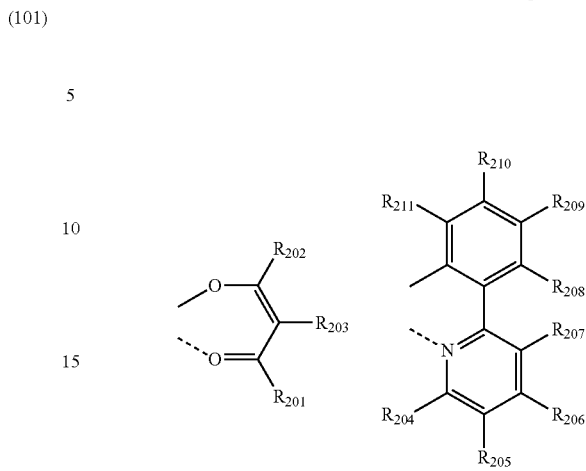

(102)

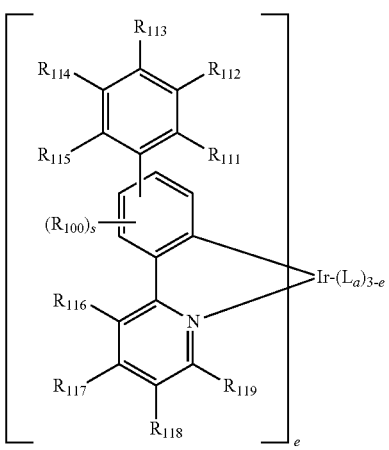

(103)

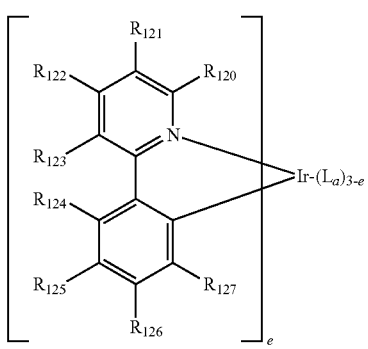

$R_{100}$ represents hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to adjacent $R_{106}$ to $R_{109}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and $R_{120}$ to $R_{123}$ may be linked to adjacent $R_{120}$ to $R_{123}$, respectively, to form a substituted or unsubstituted fused ring, e.g., a quinoline unsubstituted or substituted with an alkyl or an aryl;

$R_{124}$ to $R_{127}$, each independently, represent hydrogen, deuterium, a halogen, a substituted or unsubstituted (C1-C30)alkyl, or a substituted or unsubstituted (C6-C30)aryl; and $R_{124}$ to $R_{127}$ may be linked to adjacent $R_{124}$ to $R_{127}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

$R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; and $R_{208}$ to $R_{211}$ may be linked to adjacent $R_{208}$ to $R_{211}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

r and s, each independently, represent an integer of 1 to 3; where if r or s is an integer of 2 or more, each $R_{100}$ may be the same or different; and e represents an integer of 1 to 3.

The specific examples of the compound used as a dopant are as follows:
D-1
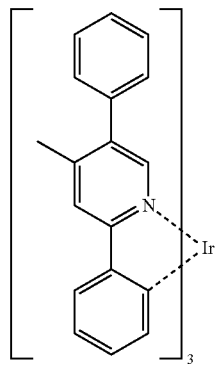
D-2
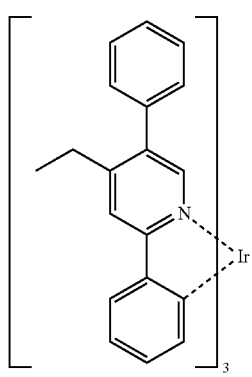
D-3
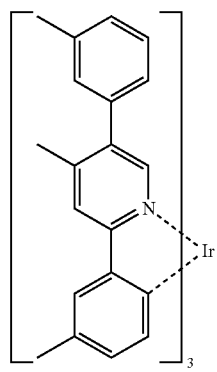
D-4
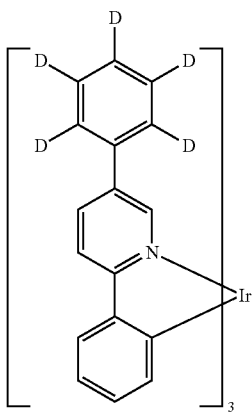
D-5
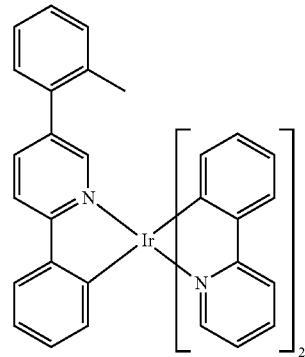
D-6
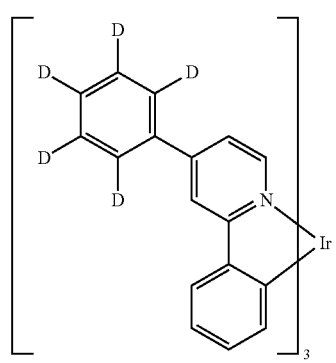
D-7
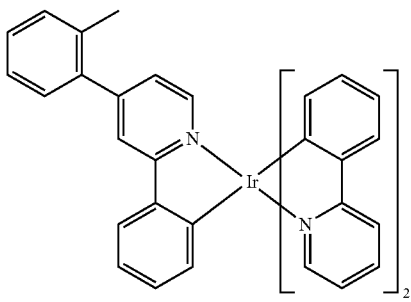
D-8
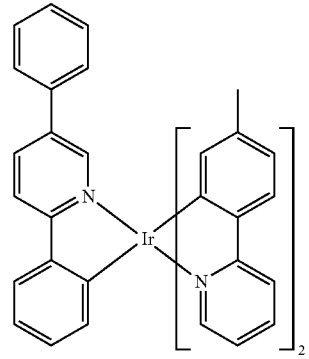

D-9
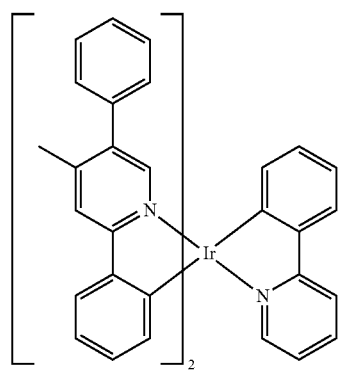
D-10
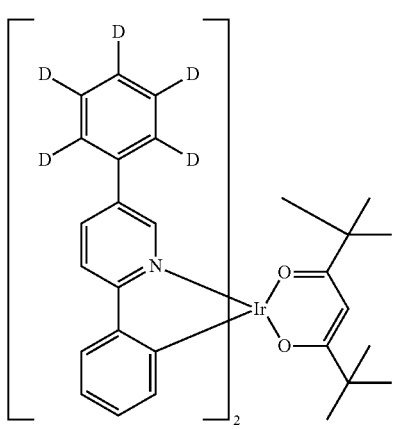
D-11
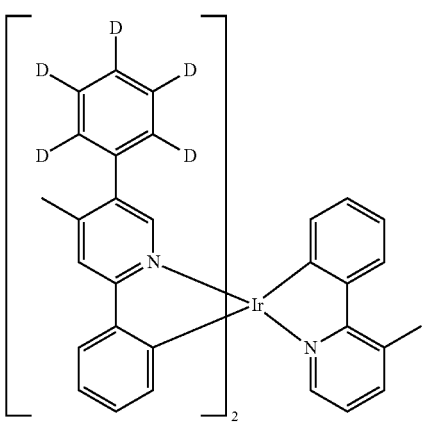
D-12
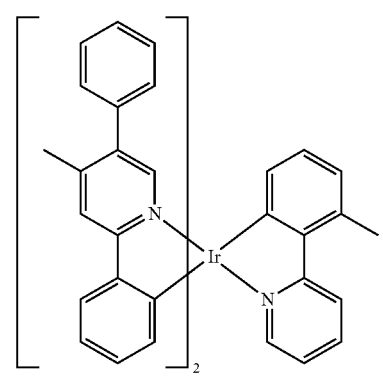
D-13
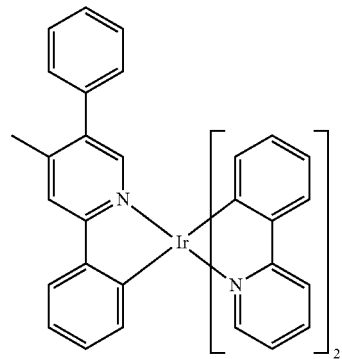
D-14
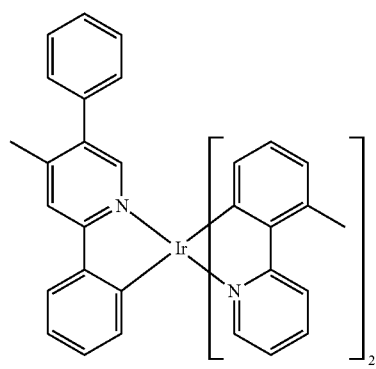
D-15
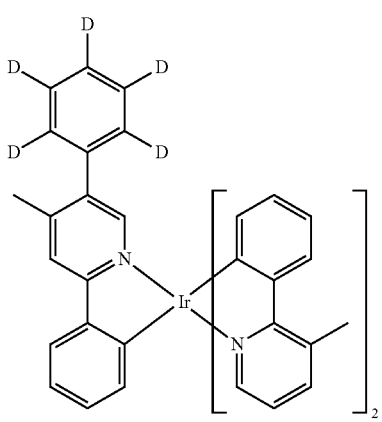
D-16
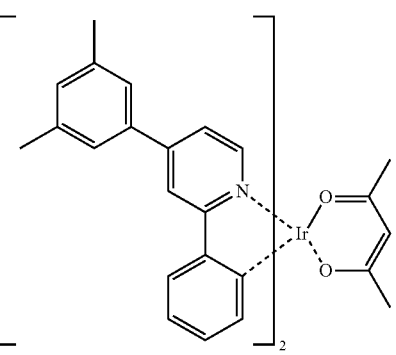

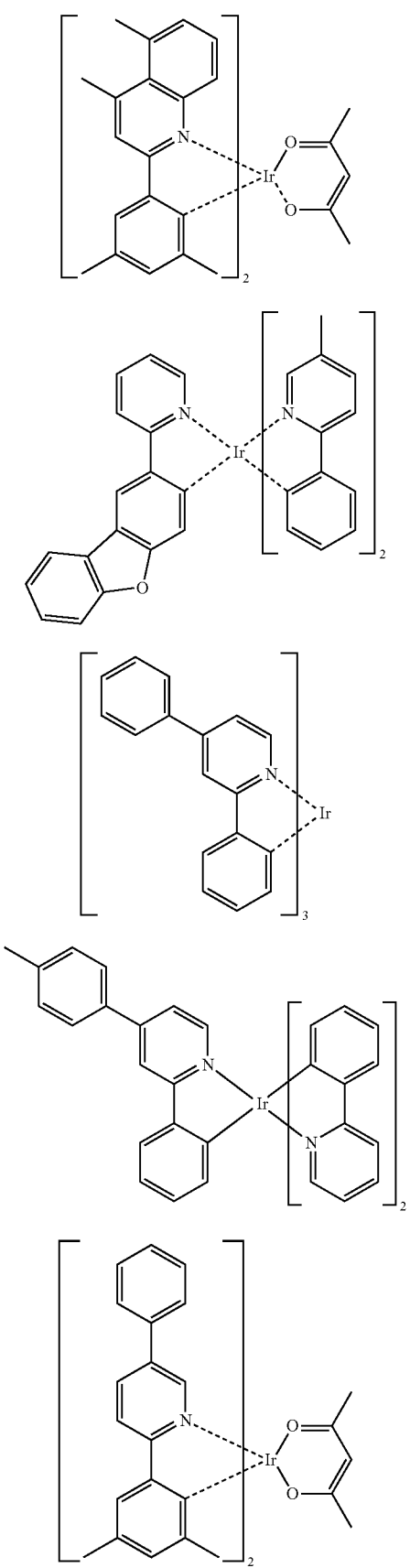

-continued
D-26
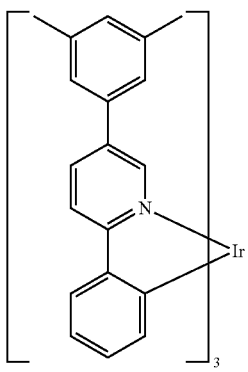
D-27
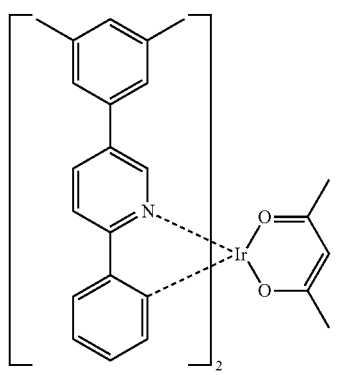
D-28
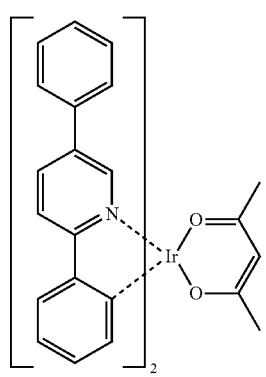
D-29
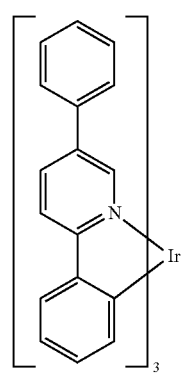
-continued
D-30
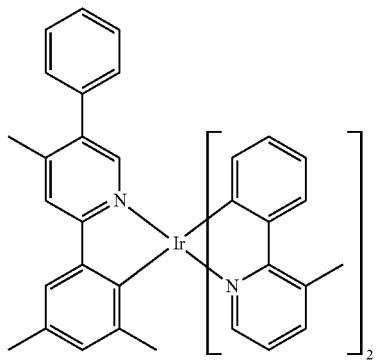
D-31
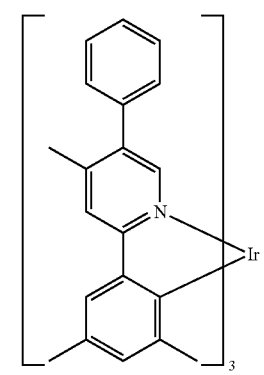
D-32
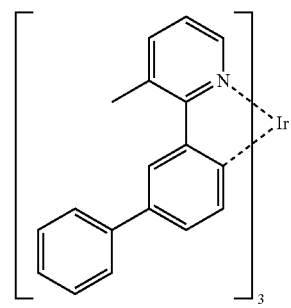
D-33
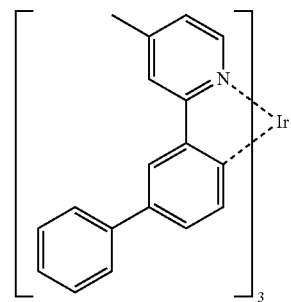

-continued
D-34
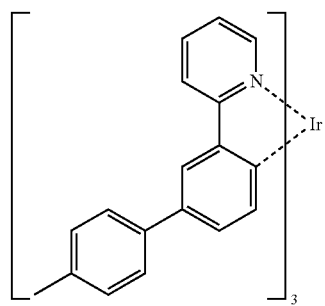
D-35
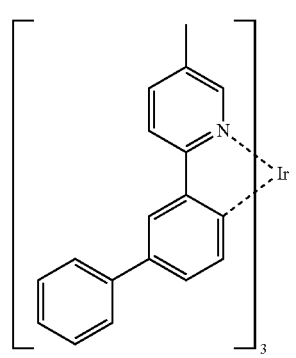
D-36
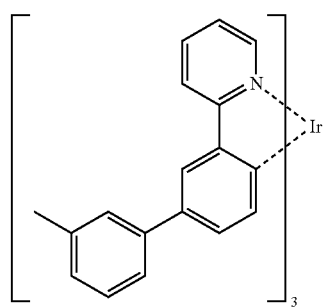
D-37
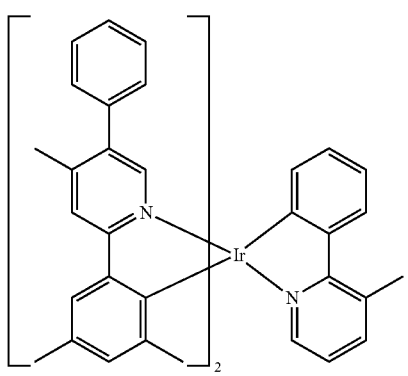
-continued
D-38
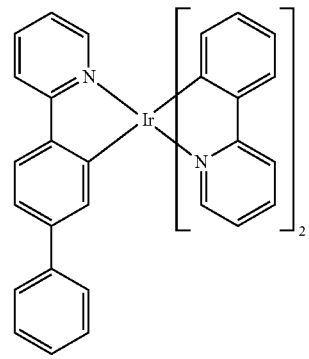
D-39
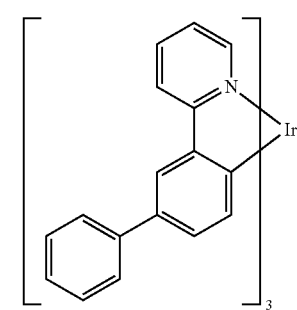
D-40
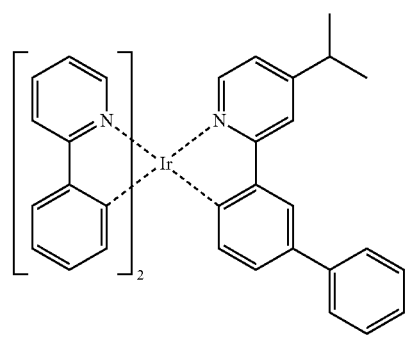
D-41
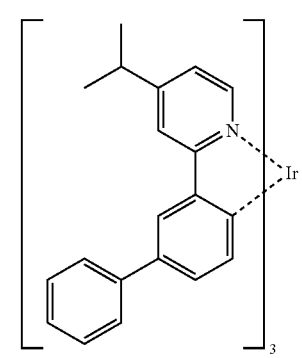
D-42
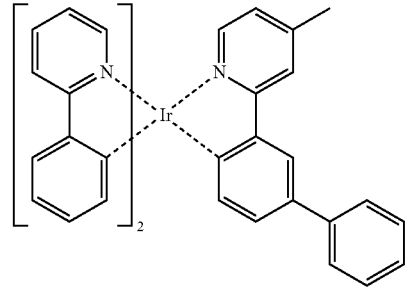

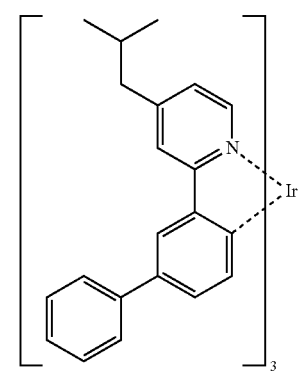
D-43
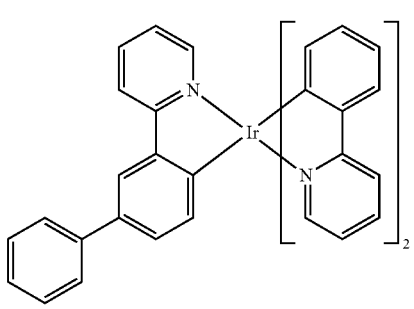
D-47
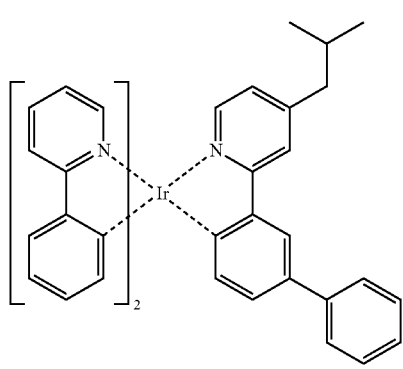
D-44
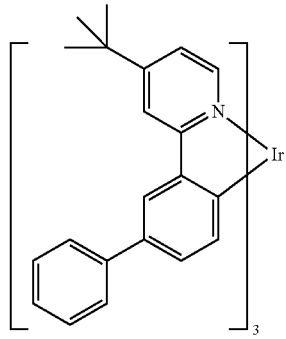
D-48
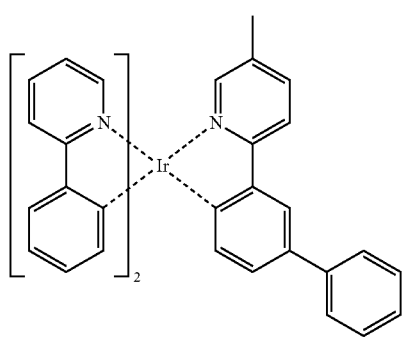
D-45
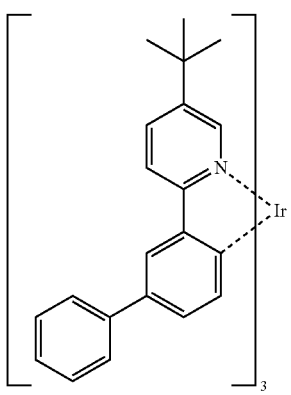
D-49
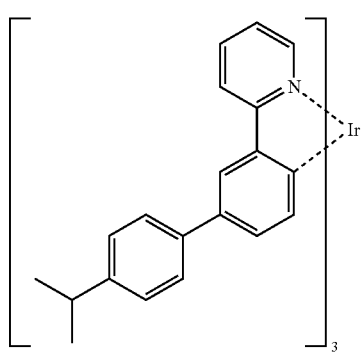
D-46
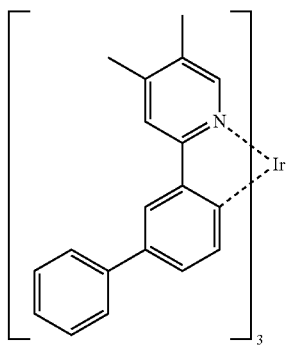
D-50

-continued
D-51
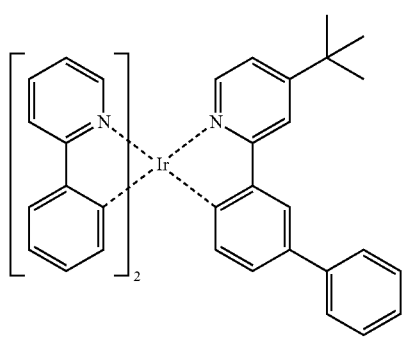
D-52
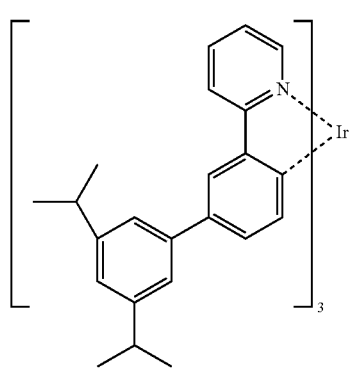
D-53
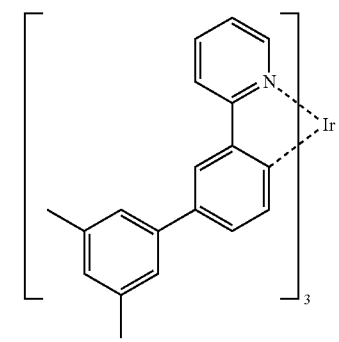
D-54
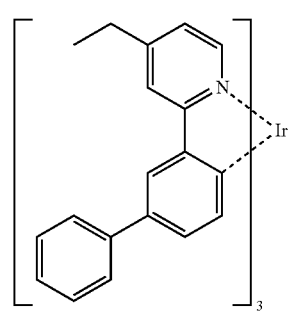
-continued
D-55
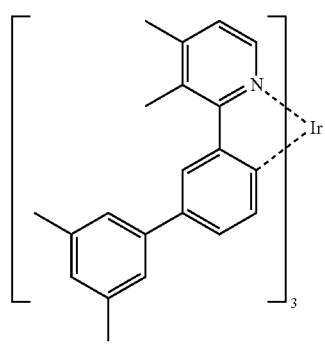
D-56
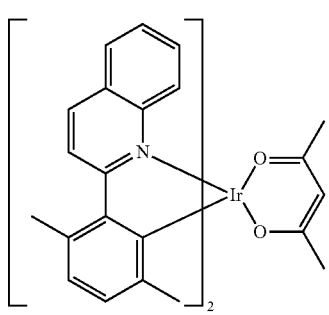
D-57
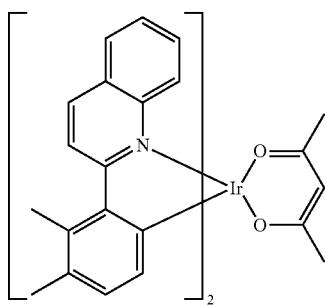
D-58
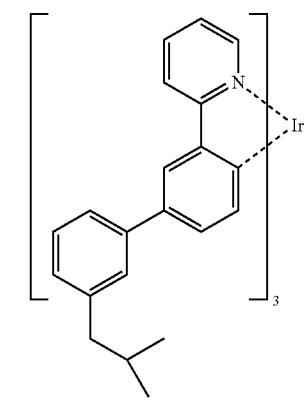

-continued
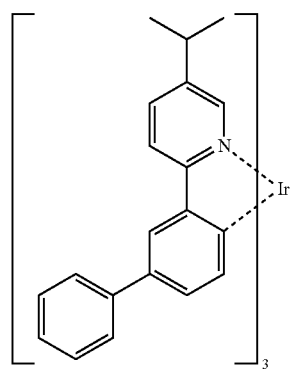
D-59
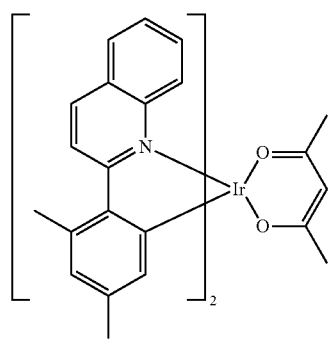
D-60
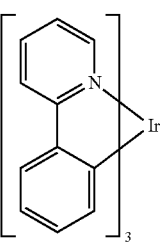
D-61
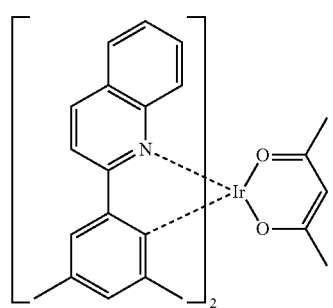
D-62
-continued
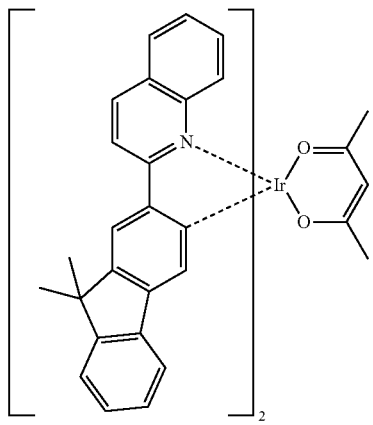
D-63
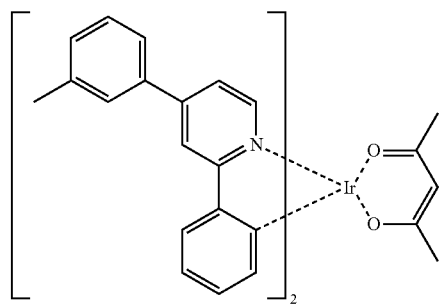
D-64
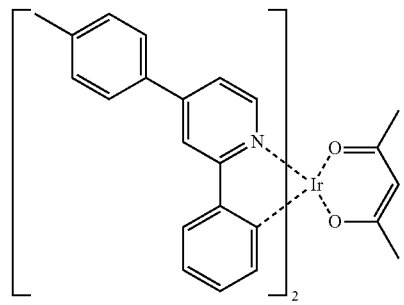
D-65
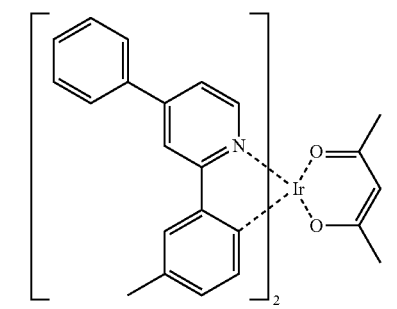
D-66
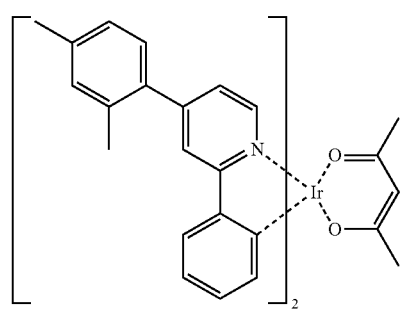
D-67

D-68
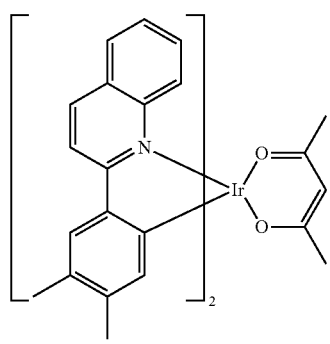
D-69
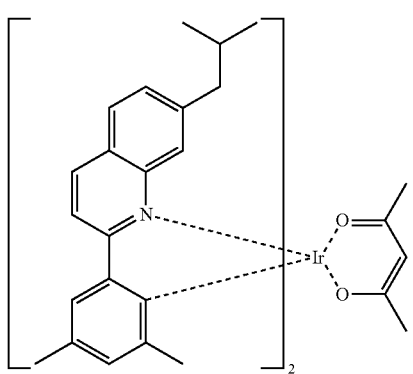
D-70
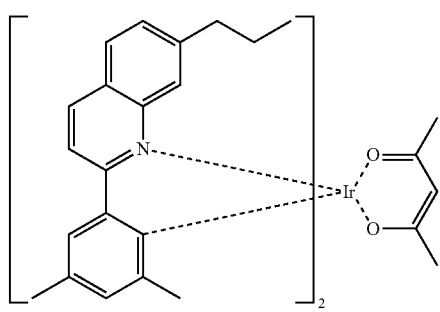
D-71
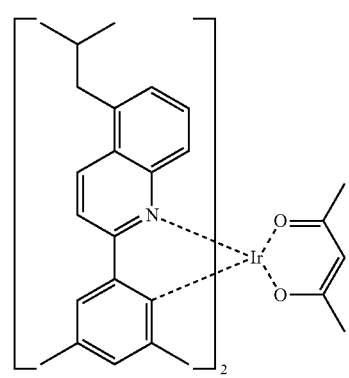
D-72
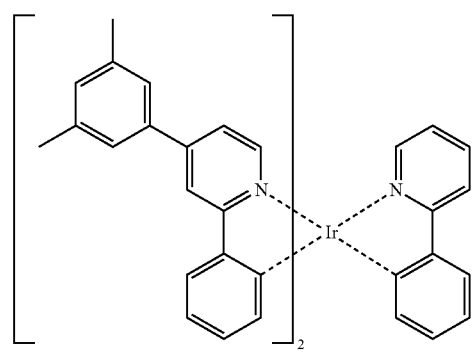
D-73
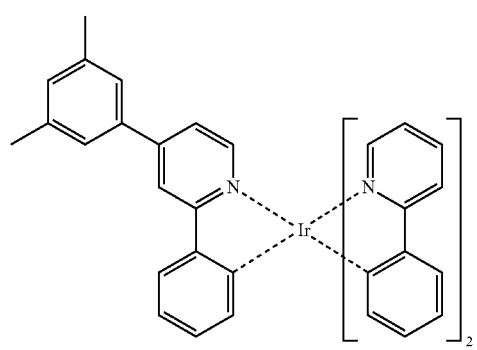
D-74
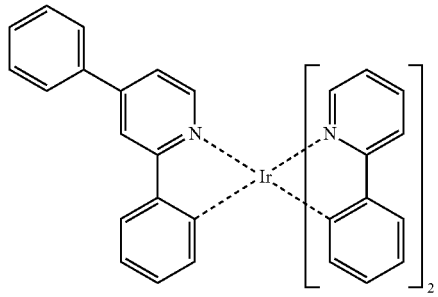
D-75
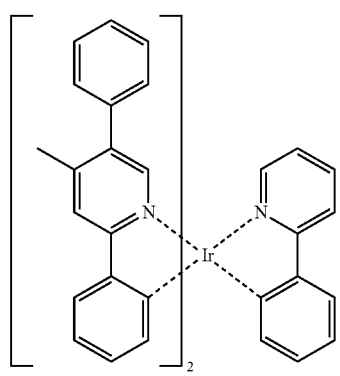

D-76
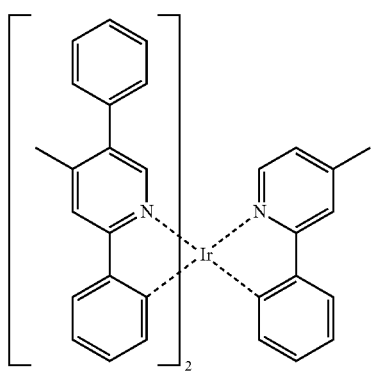
D-77
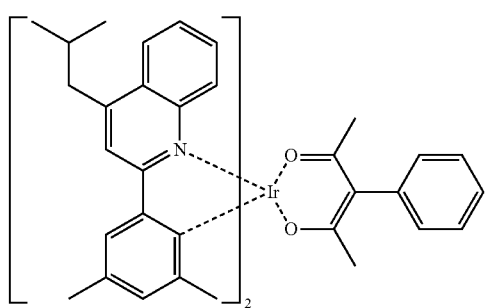
D-78
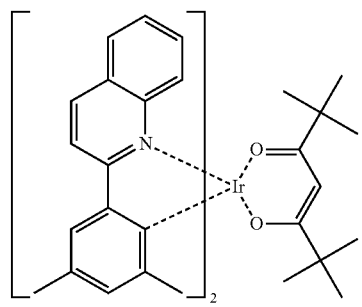
D-79
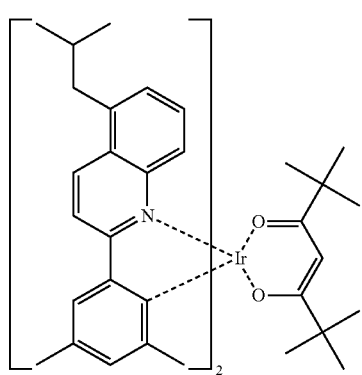
D-80
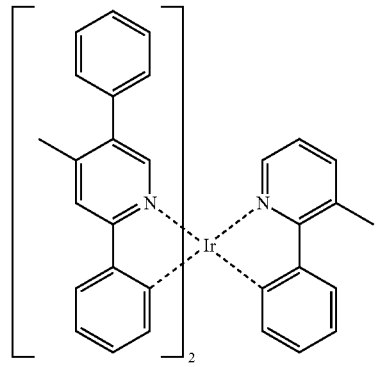
D-81
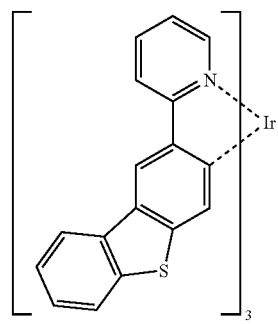
D-82
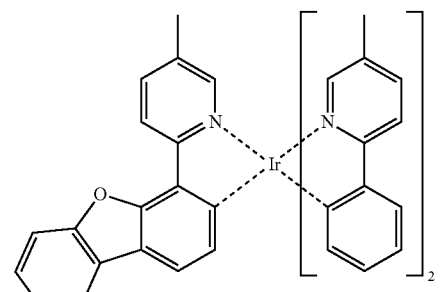
D-83
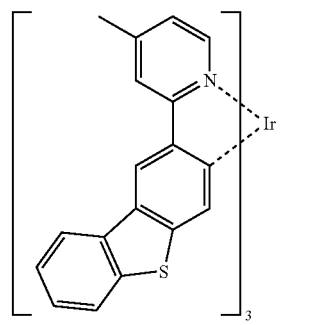
D-84
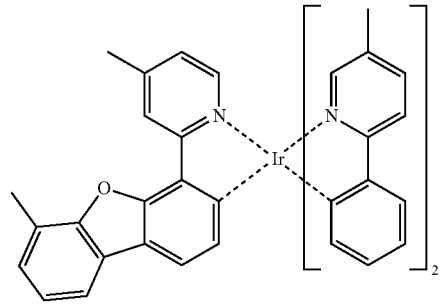

D-85
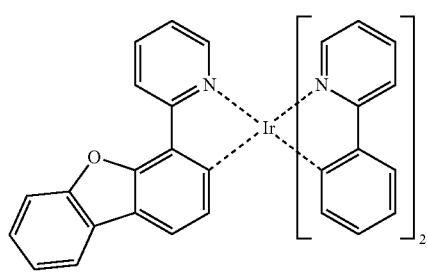
D-86
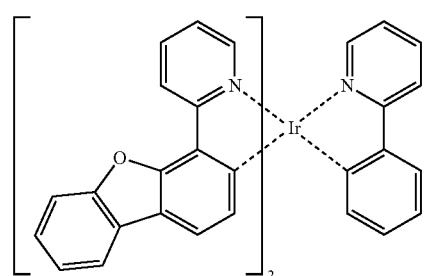
D-87
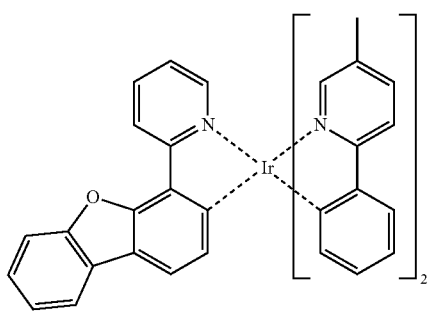
D-88
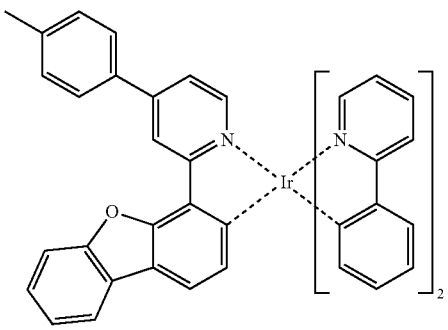
D-89
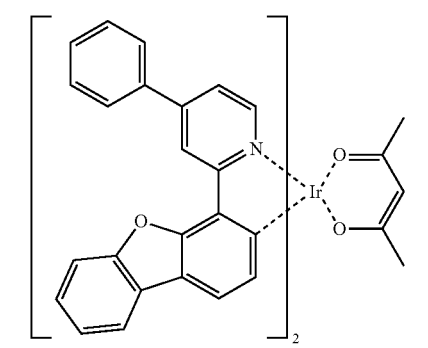
D-90
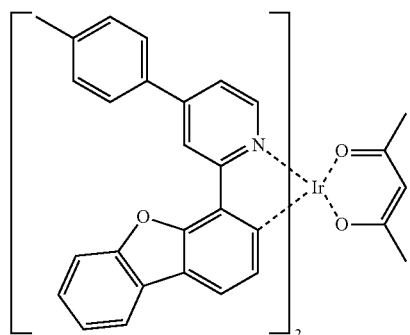
D-91
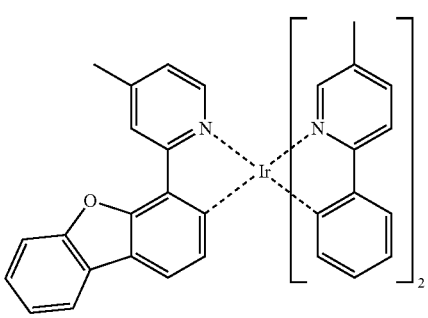
D-92
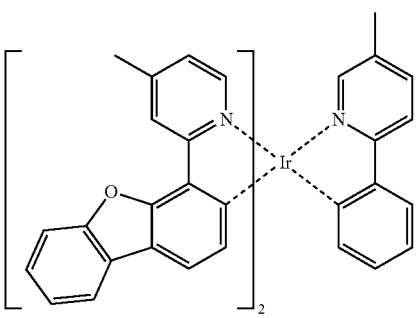
D-93
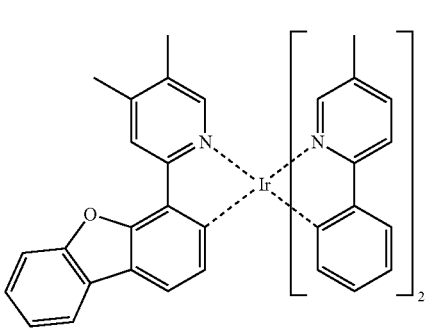
D-94
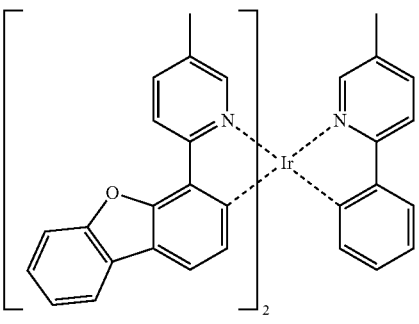

D-95
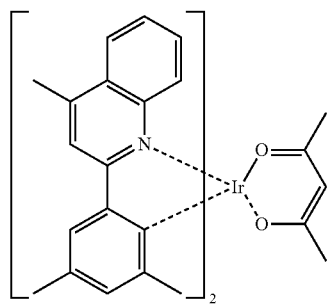
D-96
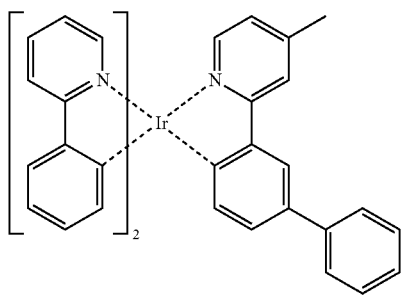
D-97
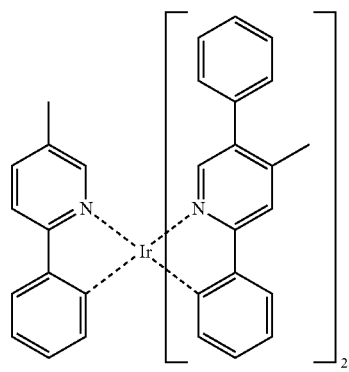
D-98
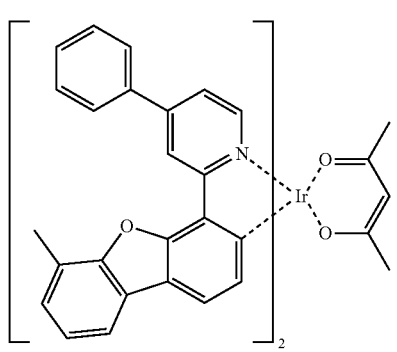
D-99
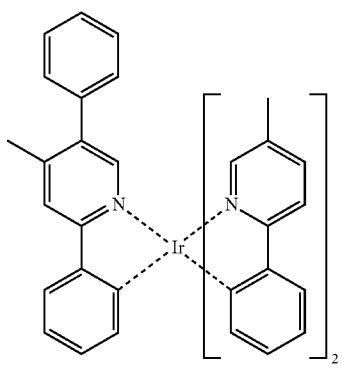
D-100
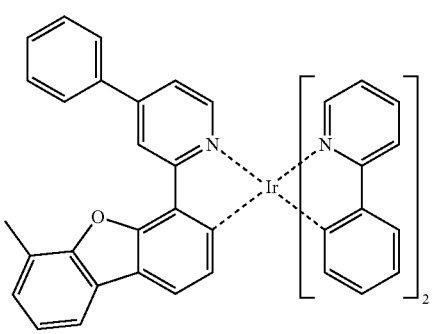
D-101
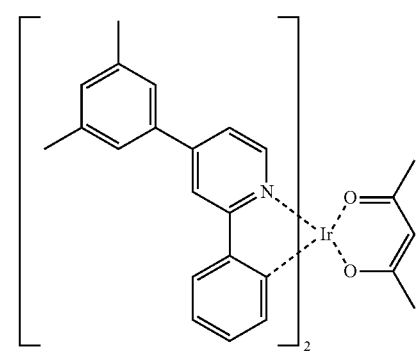
D-102
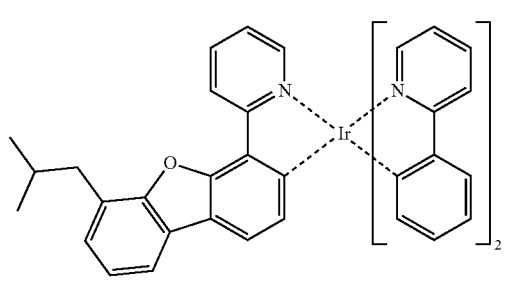

D-103
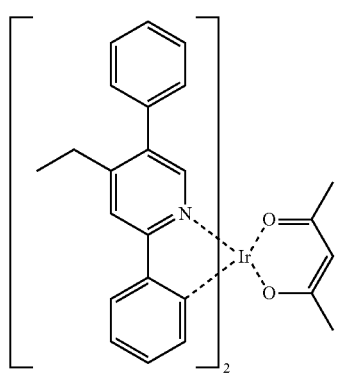
D-104
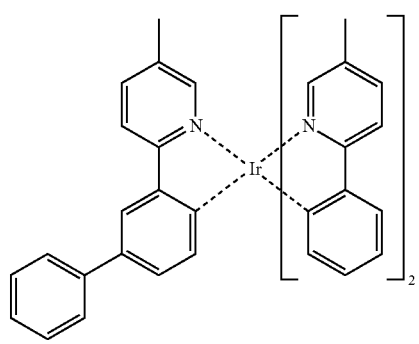
D-105
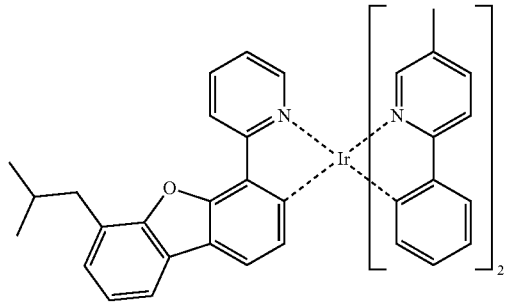
D-106
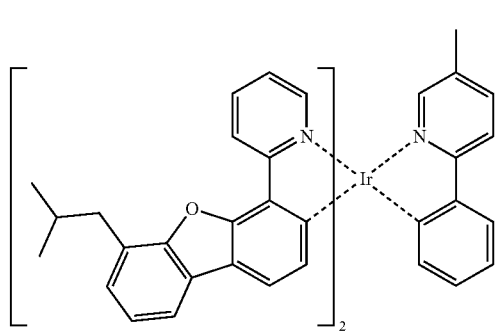
D-107
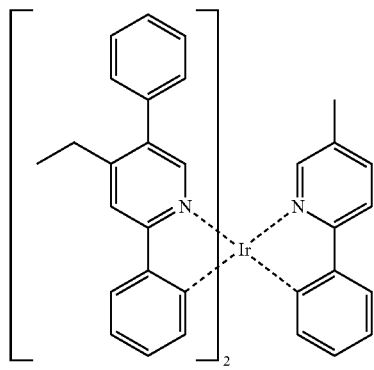
D-108
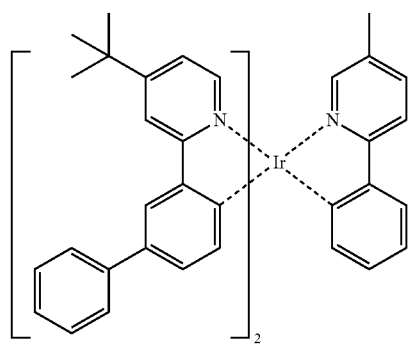
D-109
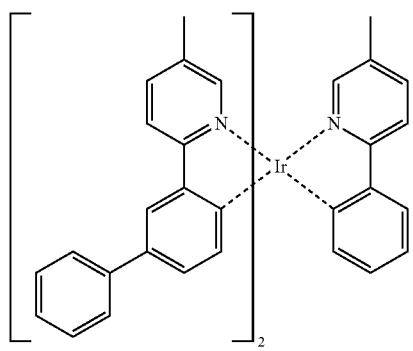
D-110
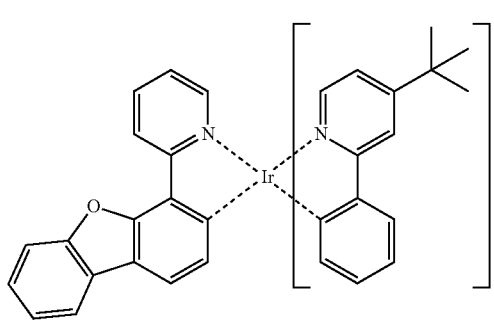

D-111
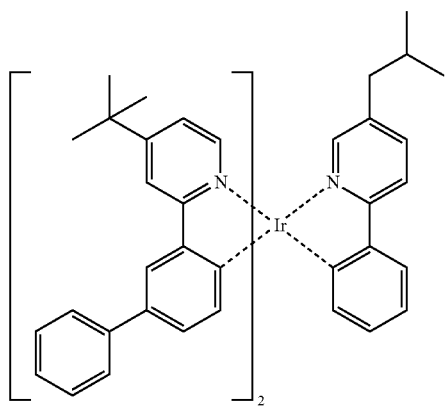
D-115
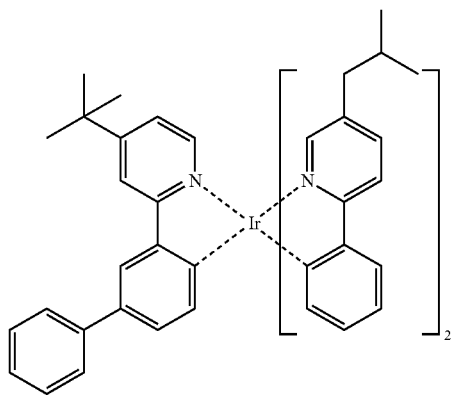
D-112
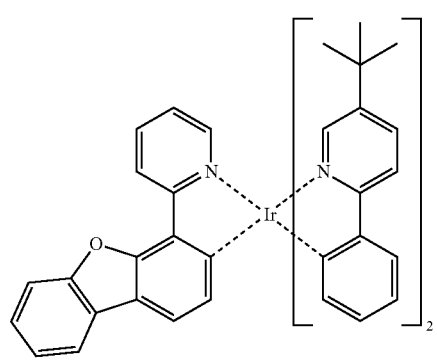
D-116
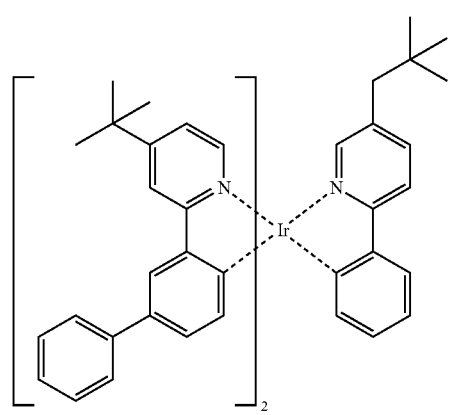
D-113
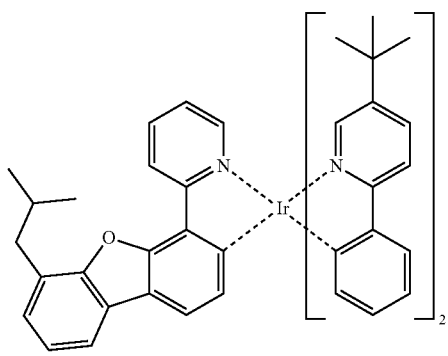
D-117
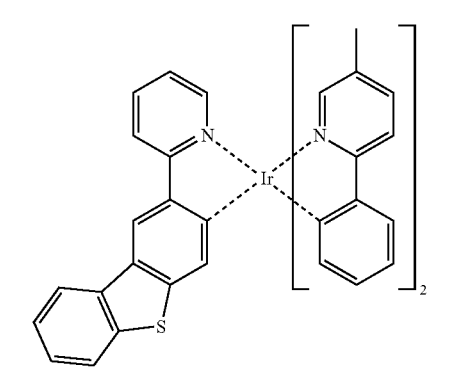
D-114
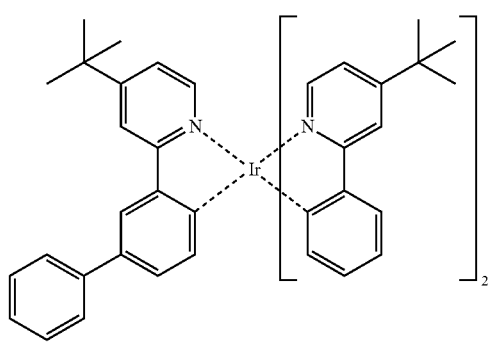
D-118
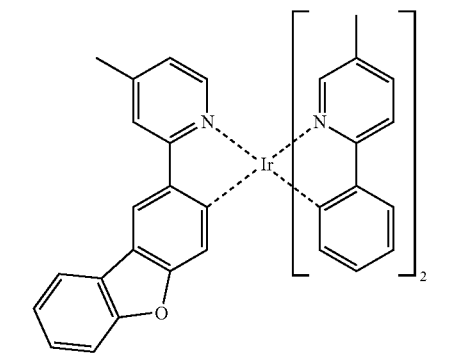

-continued
D-119
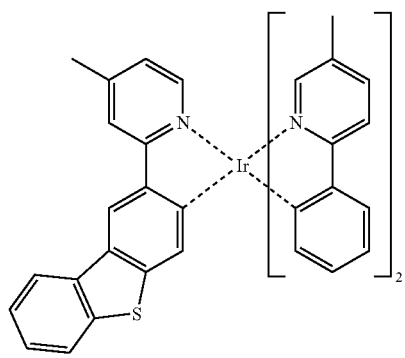
D-120
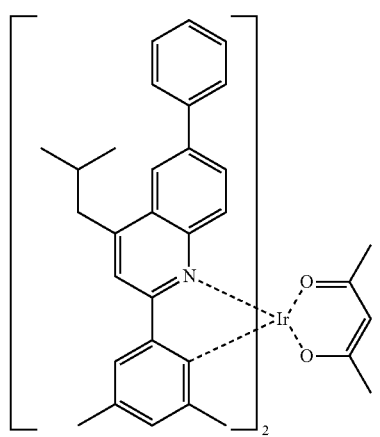
D-121
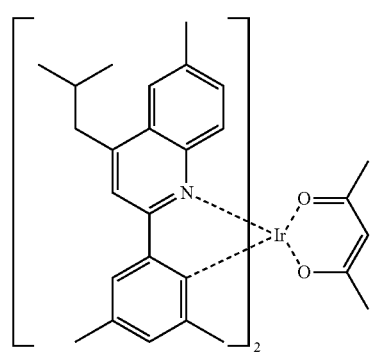
D-122
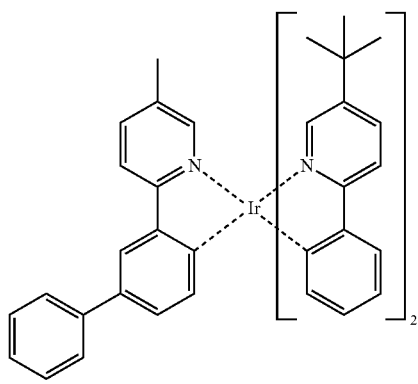
-continued
D-123
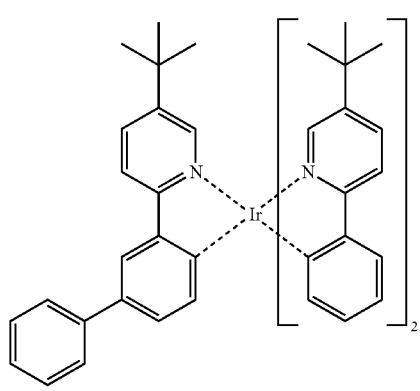
D-124
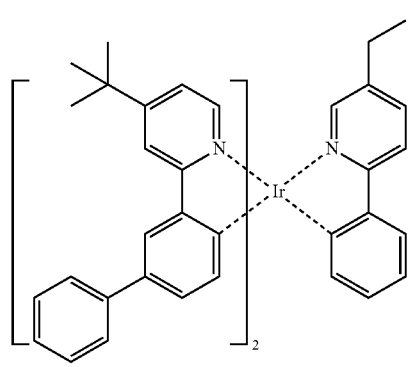
D-125
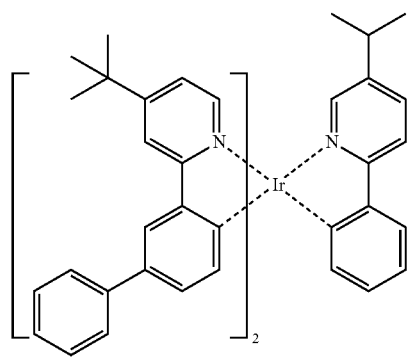
D-126
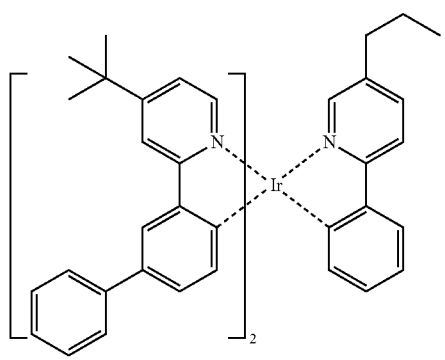

-continued
D-127
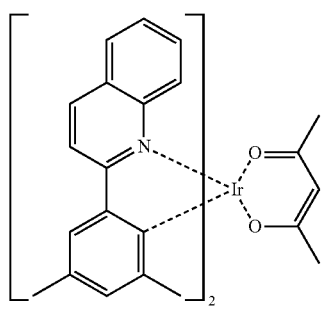
D-128
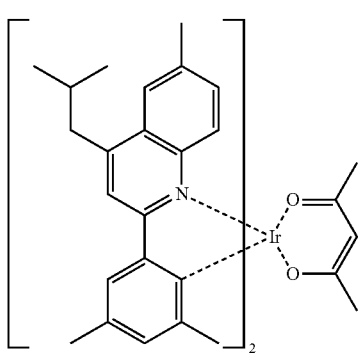
D-129
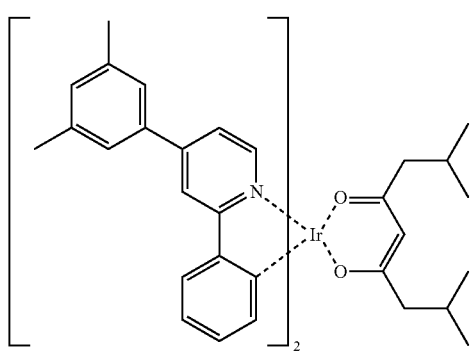
D-130
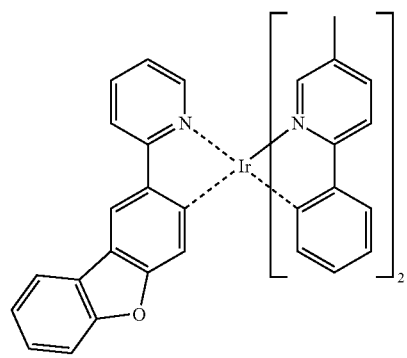
-continued
D-131
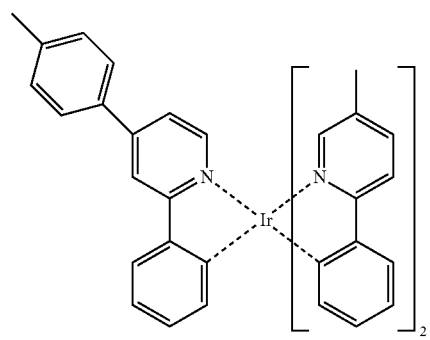
D-132
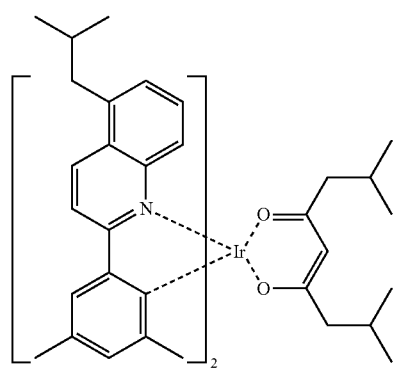
D-133
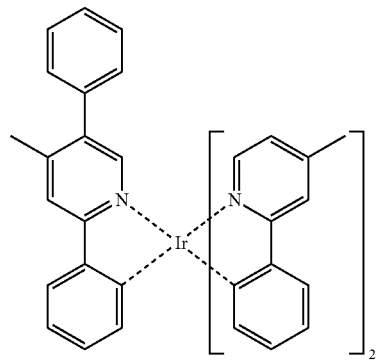
D-134
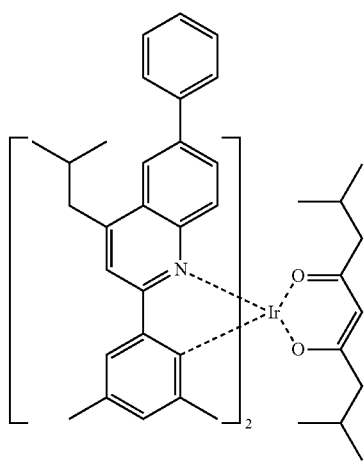

-continued
D-135
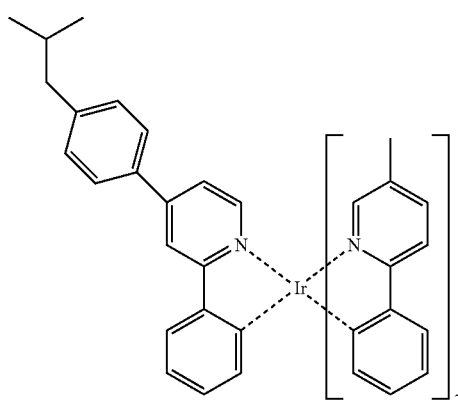
D-136
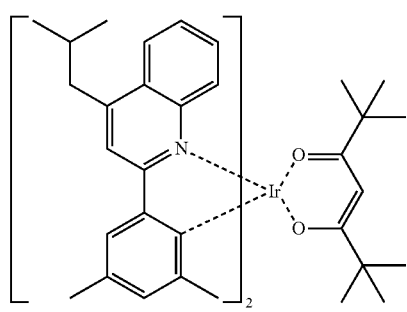
D-137
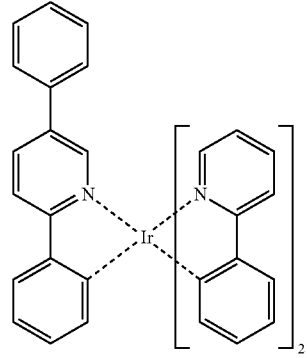
D-138
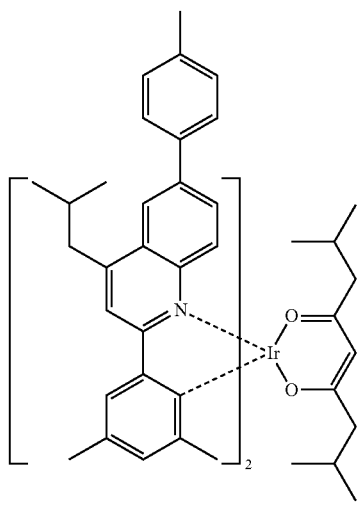
-continued
D-139
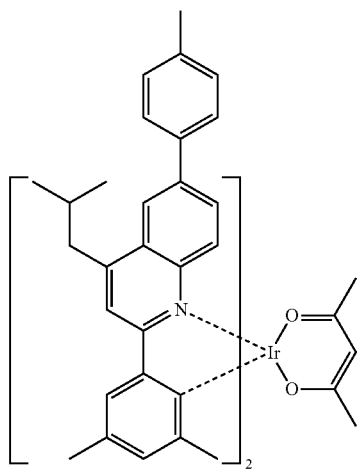
D-140
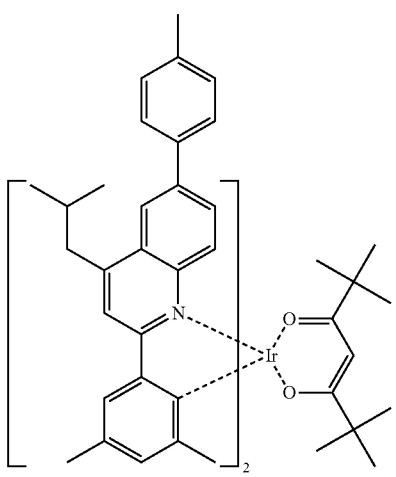
D-141
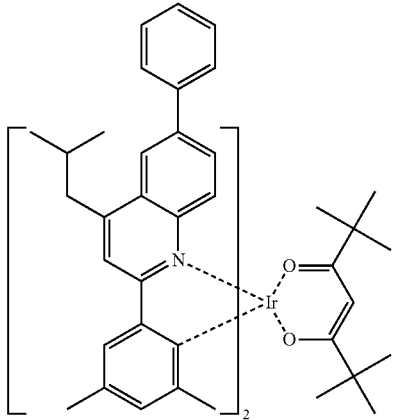

D-142

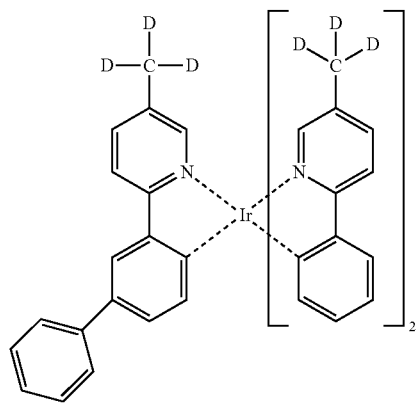

D-143

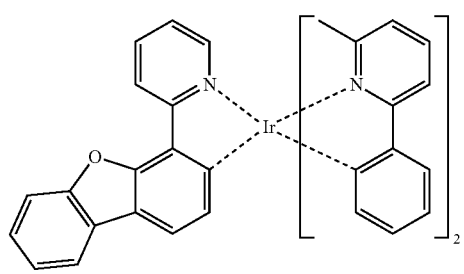

D-144

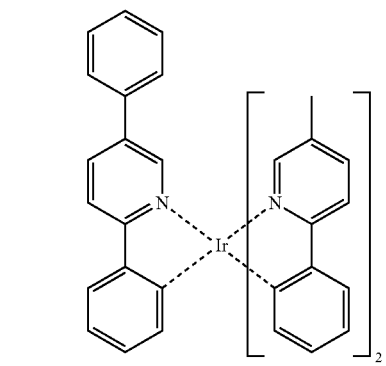

D-145

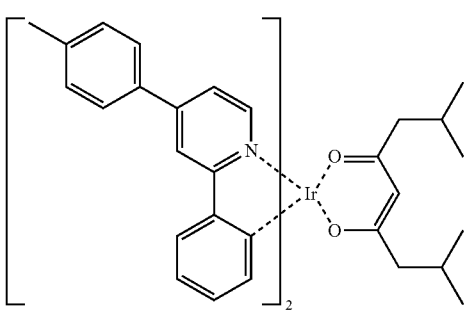

D-146

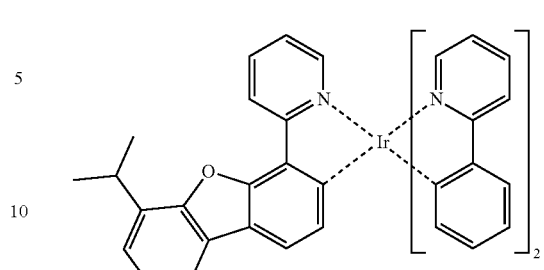

D-147

D-148

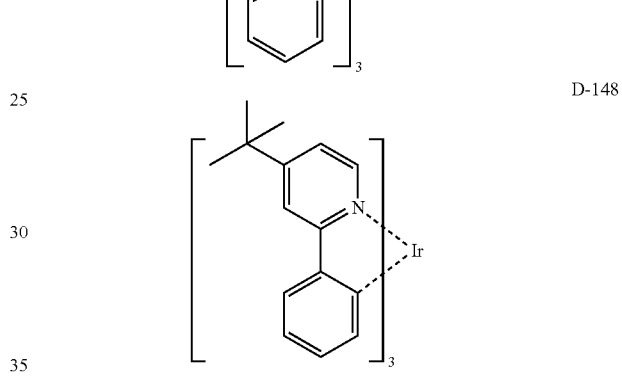

According to one embodiment of the present disclosure, the present disclosure provides an electron buffer material comprising the compound represented by formula 1. The electron buffer material indicates a material to control flow properties of an electron. For example, the electron buffer material may trap an electron, block an electron, or lower an energy barrier between an electron transport zone and a light-emitting layer. Specifically, the electron buffer material may be an electron buffer material of an organic electroluminescent device. The electron buffer material in an organic electroluminescent device may be used in the electron buffer layer, or may also be simultaneously used in other zones such as an electron transport zone or a light-emitting layer. The electron buffer material may be a mixture or a composition further comprising conventional materials generally used in producing an organic electroluminescent device.

The organic electroluminescent device of the present disclosure may comprise the compound of formula 1, and further comprise at least one compound selected from the group consisting of arylamine-based compounds and styrylarylamine-based compounds, simultaneously.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal. The organic layer may further comprise one or more additional light-emitting layers and a charge generating layer.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer, and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the preparation method of the compounds of the present disclosure, and the properties of the device comprising the compounds will be explained in detail with reference to the representative compounds of the present disclosure. However, the present disclosure is not limited by the following examples.

Example 1: Preparation of Compound C-39

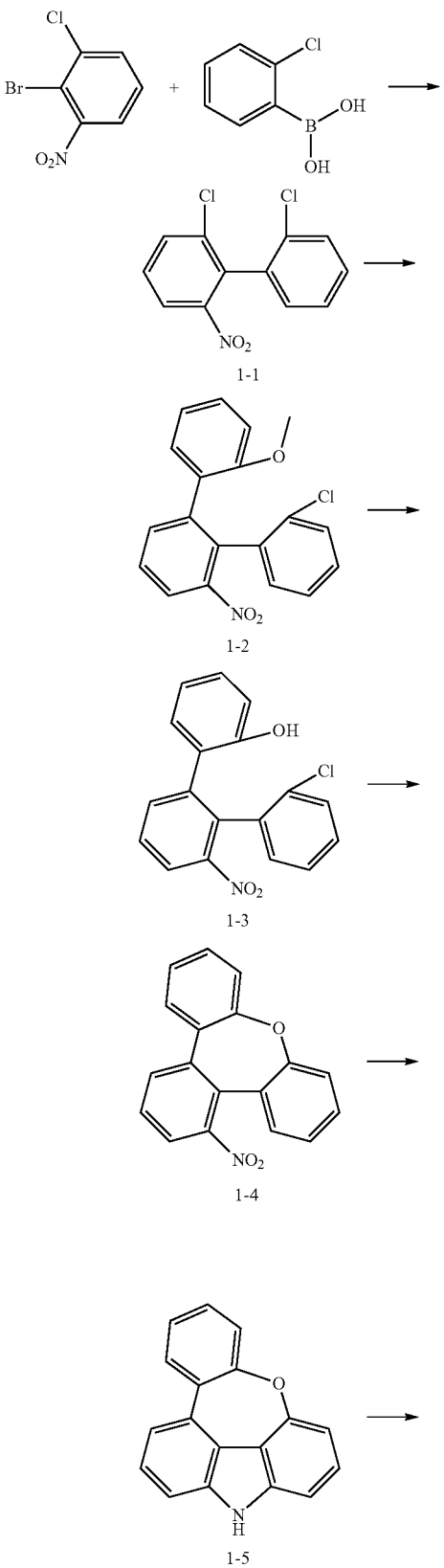

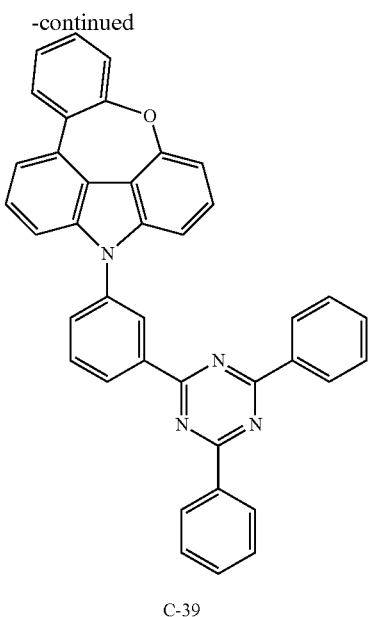

C-39

Preparation of Compound 1-1

2-bromo-1-chloro-3-nitrobenzene (56 g, 234 mmol), 2-chlorophenylboronic acid (74 g, 476 mmol), tetrakis(triphenylphosphine)palladium (O) (Pd(PPh$_3$)$_4$) (13 g, 11.9 mmol), 2M cesium carbonate (194 g, 596 mmol), toluene (1200 mL), and ethanol (300 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 1-1 (51 g, yield: 80%).

Preparation of Compound 1-2

Compound 1-1 (10 g, 37.3 mmol), 2-methoxyphenylboronic acid (6.8 g, 44.7 mmol), tris(dibenzylideneacetone)dipalladium (1.7 g, 1.86 mmol), cesium carbonate (30 g, 93.2 mmol), tricyclohexylphosphine (1 g, 3.73 mmol), toluene (200 mL), and dioxane (50 mL) were poured into a flask, and dissolved, and then refluxed for 4 hours. After completion of the reaction, an organic layer was extracted with ethyl acetate. The organic extract was dried on magnesium sulfate, and purified by column chromatography to obtain compound 1-2 (7.7 g, yield: 62%).

Preparation of Compound 1-3

Compound 1-2 (7.7 g, 22.7 mmol), boron tribromide (3.2 mL, 34.1 mmol), and methylene chloride (230 mL) were poured into a flask, and dissolved, and then reacted for 12 hours at room temperature. After the reaction was completed with a sodium hydrogen carbonate solution, an organic layer was extracted with methylene chloride. The organic extract was dried on magnesium sulfate, and then purified by column chromatography to obtain compound 1-3 (6.4 g, yield: 88%).

Preparation of Compound 1-4

Compound 1-3 (3.9 g, 12 mmol), potassium carbonate (0.8 g, 6 mmol), and dimethylformamide (60 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 1-4 (2 g, yield: 60%).

Preparation of Compound 1-5

Compound 1-4 (2 g, 6.9 mmol), triphenylphosphine (7.2 g, 27 mmol), and dichlorobenzene (25 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 1-5 (1.6 g, yield: 95%).

Preparation of Compound C-39

Compound 1-5 (1.6 g, 6.5 mmol), 2-(3-bromophenyl)-4,6-diphenyl-1,3,5-triazine (2.6 g, 6.8 mmol), palladium acetate (0.07 g, 0.32 mmol), sodium tert-butoxide (1.5 g, 16 mmol), 2-dichlorohexylphosphine-2',6'-dimethoxybiphenyl (0.26 g, 0.65 mmol), and o-xylene (30 mL) were poured into a flask, and dissolved, and then refluxed for 4 hours. After completion of the reaction, an organic layer was extracted with ethyl acetate. The organic extract was dried on magnesium sulfate, and purified by column chromatography to obtain compound C-39 (3.1 g, yield: 85%).

| Compound | MW | UV | PL | M.P. |
|---|---|---|---|---|
| C-39 | 564.63 | 374 nm | 443 nm | 237° C. |

Example 2: Preparation of Compound C-36

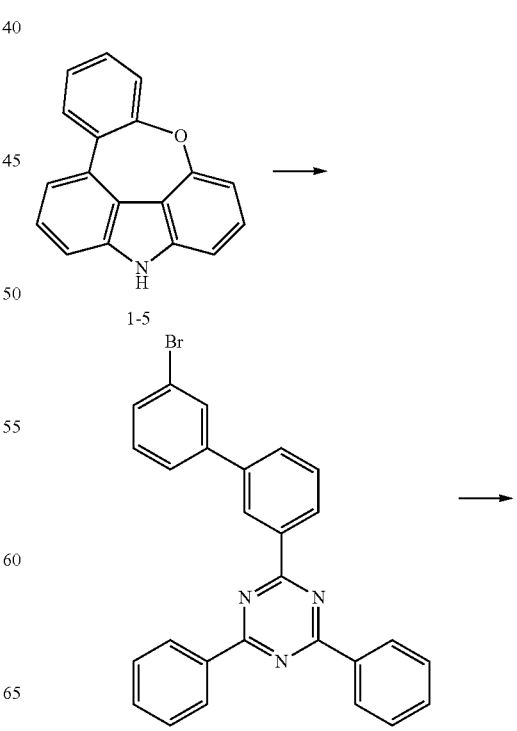

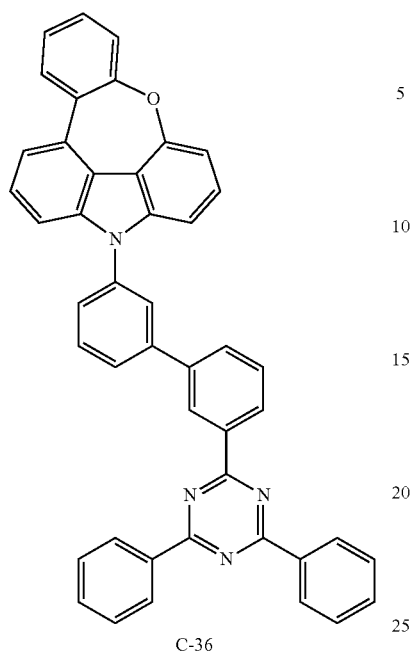

C-36

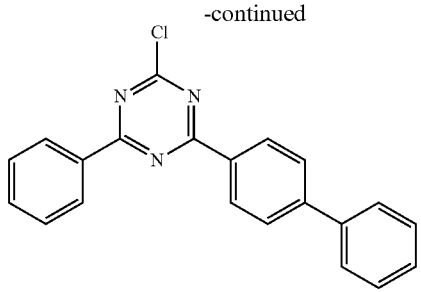

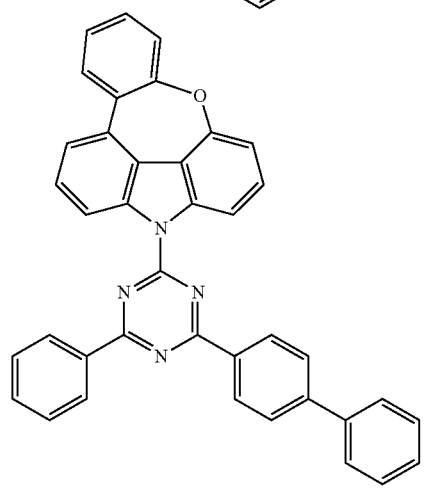

C-31

Compound 1-5 (5 g, 19 mmol), 2-(3-bromobiphenyl)-3-yl-4,6-diphenyl-1,3,5-triazine (9 g, 19 mmol), palladium acetate (0.2 g, 0.97 mmol), sodium tert-butoxide (4.6 g, 48 mmol), 2-dichlorohexylphosphine-2',6'-dimethoxybiphenyl (0.7 g, 1.9 mmol), and o-xylene (100 mL) were poured into a flask, and dissolved, and then refluxed for 7 hours. After completion of the reaction, an organic layer was extracted with ethyl acetate. The organic extract was dried on magnesium sulfate, and purified by column chromatography to obtain compound C-36 (8.2 g, yield: 65%).

| Compound | MW | UV | PL | M.P. |
|---|---|---|---|---|
| C-36 | 640.75 | 344 nm | 445 nm | 241° C. |

Example 3: Preparation of Compound C-31

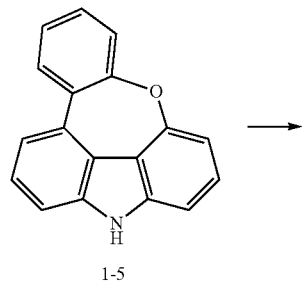

1-5

Compound 1-5 (3 g, 11 mmol), 2-[1,1'-biphenyl]-4-yl-4-chloro-6-phenyl-1,3,5-triazine (4.8 g, 14 mmol), 4-(dimethylamino)pyridine (0.7 g, 5.8 mmol), potassium carbonate (4 g, 29 mmol), and dimethylformamide (120 mL) were poured into a flask, dissolved, and heated to 120° C., and then reacted for 4 hours. After completion of the reaction, the mixture was added dropwise to distilled water, and the obtained solid was filtered. The filtrate was dried, and purified by column chromatography to obtain compound C-31 (6.4 g, yield: 97%).

| Compound | MW | UV | PL | M.P. |
|---|---|---|---|---|
| C-31 | 564.63 | 360 nm | 482 nm | 229° C. |

Example 4: Preparation of Compound C-94

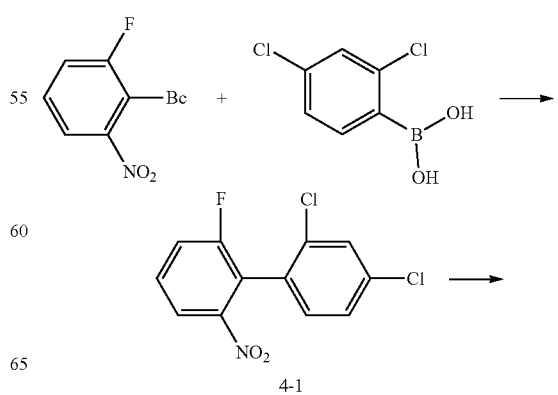

4-1

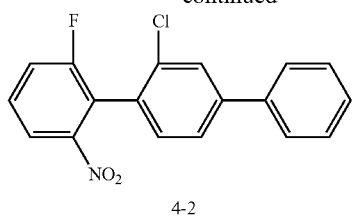

4-2

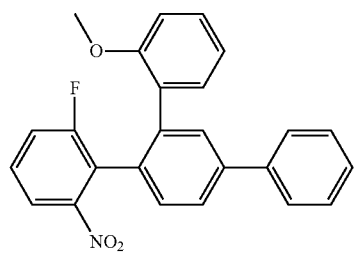

4-3

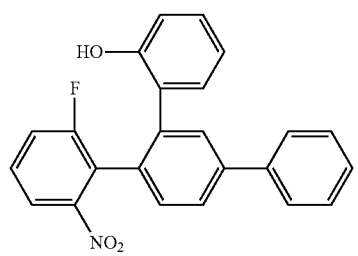

4-4

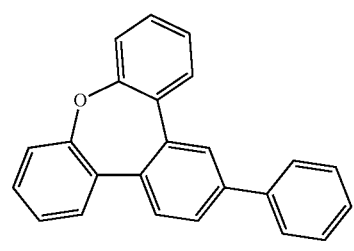

4-5

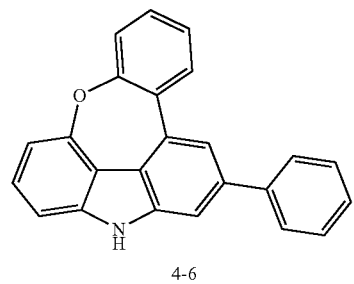

4-6

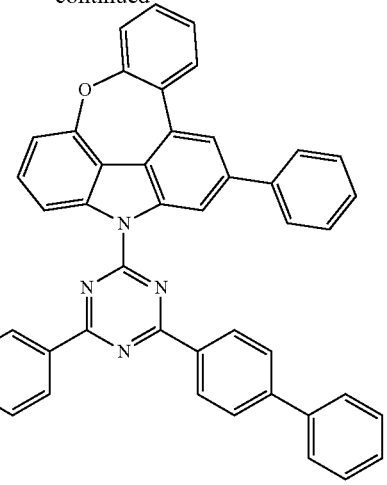

C-94

Preparation of Compound 4-1

2-bromo-1-fluoro-3-nitrobenzene (30 g, 136 mmol), (2,4-dichlorophenyl)boronic acid (27 g, 143 mmol), tetrakis (triphenylphosphine)palladium (O) (Pd(PPh$_3$)$_4$) (7.8 g, 6.8 mmol), 2M cesium carbonate (111 g, 341 mmol), toluene (680 mL), and ethanol (170 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 4-1 (32 g, yield: 84%).

Preparation of Compound 4-2

Compound 4-1 (15 g, 52 mmol), phenylboronic acid (7 g, 57 mmol), palladium acetate (0.3 g, 1.5 mmol), 2-dichlorohexylphosphine-2',6'-dimethoxybiphenyl (2.5 g, 6.3 mmol), 2M potassium phosphate (27 g, 131 mmol), toluene (260 mL), and dioxane (65 mL) were poured into a flask, and dissolved, and then refluxed for 3 hours. After completion of the reaction, an organic layer was extracted with ethyl acetate. The organic extract was dried on magnesium sulfate, and purified by column chromatography to obtain compound 4-2 (13 g, yield: 80%).

Preparation of Compound 4-3

Compound 4-2 (10 g, 32 mmol), 2-methoxyphenylboronic acid (7.3 g, 48 mmol), tris(dibenzylideneacetone) dipalladium (2.9 g, 3.2 mmol), cesium carbonate (31 g, 96 mmol), tricyclohexylphosphine (20 wt % in Toluene) (9 g, 6.4 mmol), toluene (160 mL), and dioxane (50 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 4-3 (3.3 g, yield: 26%).

Preparation of Compound 4-4

Compound 4-3 (3.3 g, 8.2 mmol), boron tribromide (12 mL, 12 mmol), and methylene chloride (80 mL) were poured into a flask, and dissolved, and then reacted for 12 hours at room temperature. After terminating the reaction by adding sodium hydrogen carbonate solution, an organic layer was extracted with methylene chloride. The organic extract was dried on magnesium sulfate, and purified by column chromatography to obtain compound 4-4 (3.1 g, yield: 99%).

Preparation of Compound 4-5

Compound 4-4 (3.1 g, 8.2 mmol), potassium carbonate (0.5 g, 4.1 mmol), and dimethylformamide (40 mL) were poured into a flask, and dissolved, and then refluxed for 4 hours. After completion of the reaction, an organic layer was extracted with ethyl acetate. The organic extract was dried on magnesium sulfate, and purified by column chromatography to obtain compound 4-5 (2.5 g, yield: 83%).

Preparation of Compound 4-6

Compound 4-5 (1.6 g, 6.9 mmol), triphenylphosphine (4.6 g, 17 mmol), and dichlorobenzene (15 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 4-6 (1.2 g, yield: 86%).

Preparation of Compound C-94

Compound 4-6 (1.2 g, 3.7 mmol), 2-[1,1'-biphenyl]-4-yl-4-chloro-6-phenyl-1,3,5-triazine (1.5 g, 4.4 mmol), 4-(dimethylamino)pyridine (0.2 g, 1.8 mmol), potassium carbonate (1.2 g, 9.3 mmol), and dimethylformamide (40 mL) were poured into a flask, dissolved, and heated to 120° ° C., and then refluxed for 4 hours. After completion of the reaction, the mixture was added dropwise to distilled water, and the obtained solid was filtered. The filtrate was dried, and purified by column chromatography to obtain compound C-94 (6.4 g, yield: 97%).

| Compound | MW | UV | PL | M.P. |
|---|---|---|---|---|
| C-94 | 640.73 | N.D | N.D | 315° C. |

[wherein N.D means "not detectable"]

Example 5: Preparation of Compound C-99

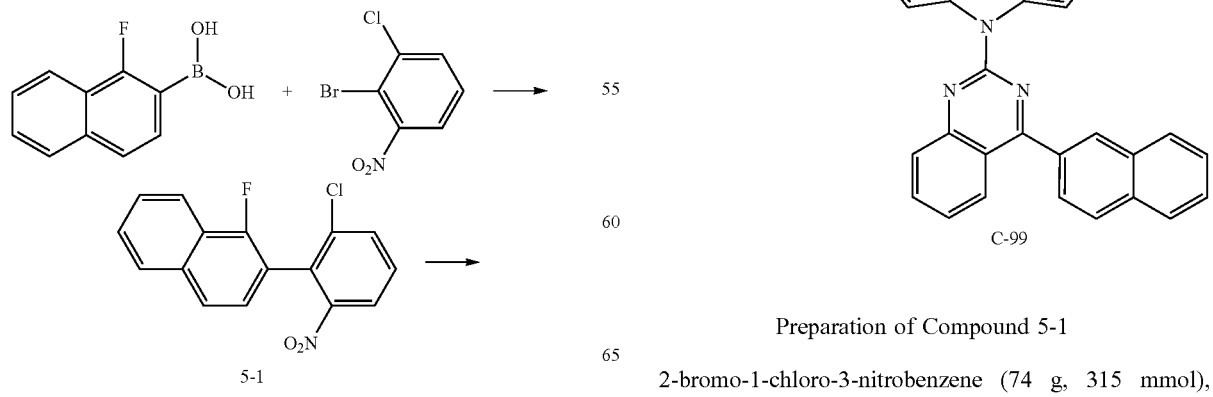

Preparation of Compound 5-1

2-bromo-1-chloro-3-nitrobenzene (74 g, 315 mmol), (1-fluoro-2-naphthalenyl)boronic acid (50 g, 263 mmol), tetrakis(triphenylphosphine)palladium (O) (Pd(PPh₃)₄) (15 g, 13 mmol), 2M cesium carbonate (257 g, 789 mmol), o-xylene (1600 mL), and ethanol (400 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 5-1 (36 g, yield: 47%).

Preparation of Compound 5-2

Compound 5-1 (34 g, 114 mmol), 2-methoxyphenylboronic acid (26 g, 172 mmol), tris(dibenzylideneacetone)dipalladium (10 g, 11 mmol), cesium carbonate (112 g, 343 mmol), tricyclohexylphosphine (20 wt % in Toluene) (32 g, 22 mmol), o-xylene (600 mL), and dioxane (170 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 5-2 (38 g, yield: 90%).

Preparation of Compound 5-3

Compound 5-2 (38 g, 102 mmol), boron tribromide (1M in MC) (153 mL, 153 mmol), and methylene chloride (1000 mL) were poured into a flask, and dissolved, and then reacted for 12 hours at room temperature. After terminating the reaction by adding sodium hydrogen carbonate solution, an organic layer was extracted with methylene chloride. The organic extract was dried on magnesium sulfate, and purified by column chromatography to obtain compound 5-3 (53 g).

Preparation of Compound 5-4

Compound 5-3 (53 g, 102 mmol), potassium carbonate (7 g, 51 mmol), and dimethylformamide (500 mL) were poured into a flask, and dissolved, and then refluxed for 4 hours. After completion of the reaction, an organic layer was extracted with ethyl acetate. The organic extract was dried on magnesium sulfate, and purified by column chromatography to obtain compound 5-4 (18 g, yield: 52%).

Preparation of Compound 5-5

Compound 5-4 (18 g, 53 mmol), triphenylphosphine (56 g, 214 mmol), and dichlorobenzene (180 mL) were poured into a flask, and dissolved, and then refluxed for 12 hours. After completion of the reaction, an organic layer was extracted with ethyl acetate. The organic extract was dried on magnesium sulfate, and purified by column chromatography to obtain compound 5-5 (9.5 g, yield: 59%).

Preparation of compound C-99

Compound 5-5 (5 g, 16 mmol), 2-chloro-4-(2-naphthalenyl)quinazoline (4.7 g, 16 mmol), cesium carbonate (5.3 g, 16 mmol), 4-(dimethylamino)pyridine (0.99 g, 8.1 mmol), and dimethyl sulfoxide (80 mL) were poured into a flask, dissolved, and heated to 90° C., and then reacted for 2 hours. After completion of the reaction, the mixture was added dropwise to methanol, and the obtained solid was filtered. The filtrate was dried, and purified by column chromatography to obtain compound C-99 (8.6 g, yield: 94%).

| Compound | MW | UV | PL | M.P. |
|---|---|---|---|---|
| C-99 | 561.63 | 344 nm | 566 nm | 230° C. |

Hereinafter, the luminescent properties of the organic light-emitting diode (OLED) device comprising the compound of the present disclosure will be explained in detail.

Device Example 1: Producing an OLED Device Comprising the Compound of the Present Disclosure as a Host An OLED device was produced by using the organic electroluminescent compound according to the present disclosure. A transparent electrode indium tin oxide (ITO) thin film (10 Ω/sq) on a glass substrate for an OLED device (Geomatec) was subjected to an ultrasonic washing with acetone, isopropanol, sequentially, and then was stored in isopropanol. The ITO substrate was then mounted on a substrate holder of a vacuum vapor deposition apparatus. Compound HIL-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HIL-2 was introduced into another cell of the vacuum vapor deposition apparatus, and was evaporated by applying an electric current to the cell, thereby forming a second hole injection layer having a thickness of 5 nm on the first hole injection layer. Compound HTL-1 was then introduced into another cell of the vacuum vapor deposition apparatus, and was evaporated by applying an electric current to the cell, thereby forming a first hole transport layer having a thickness of 10 nm on the second hole injection layer. Compound HTL-2 was then introduced into another cell of the vacuum vapor deposition apparatus, and was evaporated by applying an electric current to the cell, thereby forming a second hole transport layer having a thickness of 60 nm on the first hole transport layer. After forming the hole injection layer and the hole transport layer, a light-emitting layer was formed thereon as follows: Compound C-39 was introduced into one cell of the vacuum vapor deposition apparatus as a host, and compound D-71 was introduced into another cell as a dopant. The two materials were evaporated at a different rate, and the dopant was deposited in a doping amount of 3 wt % based on the total amount of the host and dopant to form a light-emitting layer having a thickness of 40 nm on the second hole transport layer. Compound ETL-1 and compound Liq were then introduced into another two cells, and evaporated at a rate of 1:1 to form an electron transport layer having a thickness of 30 nm on the light-emitting layer. After depositing compound Liq as an electron injection layer having a thickness of 2 nm on the electron transport layer, an Al cathode having a thickness of 80 nm was deposited by another vacuum vapor deposition apparatus. Thus, an OLED device was produced.

As a result, the produced OLED device showed a power efficiency of 26.9 lm/W at a driving voltage of 3.5 V, and a red emission having a luminance of 1,000 nits. When the early luminance is 100% at a constant current of 5,000 nits, the luminance after 16.7 hours was 95.7% (lifespan property).

Comparative Example 1: Producing an OLED Device Comprising a Conventional Compound as a Host An OLED device was produced in the same manner as in Device Example 1, except for using the following compound A as a host.

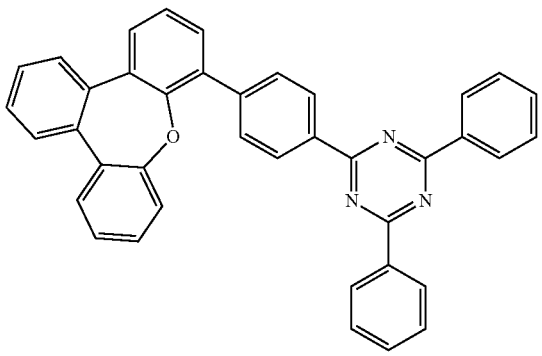

As a result, the produced OLED device showed a power efficiency of 17.9 lm/W at a driving voltage of 4.5 V, and a red emission having a luminance of 1,000 nits. When the early luminance is 100% at a constant current of 5,000 nits, the luminance after 16.7 hours was 19.9% (lifespan property).

Device Example 2-1: Producing an OLED Device Comprising the Compound of the Present Disclosure as a Host An OLED device was produced by using the organic electroluminescent compound according to the present disclosure. A transparent electrode indium tin oxide (ITO) thin film (10 Ω/sq) on a glass substrate for an OLED device (Geomatec) was subjected to an ultrasonic washing with acetone, ethanol, and distilled water, sequentially, and then was stored in isopropanol. The ITO substrate was then mounted on a substrate holder of a vacuum vapor deposition apparatus. Compound HIL-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HIL-2 was introduced into another cell of the vacuum vapor deposition apparatus, and was evaporated by applying an electric current to the cell, thereby forming a second hole injection layer having a thickness of 5 nm on the first hole injection layer. Compound HTL-1 was then introduced into the cell of the vacuum vapor deposition apparatus, and was evaporated by applying an electric current to the cell, thereby forming a first hole transport layer having a thickness of 10 nm on the second hole injection layer. Compound HTL-3 was then introduced into another cell of the vacuum vapor deposition apparatus, and was evaporated by applying an electric current to the cell, thereby forming a second hole transport layer having a thickness of 30 nm on the first hole transport layer. After forming the hole injection layer and the hole transport layer, a light-emitting layer was formed thereon as follows: Compound C-39 was introduced into one cell of the vacuum vapor deposition apparatus as a host, and compound D-13 was introduced into another cell as a dopant. The two materials were evaporated at a different rate, and the dopant was deposited in a doping amount of 15 wt % based on the total amount of the host and dopant to form a light-emitting layer having a thickness of 40 nm on the second hole transport layer. Compound ETL-1 and compound Liq were then introduced into another two cells, and evaporated at a rate of 4:6 to form an electron transport layer having a thickness of 35 nm on the light-emitting layer. After depositing compound Liq as an electron injection layer having a thickness of 2 nm on the electron transport layer, an Al cathode having a thickness of 80 nm was deposited by another vacuum vapor deposition apparatus. Thus, an OLED device was produced. Each of the materials used for producing the OLED device was purified by vacuum sublimation at $10^{-6}$ torr.

Device Examples 2-2 and 2-3: Producing an OLED Device Comprising the Compound of the Present Disclosure as a Host In Device Examples 2-2 and 2-3, OLED devices were produced in the same manner as in Device Example 2-1, except for using compound C-36 and compound C-31, respectively, as a host.

Comparative Example 2: Producing an OLED Device Comprising a Conventional Compound as a Host An OLED device was produced in the same manner as in Device Example 2-1, except for the following: A light-emitting layer having a thickness of 40 nm was deposited on the second hole transport layer by using compound CBP as a host and compound D-13 as a dopant; compound Balq was deposited as a hole blocking layer having a thickness of 10 nm; and thereafter, compound ETL-1 and compound Liq were introduced into another two cells, and evaporated at a rate of 4:6 to form an electron transport layer having a thickness of 25 nm.

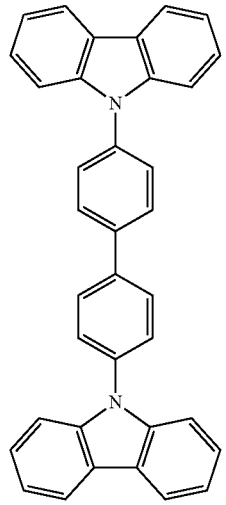

CBP

-continued

Balq

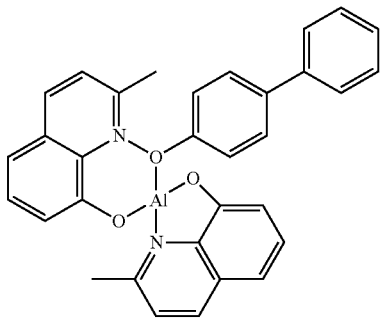

The driving voltage, the power efficiency, and the CIE color coordinate at the luminance of 1,000 nits of the OLED devices produced in Device Examples 2-1 to 2-3 and Comparative Example 2 are provided in Table 1 below.

TABLE 1

|  | Host | Voltage [V] | Power Efficiency [lm/W] | Color Coordinate (x, y) |
| --- | --- | --- | --- | --- |
| Device Example 2-1 | C-39 | 3.3 | 27.0 | 0.311, 0.656 |
| Device Example 2-2 | C-36 | 4.0 | 29.1 | 0.303, 0.662 |
| Device Example 2-3 | C-31 | 3.4 | 31.2 | 0.306, 0.659 |
| Comparative Example 2 | CBP | 5.8 | 23.1 | 0.295, 0.665 |

From Device Examples 1 and 2-1 to 2-3, and Comparative Examples 1 and 2 above, it can be seen that the OLED device using the compound of the present disclosure as a host not only has excellent luminance property, but also induces the increase in power efficiency by lowering the driving voltage to improve the power consumption, compared to the OLED device using the conventional luminescent material.

Device Example 3-1: Producing an OLED Device Comprising the Compound of the Present Disclosure as a First Host Compound An OLED device was produced in the same manner as in Device Example 1, except that a thickness of the second hole transport layer lowered to 30 nm, and a light-emitting layer and an electron transport layer were deposited as follows: Compound C-39 (a first host) and compound B-8 (a second host) were introduced into two cells of the vacuum vapor deposition apparatus, respectively, as a host. Compound D-87 was introduced into another cell as a dopant. The two host compounds were evaporated at different rate of 1:2, while the dopant was evaporated at a different rate from the host compounds, so that the dopant was deposited in a doping amount of 10 wt % based on the total amount of the host and dopant to form a light-emitting layer having a thickness of 40 nm on the second hole transport layer. Thereafter, compound ETL-1 and compound Liq were then introduced into another two cells, and evaporated at a rate of 4:6 to form an electron transport layer having a thickness of 35 nm on the light-emitting layer.

Device Examples 3-2 and 3-3: Producing an OLED Device Comprising the Compound of the Present Disclosure as a First Host Compound In Device Examples 3-2 and 3-3, OLED devices were produced in the same manner as in Device Example 3-1, except for using compound C-36 and compound C-31, respectively, as a first host compound.

Device Examples 3-4 to 3-6: Producing an OLED Device Comprising the Compound of the Present Disclosure as a Host Compound In Device Examples 3-4 to 3-6, OLED devices were produced in the same manner as in Device Example 3-1, except for using only compound C-39, compound C-36, and compound C-31, respectively, as a host in the light-emitting layer instead of the first and second host compounds.

The driving voltage, current and the color of the light emission at the luminance of 1,000 cd/m$^2$ of the OLED devices produced in Device Examples 3-1 to 3-6 are provided in Table 2 below.

TABLE 2

|  | Host | | Voltage (V) | Current (mA/cm$^2$) | Color |
| --- | --- | --- | --- | --- | --- |
|  | First Host | Second Host | | | |
| Device Example 3-1 | C-39 | B-8 | 3.4 | 1.62 | Green |
| Device Example 3-2 | C-36 | B-8 | 3.5 | 1.66 | Green |
| Device Example 3-3 | C-31 | B-8 | 3.3 | 1.60 | Green |
| Device Example 3-4 | C-39 | | 3.1 | 2.25 | Green |
| Device Example 3-5 | C-36 | | 3.6 | 1.80 | Green |
| Device Example 3-6 | C-31 | | 3.2 | 2.00 | Green |

From Devices Examples 3-1 to 3-6 above, it can be seen that the OLED device comprising the compound of the present disclosure as any one of the plurality of host compounds as well as comprising the compound of the present disclosure as a sole host have the excellent luminance property.

Device Example 4-1: Producing a Blue Light-Emitting OLED Device Comprising the Compound of the Present Disclosure as an Electron Buffer Material An OLED device was produced as follows: A transparent electrode indium tin oxide (ITO) thin film (10 Ω/sq) on a glass substrate for an OLED device (Geomatec) was subjected to an ultrasonic washing with acetone, ethanol, and distilled water, sequentially, and then was stored in isopropanol. The ITO substrate was then mounted on a substrate holder of a vacuum vapor deposition apparatus. Compound HIL-1 was introduced into a cell of the vacuum vapor deposition apparatus, and then the pressure in the chamber of the apparatus was controlled to 10$^{-7}$ torr. Thereafter, an electric current was applied to the cell to evaporate the above-introduced material, thereby forming a first hole injection layer having a thickness of 60 nm on the ITO substrate. Next, compound HIL-2 was introduced into another cell of the vacuum vapor deposition apparatus, and was evaporated by applying an electric current to the cell, thereby forming a second hole injection layer having a thickness of 5 nm on the first hole injection layer. Compound HTL-1 was then introduced into another cell of the vacuum vapor deposition apparatus, and was evaporated by applying an electric current to the cell, thereby forming a first hole transport layer having a thickness of 20 nm on the second hole injection layer. Compound HTL-4 was then introduced into another cell of the vacuum vapor deposition apparatus, and was evaporated by applying an electric current to the cell, thereby forming a second hole transport layer having a thickness of 5 nm on the first hole transport layer. After forming the hole injection layer and the hole transport layer, a light-emitting layer was formed thereon as follows: Compound BH-1 was introduced into one cell of the vacuum vapor deposition apparatus as a host, and compound BD-1 was introduced into another cell as a dopant. The two materials were evaporated at a different rate, and the dopant was deposited in a doping amount of 2 wt % based on the total amount of the host and dopant to form a light-emitting layer having a thickness of 20 nm on the second hole transport layer. Compound C-36 as an electron buffer material was deposited as an electron buffer layer having a thickness of 5 nm on the light-emitting layer. Compound ETL-2 was introduced into one cell and compound Liq was introduced into another cell, and evaporated at the same rate and deposited in a doping amount of 50 wt % to form an electron transport layer having a thickness of 25 nm on the electron buffer layer. After depositing compound Liq as an electron injection layer having a thickness of 2 nm on the electron transport layer, an Al cathode having a thickness of 80 nm was deposited by another vacuum vapor deposition apparatus. Thus, an OLED device was produced. Each of the materials used for producing the OLED device was purified by vacuum sublimation at $10^{-6}$ torr.

Device Examples 4-2 to 4-4: Producing a Blue Light-Emitting OLED Device Comprising the Compound of the Present Disclosure as an Electron Buffer Material In Device Examples 4-2 to 4-4, OLED devices were produced in the same manner as in Device Example 4-1, except for using compound C-39, compound C-31, and compound C-94, respectively, as an electron buffer material.

The driving voltage, luminous efficiency and the color of the light emission at the luminance of 1,000 nits of the OLED devices produced in Device Examples 4-1 to 4-4 are provided in Table 3 below.

TABLE 3

|  | Electron Buffer Material | Voltage (V) | Luminous Efficiency (cd/A) | Color |
| --- | --- | --- | --- | --- |
| Device Example 4-1 | C-36 | 3.6 | 6.7 | Blue |
| Device Example 4-2 | C-39 | 3.8 | 5.9 | Blue |
| Device Example 4-3 | C-31 | 3.7 | 6.4 | Blue |
| Device Example 4-4 | C-94 | 3.6 | 6.8 | Blue |

From Devices Examples 4-1 to 4-4 above, it can be seen that the OLED device comprising the compound of the present disclosure as an electron buffer material has low driving voltage and excellent luminous efficiency.

The compounds used in the Devices Examples and the Comparative Examples are provided in Table 4 below.

TABLE 4

Hole Injection Layer/
Hole Transport Layer

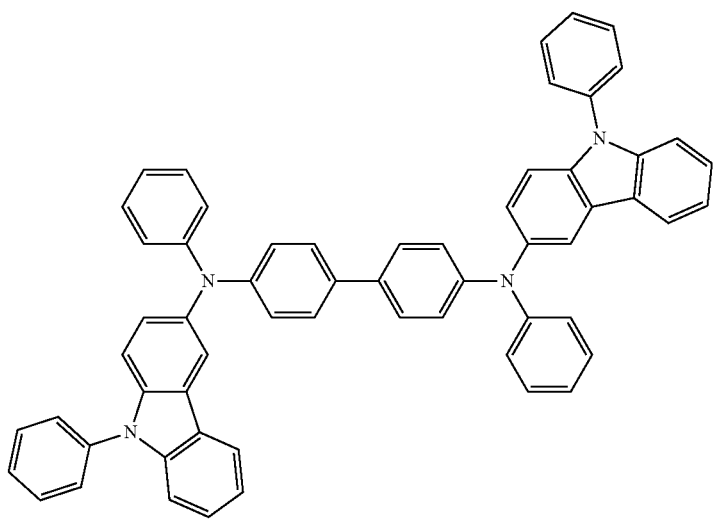 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

HIL-1

TABLE 4-continued
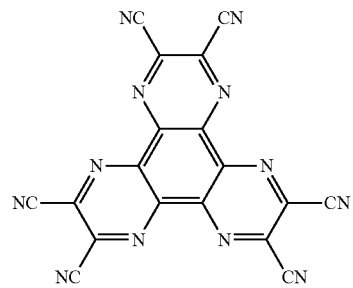 [SMILES: N#Cc1nc2c3nc(C#N)c(C#N)nc3c3nc(C#N)c(C#N)nc3c2nc1C#N]
HIL-2
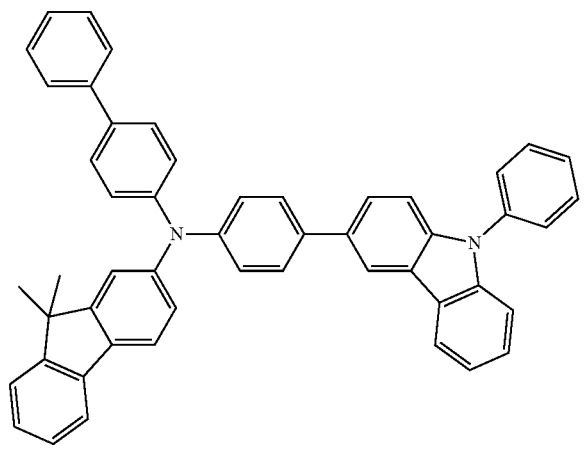 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HTL-1
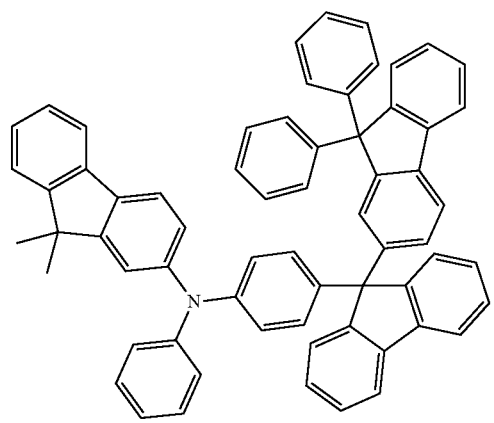 [SMILES: CC1(C)c2ccccc2-c2ccc(N(c3ccccc3)c3ccc(C4(c5ccc6c(c5)C(c5ccccc5)(c5ccccc5)c5ccccc5-6)c5ccccc5-c5ccccc54)cc3)cc21]
HTL-2

TABLE 4-continued
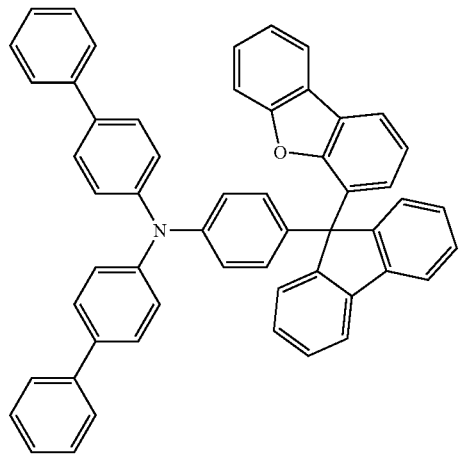 [SMILES: c1ccc(-c2ccc(N(c3ccc(-c4ccccc4)cc3)c3ccc(C4(c5cccc6c5oc5ccccc56)c5ccccc5-c5ccccc54)cc3)cc2)cc1]
HTL-3
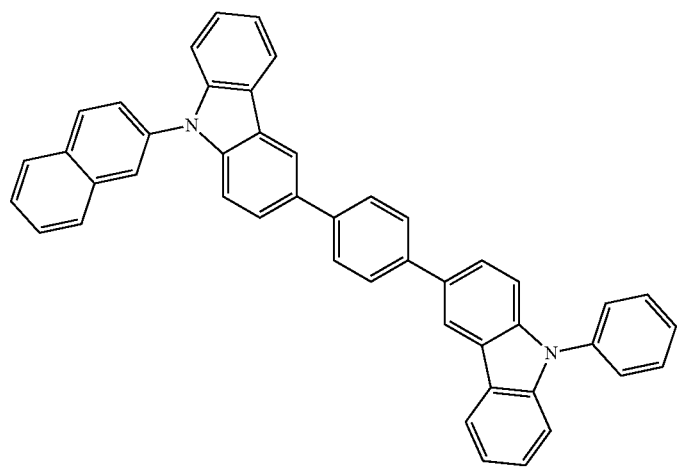 [SMILES: c1ccc(-n2c3ccccc3c3cc(-c4ccc(-c5ccc6c(c5)c5ccccc5n6-c5ccc6ccccc6c5)cc4)ccc32)cc1]
HTL-4
Light-Emitting Layer
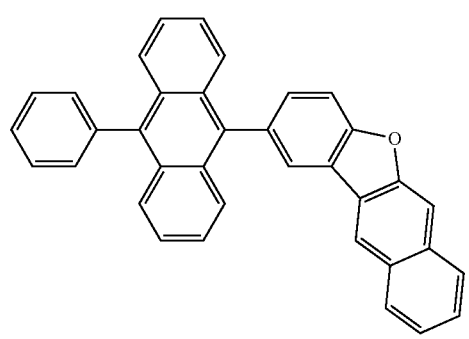 [SMILES: c1ccc(-c2c3ccccc3c(-c3ccc4oc5cc6ccccc6cc5c4c3)c3ccccc23)cc1]
BH-1

TABLE 4-continued
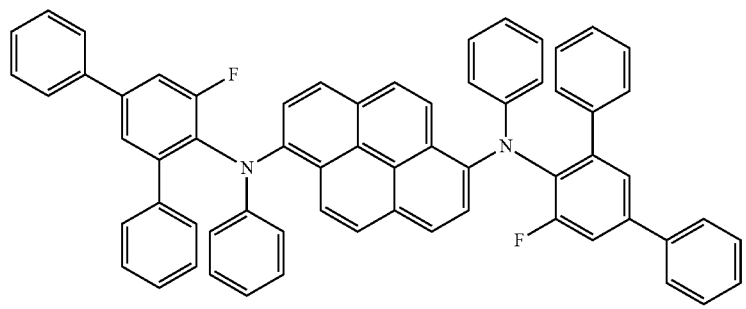 [SMILES: Fc1cc(-c2ccccc2)cc(-c2ccccc2)c1N(c1ccccc1)c1ccc2ccc3c(N(c4ccccc4)c4c(F)cc(-c5ccccc5)cc4-c4ccccc4)ccc4ccc1c2c43]
BD-1
Electron Transport Layer/Electron Injection Layer
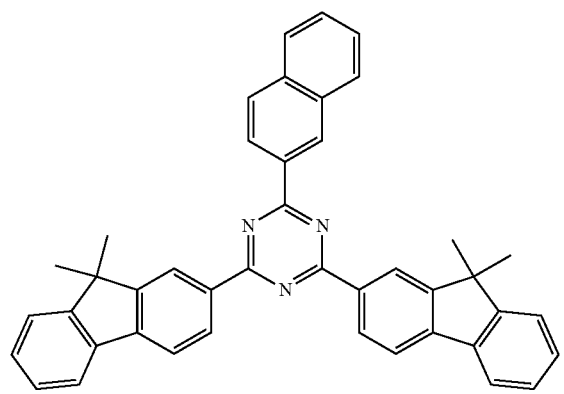 [SMILES: CC1(C)c2ccccc2-c2ccc(-c3nc(-c4ccc5c(c4)C(C)(C)c4ccccc4-5)nc(-c4ccc5ccccc5c4)n3)cc21]
ETL-1
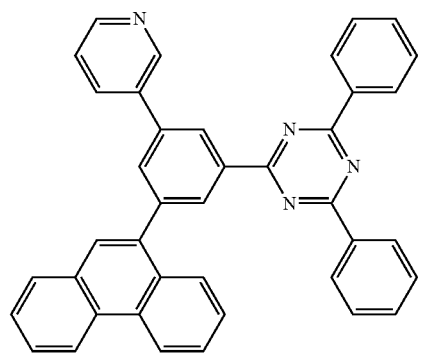 [SMILES: c1ccc(-c2nc(-c3ccccc3)nc(-c3cc(-c4cccnc4)cc(-c4cc5ccccc5c5ccccc45)c3)n2)cc1]
ETL-2
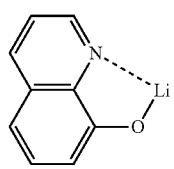
Liq

The invention claimed is:
1. An organic electroluminescent compound represented by the following formula 1:

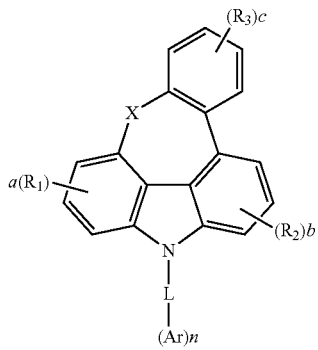

wherein
X represents O or S;
L represents a single bond, a substituted or unsubstituted (C6-C30)arylene, or a substituted or unsubstituted (3- to 30-membered)heteroarylene;
Ar represents a substituted or unsubstituted (C6-C30)aryl, a substituted or unsubstituted (3- to 30-membered) heteroaryl, or —$NR_{11}R_{12}$;
$R_1$ to $R_3$, each independently, represent hydrogen, deuterium, a substituted or unsubstituted (C1-C10)alkyl, a substituted or unsubstituted (C6-C30)aryl, a substituted or unsubstituted (3- to 30-membered)heteroaryl, or —$NR_{13}R_{14}$; or are linked to adjacent $R_1$, $R_2$ and $R_3$, respectively, to form a substituted or unsubstituted, mono- or polycyclic, (C3-C30) alicyclic or aromatic ring, or the combination thereof, whose carbon atom(s) may be replaced with at least one heteroatom selected from nitrogen, oxygen, and sulfur;
$R_{11}$ to $R_{14}$, each independently, represent a substituted or unsubstituted (C1-C10)alkyl, a substituted or unsubstituted (C6-C30)aryl, or a substituted or unsubstituted (3- to 30-membered)heteroaryl;
n represents 1 or 2; where if n represents 2, each Ar may be the same or different;
a and b, each independently, represent an integer of 1 to 3; c represents an integer of 1 to 4; where if a to c, each independently, represent an integer of 2 or more, each of $R_1$ to $R_3$ may be the same or different; and
the heteroaryl(ene) contains at least one heteroatom selected from B, N, O, S, Si, and P.

2. The organic electroluminescent compound according to claim 1, wherein the substituents of the substituted aryl(ene), the substituted heteroaryl(ene), the substituted alkyl, and the substituted mono- or polycyclic, alicyclic or aromatic ring, or the combination thereof, in L, Ar, $R_1$ to $R_3$, and $R_{11}$ to $R_{14}$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered) heteroaryl unsubstituted or substituted with a (C1-C30)alkyl or a (C6-C30)aryl; a (C6-C30)aryl unsubstituted or substituted with a (3- to 30-membered)heteroaryl; a tri(C1-C30) alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl.

3. The organic electroluminescent compound according to claim 1, wherein
L represents a single bond, a substituted or unsubstituted (C6-C25)arylene, or a substituted or unsubstituted (5- to 25-membered)heteroarylene;
Ar represents a substituted or unsubstituted (C6-C25)aryl, a substituted or unsubstituted (5- to 25-membered) heteroaryl, or —$NR_{11}R_{12}$;
$R_1$ to $R_3$, each independently, represent hydrogen, a substituted or unsubstituted (C6-C25)aryl, a substituted or unsubstituted (5- to 25-membered)heteroaryl, or —$NR_{13}R_{14}$; or are linked to adjacent $R_1$, $R_2$ and $R_3$, respectively, to form a substituted or unsubstituted, mono- or polycyclic, (C5-C25) alicyclic or aromatic ring, or the combination thereof, whose carbon atom(s) may be replaced with at least one heteroatom selected from nitrogen, oxygen, and sulfur;
$R_{11}$ to $R_{14}$, each independently, represent a substituted or unsubstituted (C6-C25)aryl, or a substituted or unsubstituted (5- to 25-membered)heteroaryl; and
a to c, each independently, represent 1 or 2.

4. The organic electroluminescent compound according to claim 1, wherein
L represents a single bond, a substituted or unsubstituted (C6-C18)arylene, or a substituted or unsubstituted (5- to 18-membered)heteroarylene;
Ar represents a substituted or unsubstituted (C6-C18)aryl, a substituted or unsubstituted (5- to 18-membered) heteroaryl, or —$NR_{11}R_{12}$;
$R_1$ to $R_3$, each independently, represent hydrogen, a substituted or unsubstituted (C6-C18)aryl, a substituted or unsubstituted (5- to 18-membered)heteroaryl, or —$NR_{13}R_{14}$; or are linked to adjacent $R_1$, $R_2$ and $R_3$, respectively, to form an unsubstituted, mono- or polycyclic, (C5-C18) aromatic ring;
$R_{11}$ to $R_{14}$, each independently, represent a substituted or unsubstituted (C6-C18)aryl; and
a to c, each independently, represent 1 or 2.

5. The organic electroluminescent compound according to claim 1, wherein the compound represented by formula 1 is selected from the group consisting of:

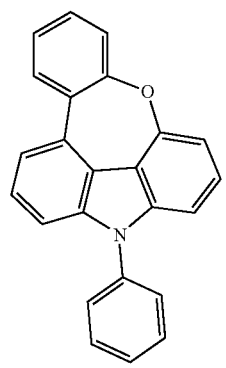

C-1

-continued
C-2
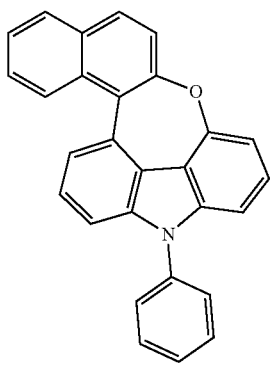
C-3
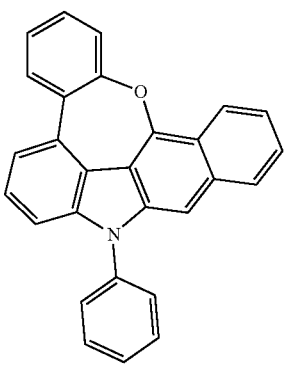
C-4
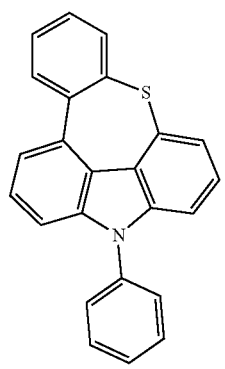
C-5
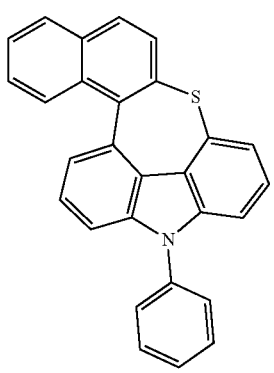
-continued
C-6
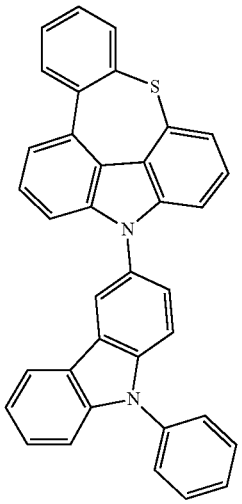
C-7
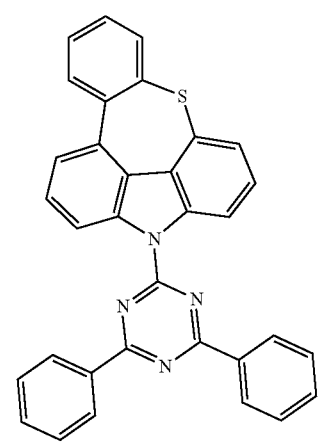
C-8
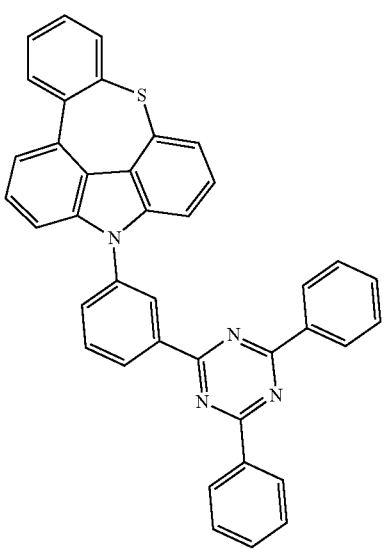

-continued
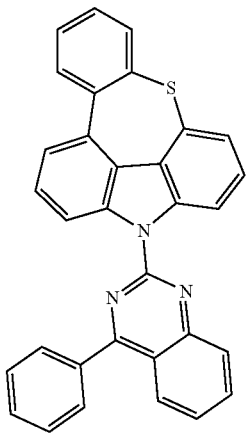
C-9
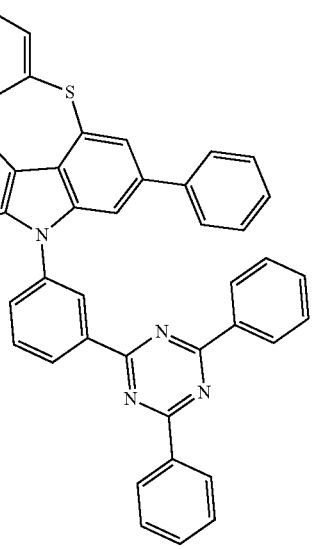
C-10
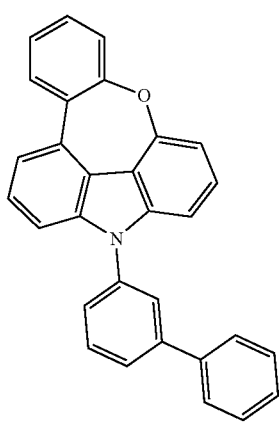
C-11
-continued
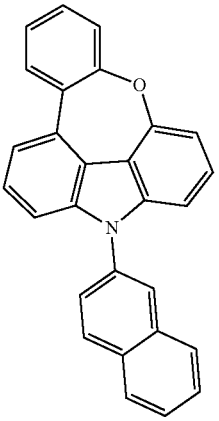
C-12
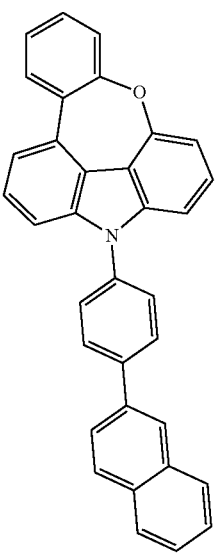
C-13
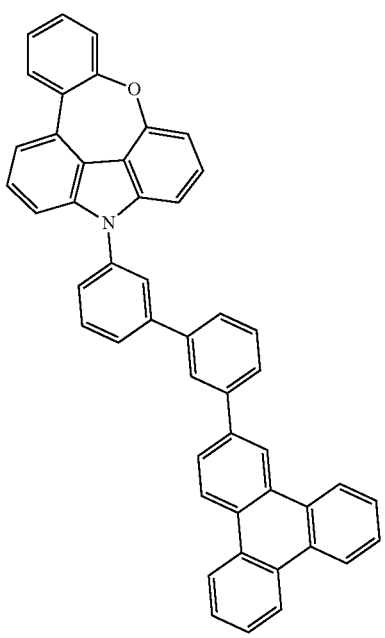
C-14

C-15
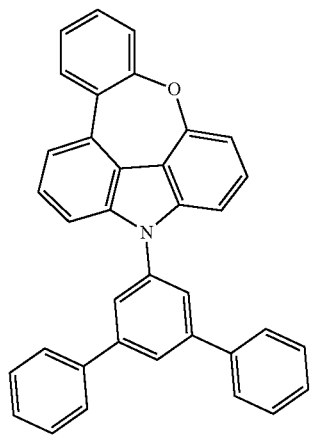
C-16
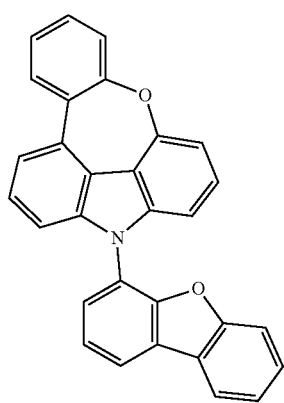
C-17
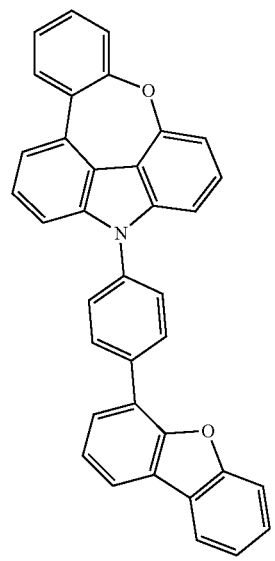
C-18
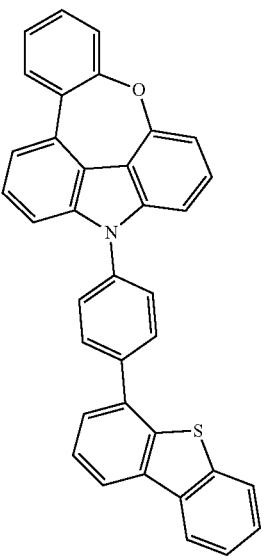
C-19
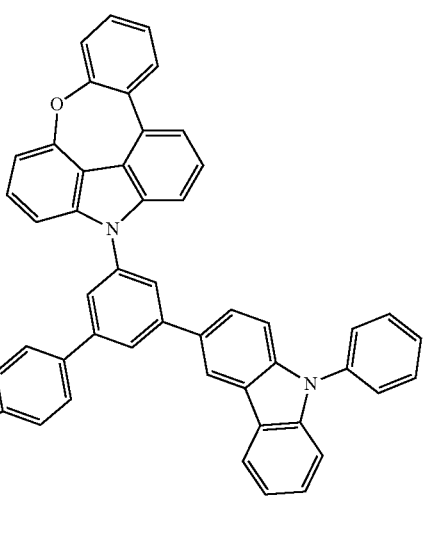
C-20
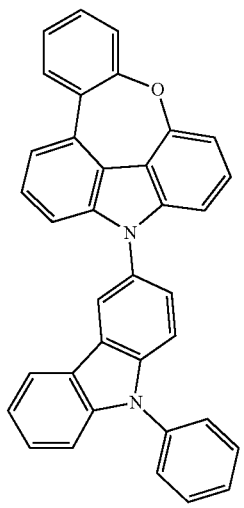

C-21
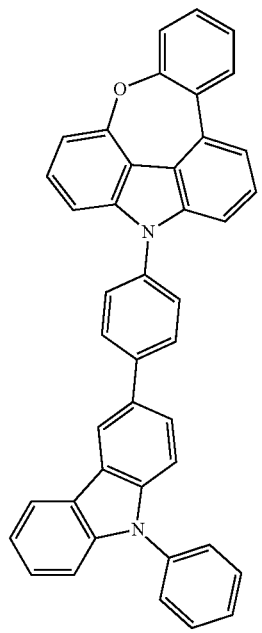
C-22
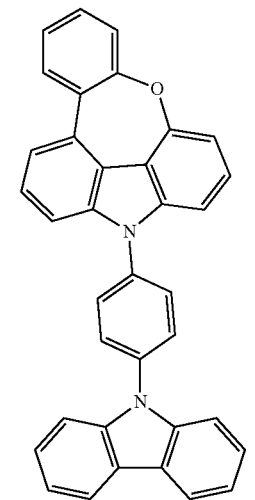
C-23
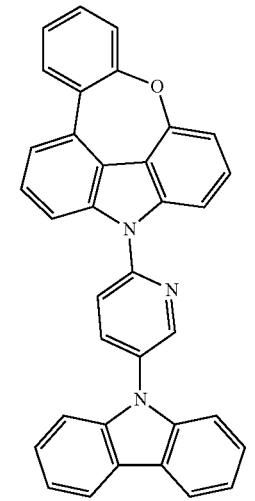
C-24
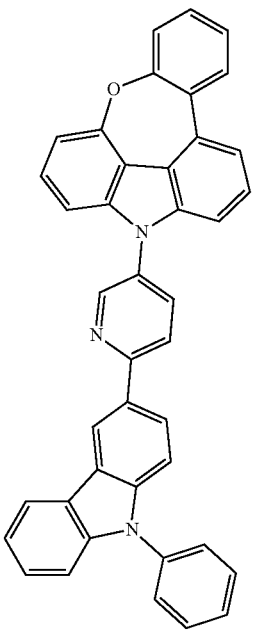
C-25
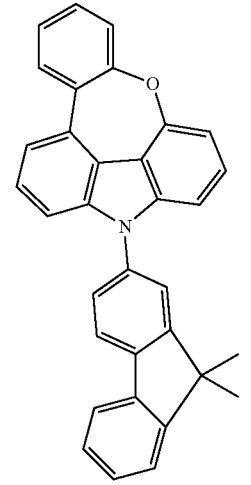

C-26
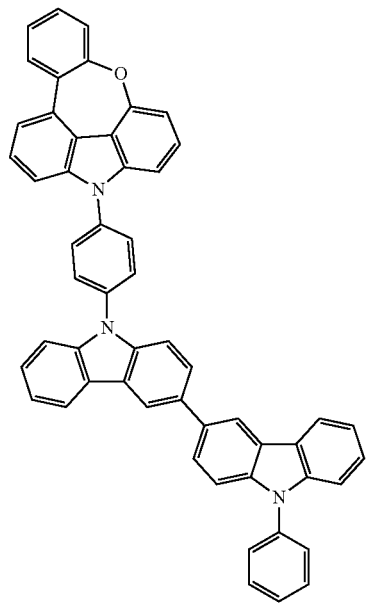
C-27
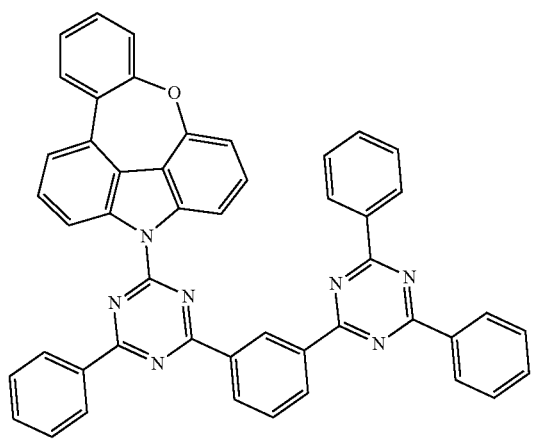
C-28
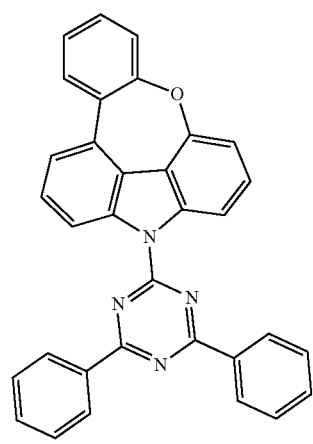
C-29
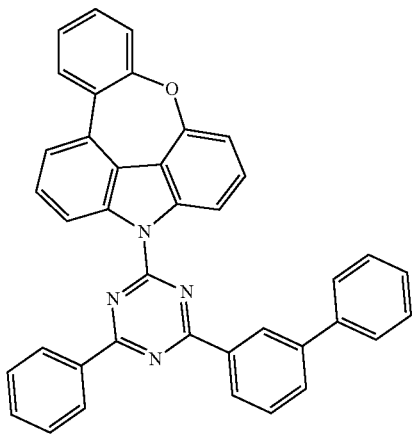
C-30
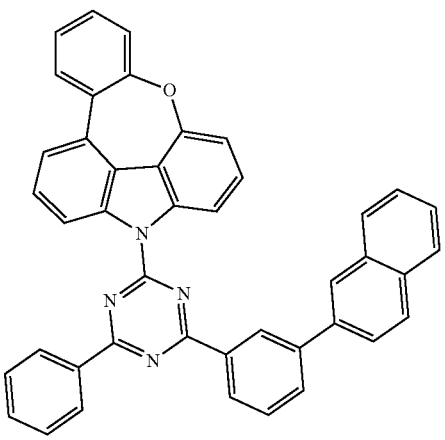
C-31
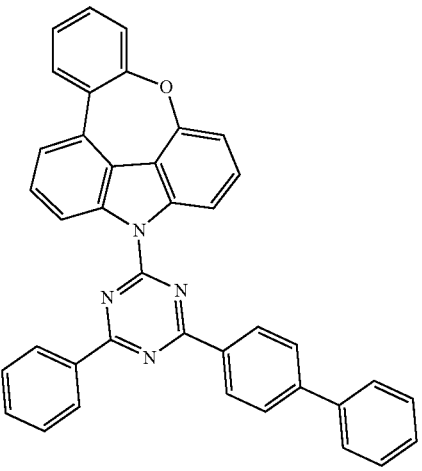

C-32
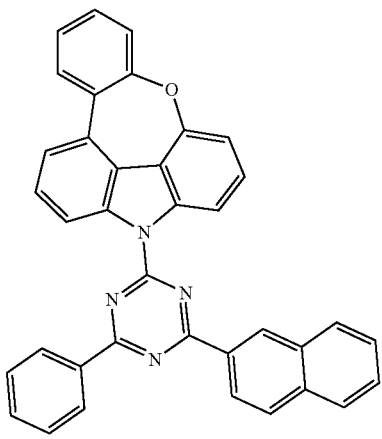
C-35
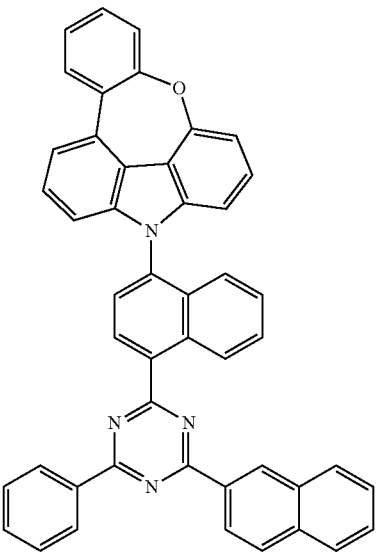
C-33
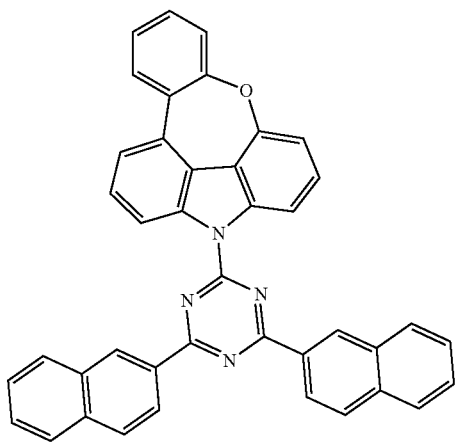
C-34
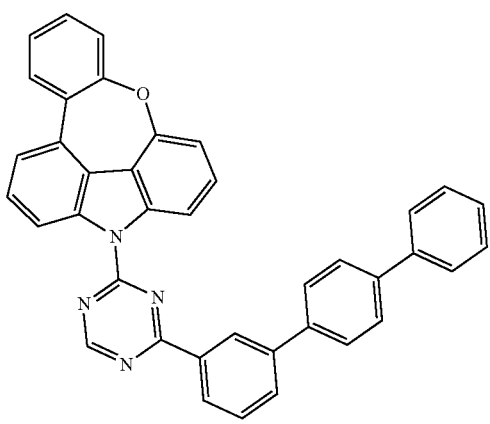
C-36
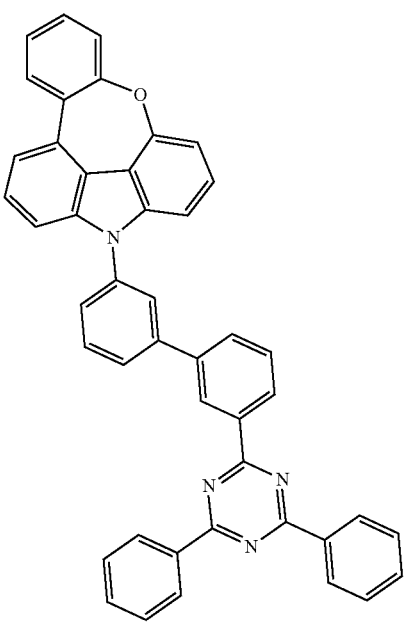

C-37
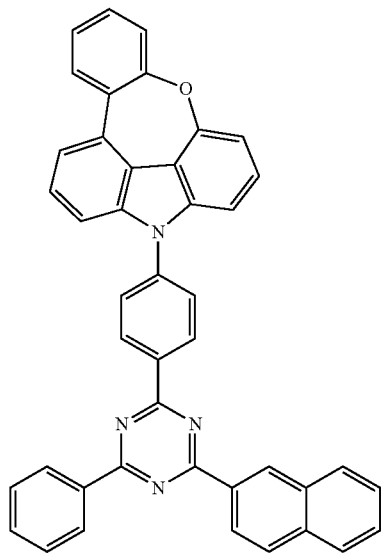
C-38
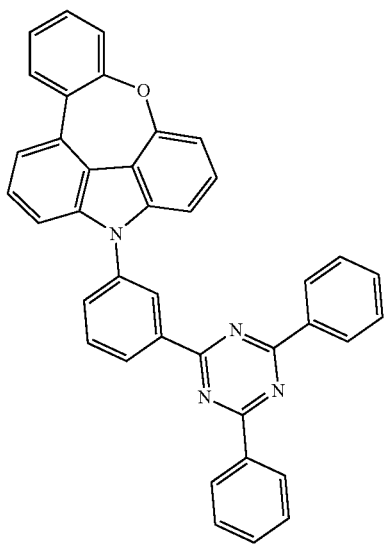
C-39
C-40
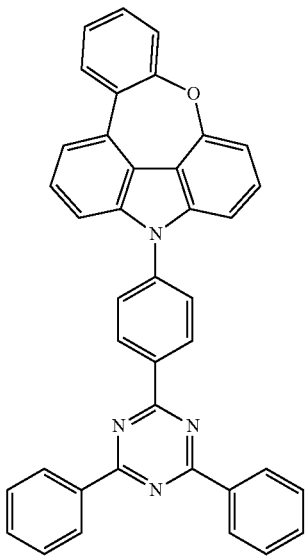
C-41
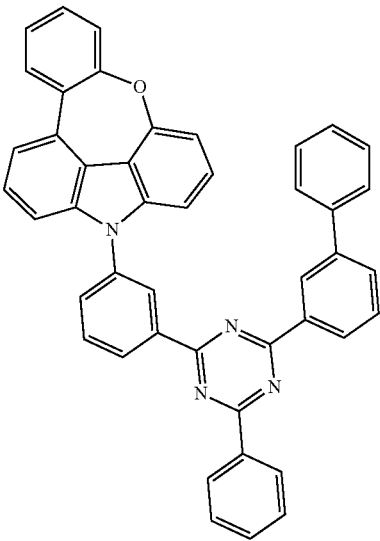

-continued
C-42
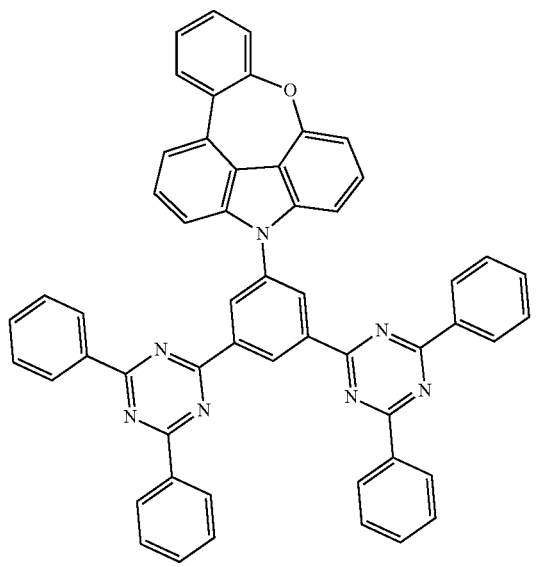
C-43
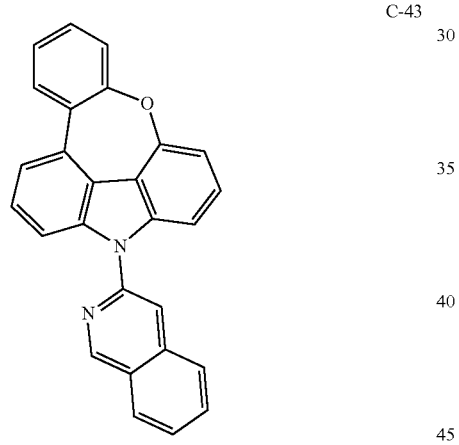
C-44
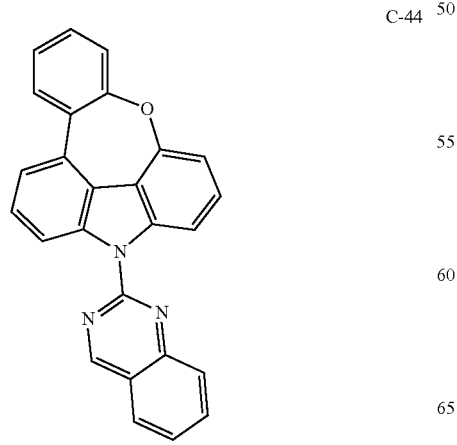
-continued
C-45
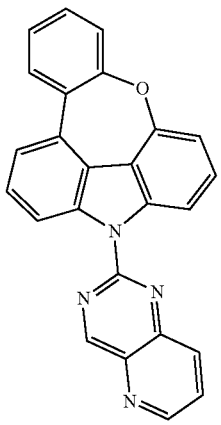
C-46
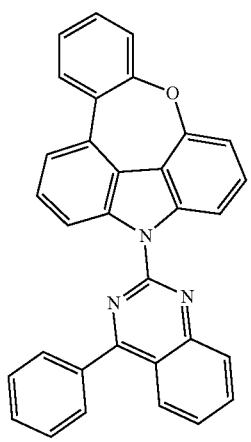
C-47
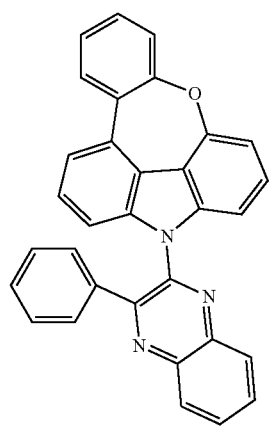

C-48
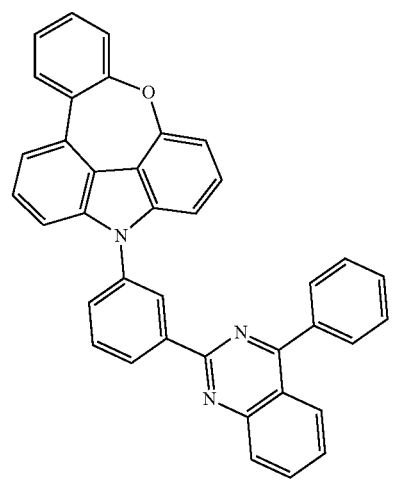
C-49
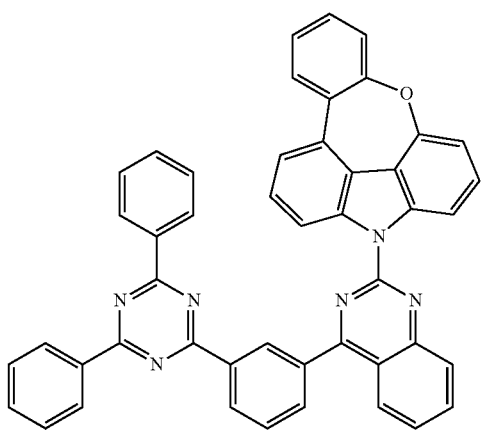
C-50
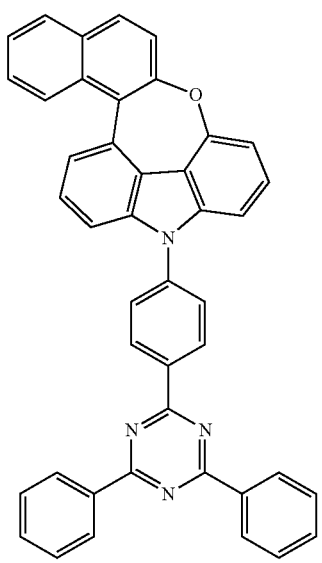
C-51
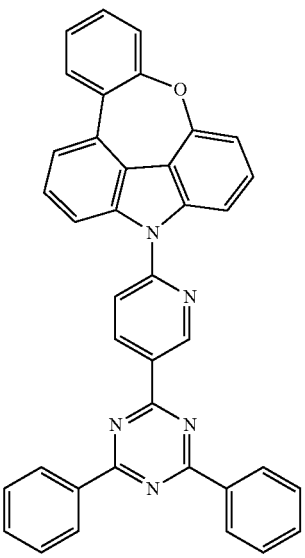
C-52
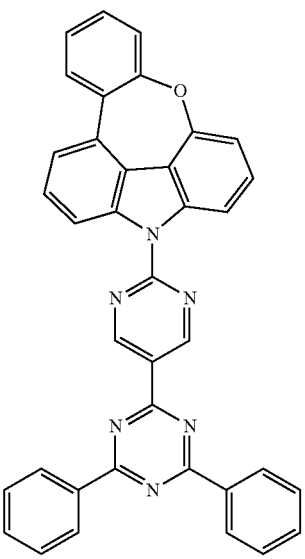
C-53
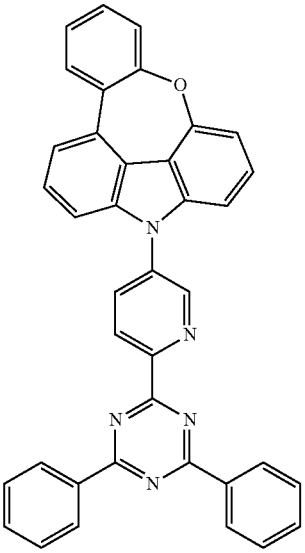

C-54
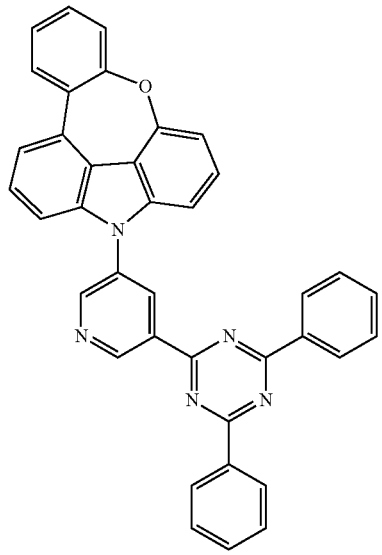
C-55
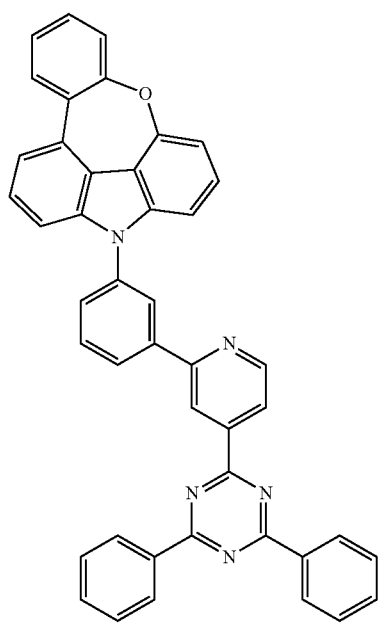
C-56
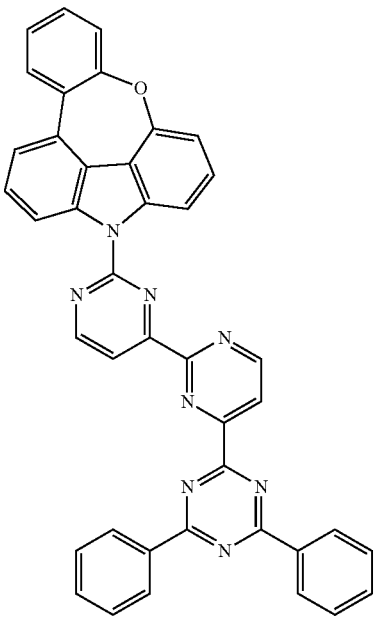
C-57
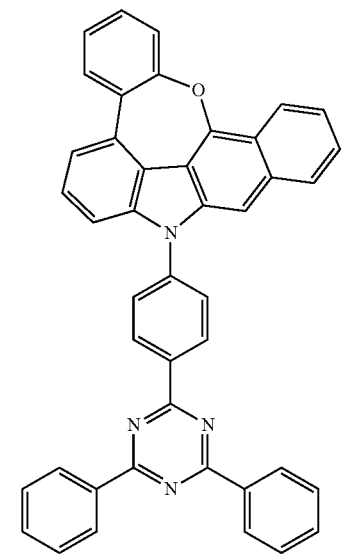
C-58
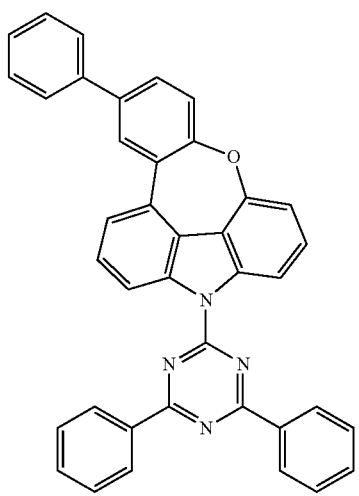

-continued
C-59
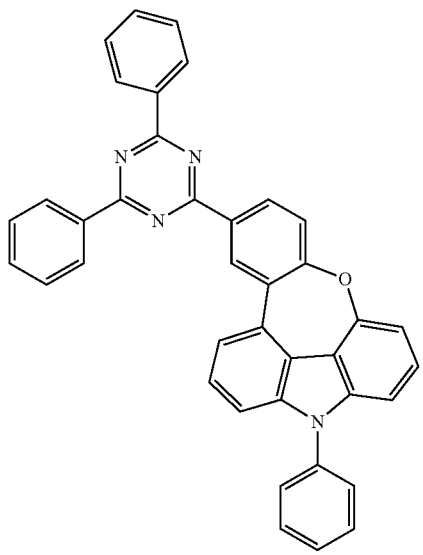
C-60
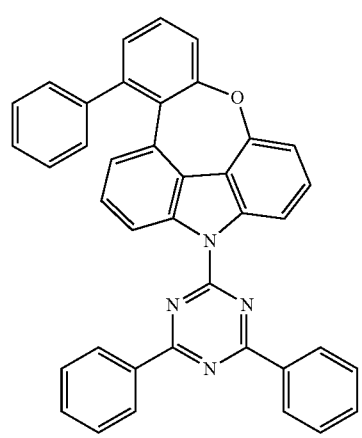
C-61
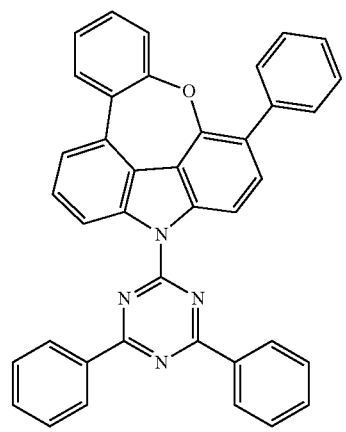
-continued
C-62
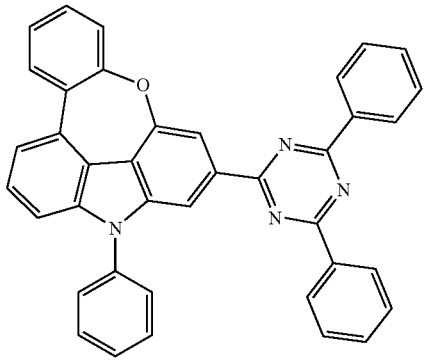
C-63
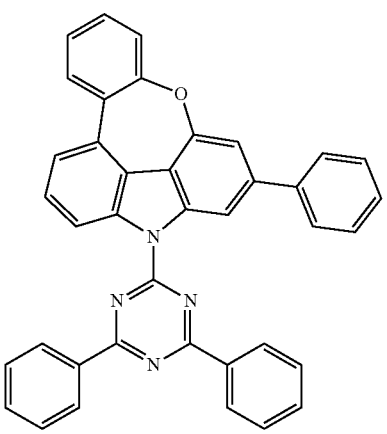
C-64
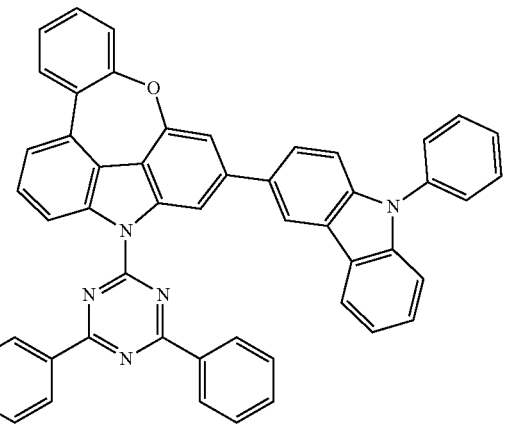

C-65
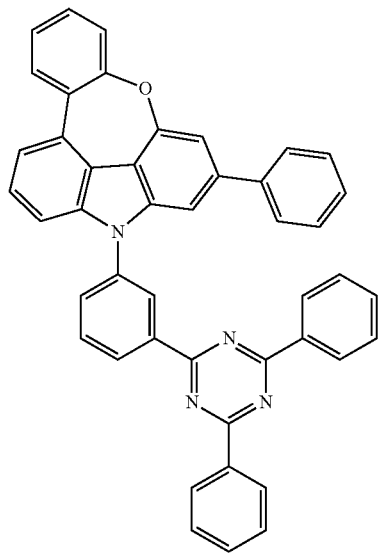
C-67
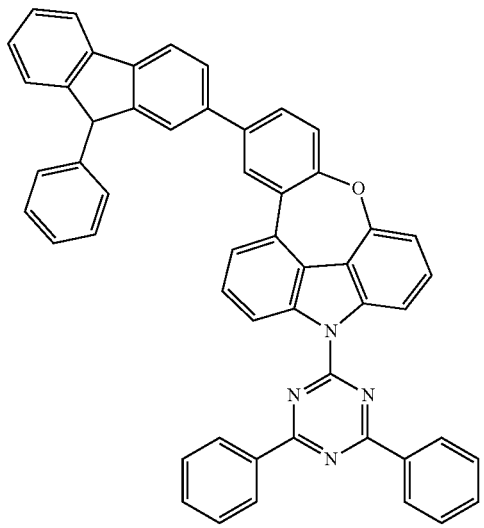
C-68
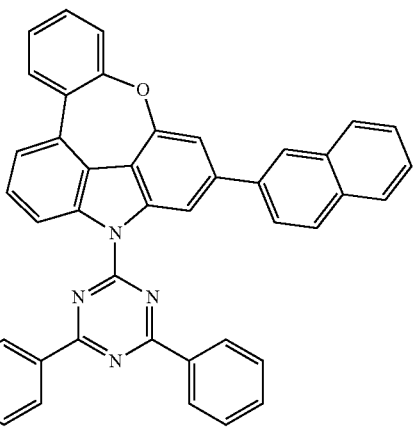
C-66
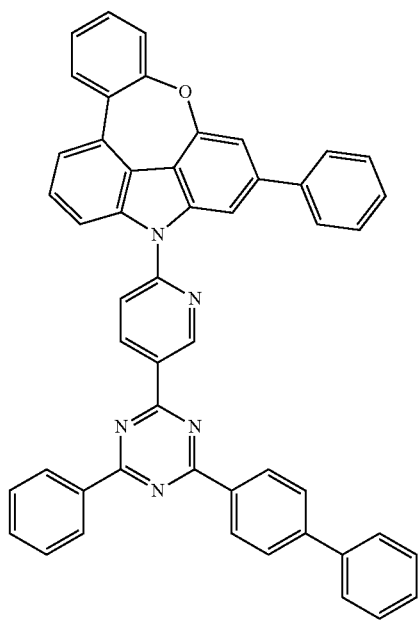
C-69
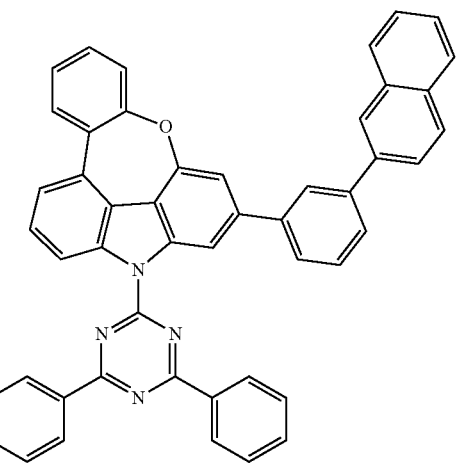

C-70
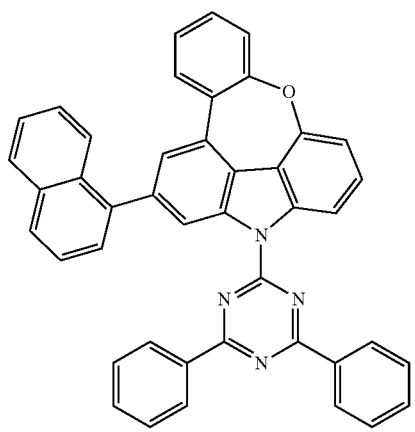
C-71
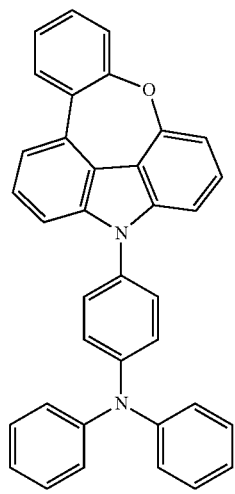
C-72
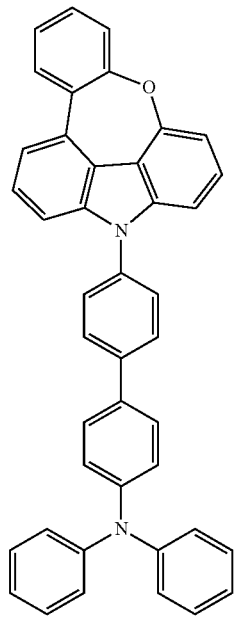
C-73
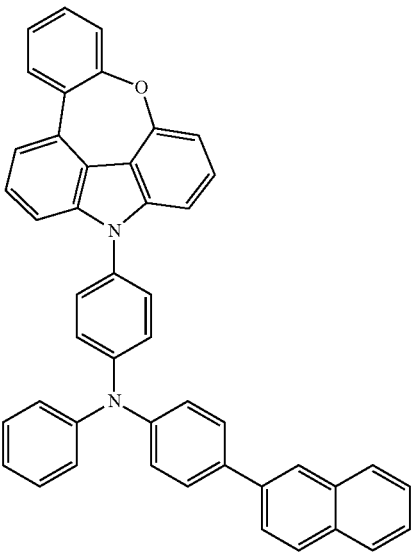
C-74
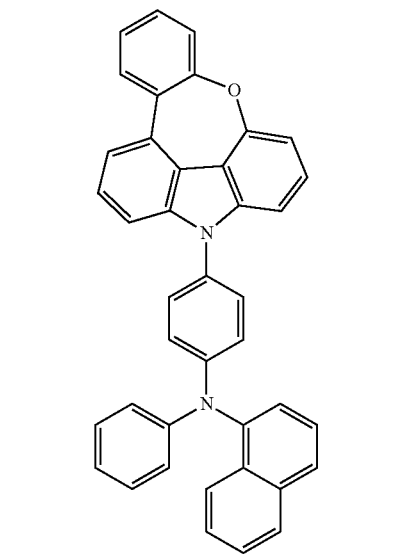
C-75
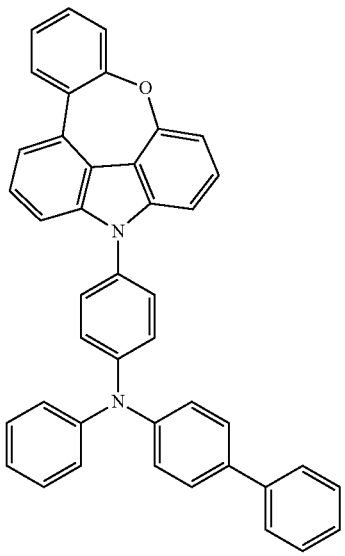

C-76
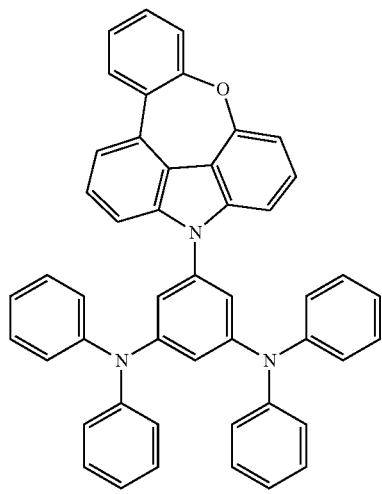
C-79
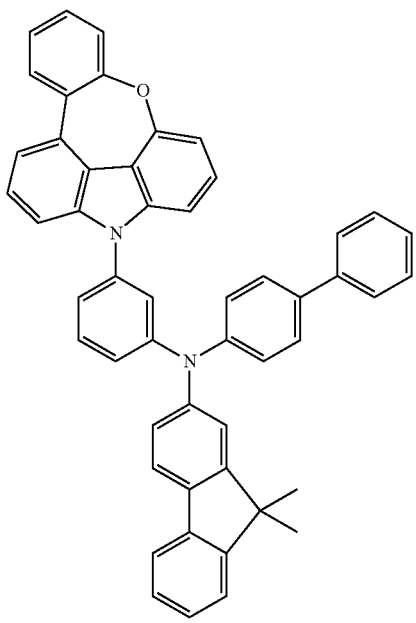
C-77
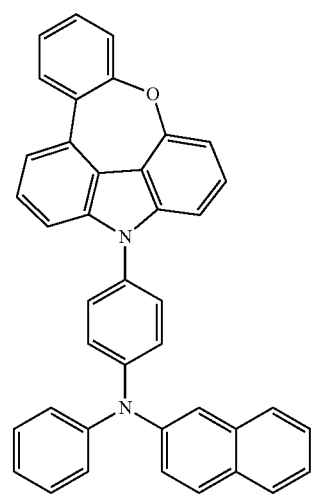
C-78
C-80
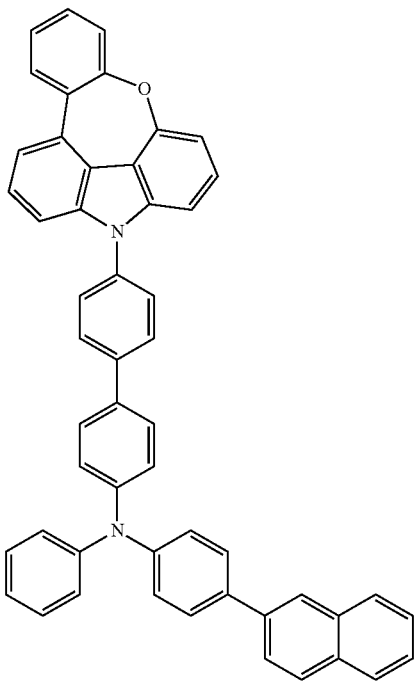

-continued
C-81
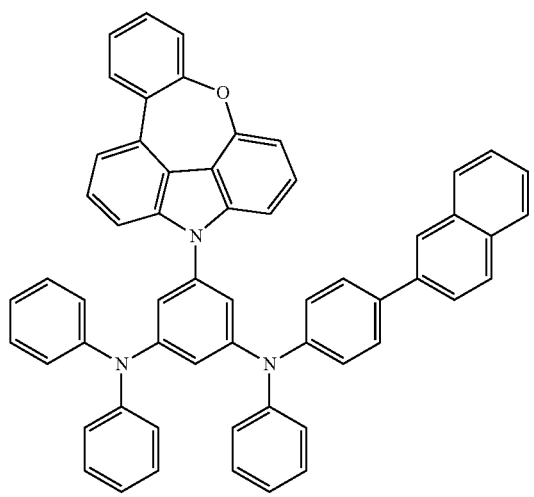
C-82
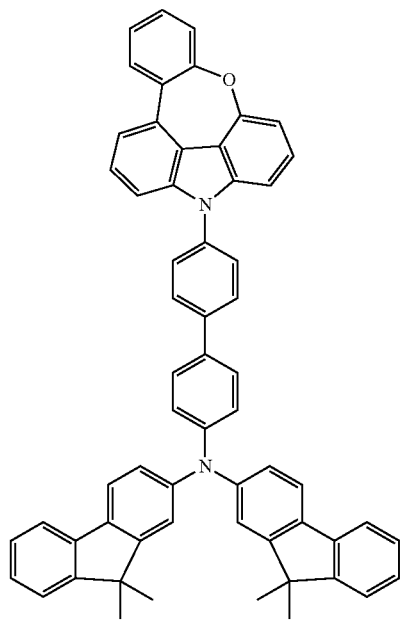
C-83
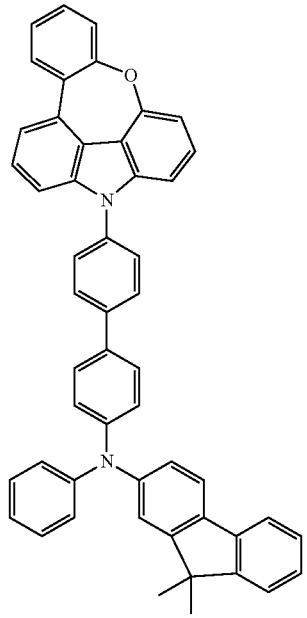
C-84
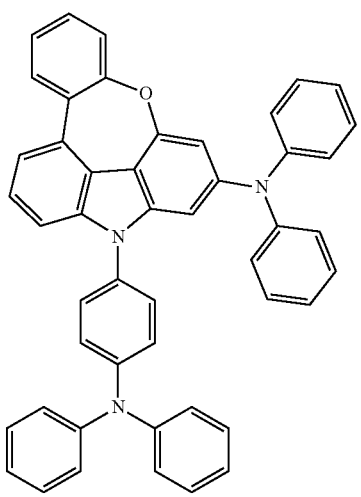
C-85
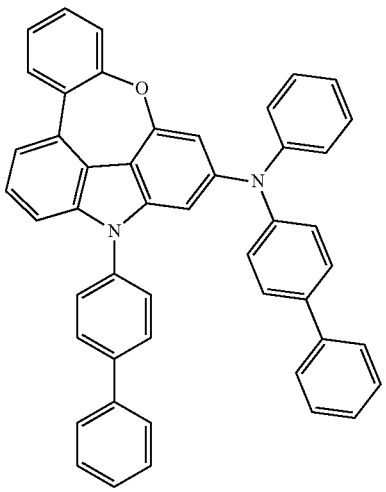

-continued
C-86
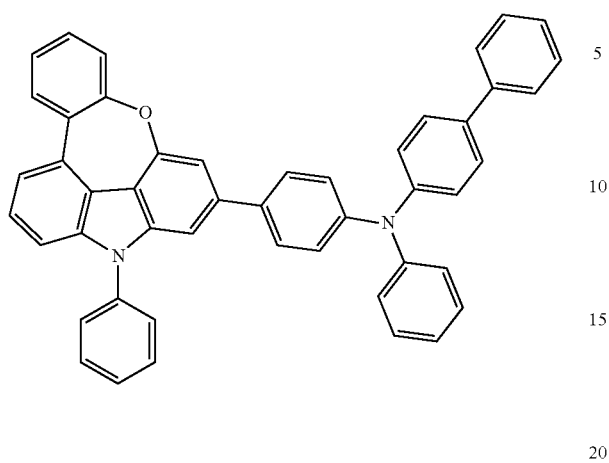
C-89
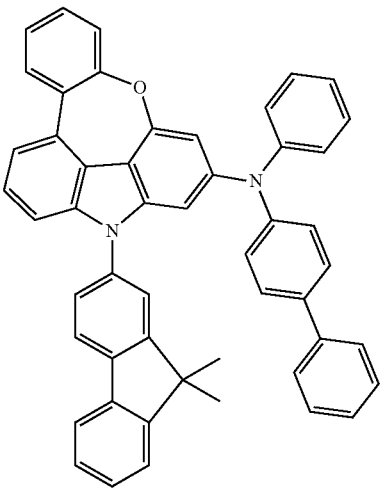
C-87
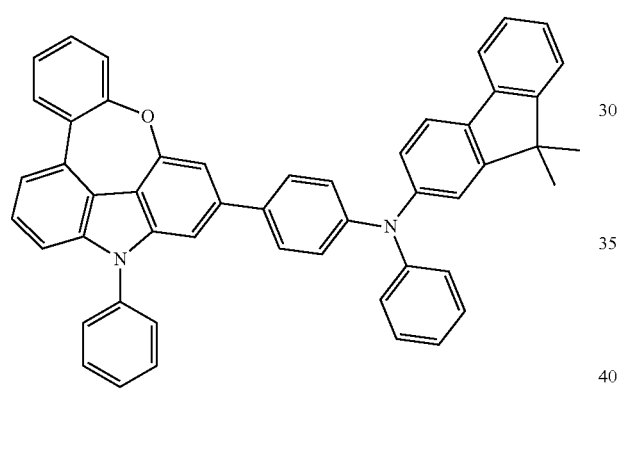
C-90
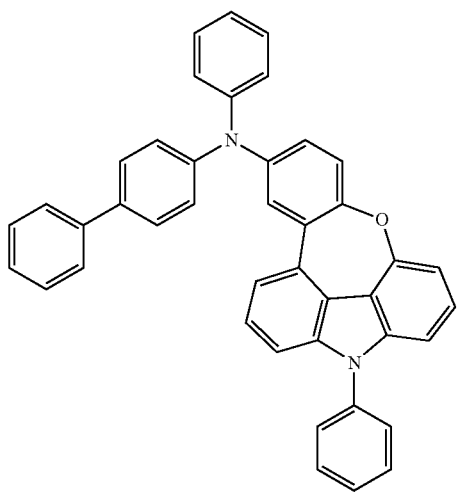
C-88
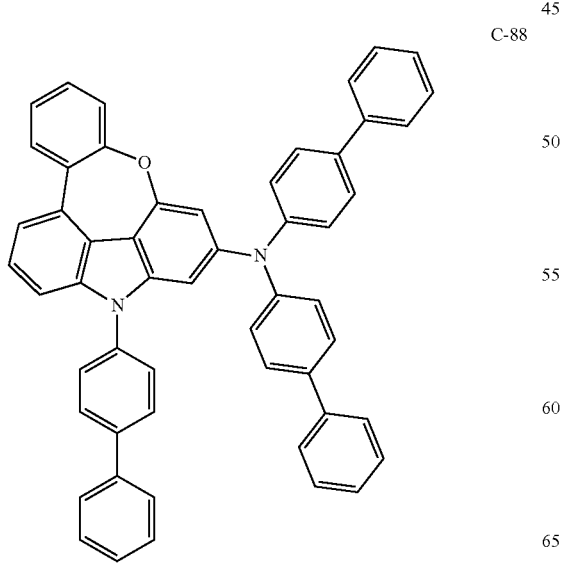
C-91
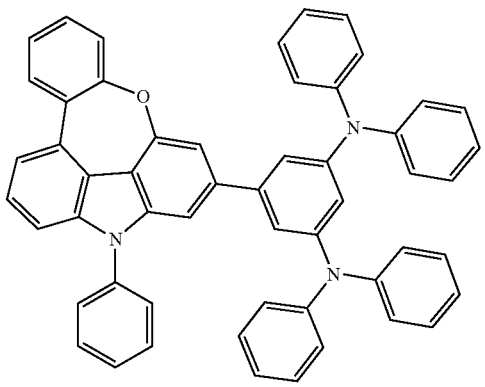

C-92
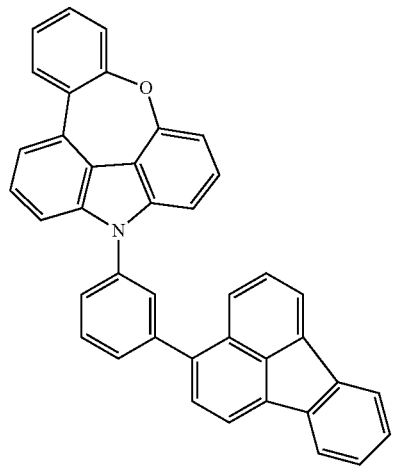
C-93
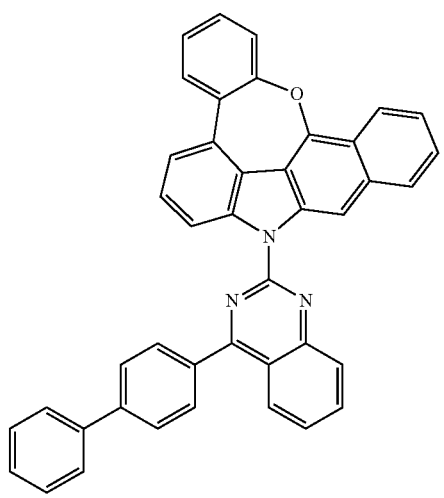
C-94
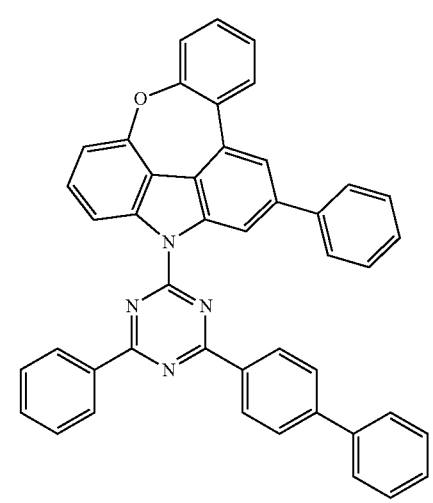
C-95
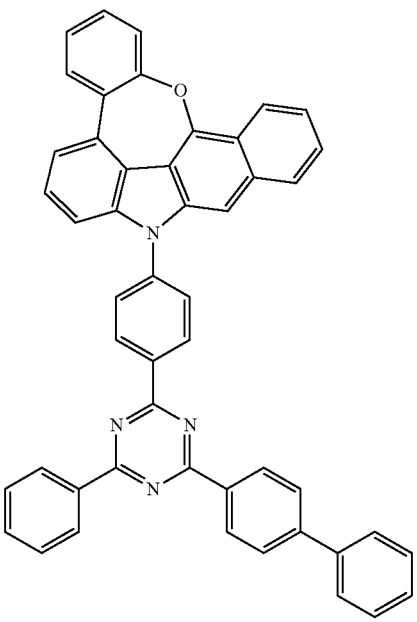
C-96
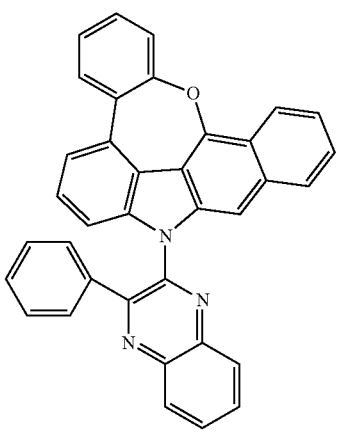

C-97

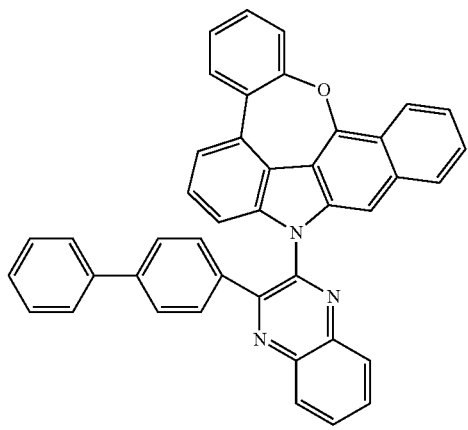

C-98

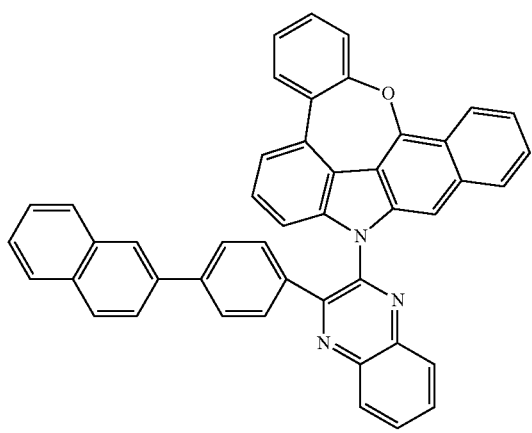

C-99

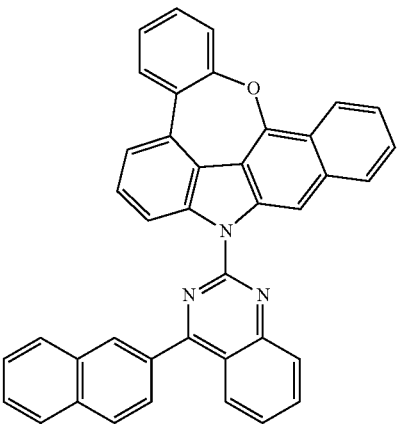

6. A host material comprising the organic electroluminescent compound according to claim 1.

7. An electron buffer material comprising the organic electroluminescent compound according to claim 1.

8. An organic electroluminescent device comprising the organic electroluminescent compound according to claim 1.

9. The organic electroluminescent device according to claim 8, wherein the organic electroluminescent device comprises at least one light-emitting layer disposed between a first electrode and a second electrode, wherein the light-emitting layer comprises a host and a dopant, wherein the host comprises a plurality of host compounds, and wherein at least one host compound of the plurality of host compounds is the organic electroluminescent compound.

10. The organic electroluminescent device according to claim 8, wherein the organic electroluminescent device comprises a first electrode; a second electrode facing the first electrode; a light-emitting layer between the first electrode and the second electrode; and an electron transport layer and an electron buffer layer between the light-emitting layer and the second electrode, and wherein the electron buffer layer comprises the organic electroluminescent compound.

* * * * *